US007022699B2

(12) United States Patent
Failli et al.

(10) Patent No.: US 7,022,699 B2
(45) Date of Patent: Apr. 4, 2006

(54) CYCLOHEXENYL PHENYL DIAZEPINES VASOPRESSIN AND OXYTOCIN RECEPTOR MODULATORS

(75) Inventors: Amedeo Arturo Failli, Princeton Junction, NJ (US); William Jennings Sanders, Fox Lake, IL (US); Eugene John Trybulski, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 379 days.

(21) Appl. No.: 10/119,611

(22) Filed: Apr. 10, 2002

(65) Prior Publication Data

US 2002/0198196 A1    Dec. 26, 2002

Related U.S. Application Data

(60) Provisional application No. 60/283,265, filed on Apr. 12, 2001.

(51) Int. Cl.
*A61P 15/06* (2006.01)
*A61K 31/55* (2006.01)
*C07D 487/12* (2006.01)

(52) U.S. Cl. ................. 514/220; 514/63; 540/561
(58) Field of Classification Search ............... 514/63, 514/220; 540/561
See application file for complete search history.

(56) References Cited

U.S. PATENT DOCUMENTS

| | | | |
|---|---|---|---|
| 4,766,108 A | 8/1988 | Ali ........................ | 514/16 |
| 5,055,448 A | 10/1991 | Manning et al. ........... | 514/16 |
| 5,070,187 A | 12/1991 | Gavras et al. ............. | 530/315 |
| 5,258,510 A | 11/1993 | Ogawa et el. ............. | 540/476 |
| 5,436,333 A | 7/1995 | Venkatesan et al. ....... | 540/586 |
| 5,459,131 A | 10/1995 | Albright et al. ........... | 514/19 |
| 5,466,584 A | 11/1995 | Tanizawa et al. .......... | 435/69.1 |
| 5,512,563 A | 4/1996 | Albright et al. ........... | 514/217 |
| 5,516,774 A | 5/1996 | Albright et al. ........... | 514/220 |
| 5,521,173 A | 5/1996 | Venkatesan et al. ....... | 514/220 |
| 5,532,235 A | 7/1996 | Albright et al. ........... | 514/215 |
| 5,536,718 A | 7/1996 | Albright et al. ........... | 514/220 |
| 5,609,851 A | 3/1997 | Bennani ................... | 424/9.454 |
| 5,654,297 A | 8/1997 | Albright et al. ........... | 514/215 |
| 5,665,719 A | 9/1997 | Bock et al. ............... | 514/227.8 |
| 5,670,509 A | 9/1997 | Evans et al. .............. | 514/278 |
| 5,726,172 A | 3/1998 | Sparks et al. ............. | 514/230.5 |
| 5,736,540 A | 4/1998 | Albright et al. ........... | 514/215 |
| 5,753,644 A | 5/1998 | Ogawa et al. ............. | 514/213 |
| 5,756,497 A | 5/1998 | Bell et al. ................. | 514/230.5 |
| 5,756,504 A | 5/1998 | Bock et al. ............... | 514/252 |
| 5,780,471 A | 7/1998 | Venkatesan et al. ....... | 514/250 |
| 5,849,735 A | 12/1998 | Albright et al. ........... | 514/220 |
| 5,880,122 A | 3/1999 | Trybulski et al. .......... | 514/220 |
| 5,968,930 A | 10/1999 | Albright et al. ........... | 514/220 |
| 6,268,359 B1 | 7/2001 | Ogawa et al. ............. | 514/215 |
| 6,340,678 B1 | 1/2002 | Matushisa et al. ........ | 514/213.01 |
| 2002/0183311 A1 | 12/2002 | Failli et al. ............... | 514/220 |
| 2003/0004159 A1 | 1/2003 | Failli et al. ............... | 514/220 |
| 2003/0008863 A1 | 1/2003 | Failli et al. ............... | 514/220 |
| 2003/0018026 A1 | 1/2003 | Failli et al. ............... | 514/220 |
| 2003/0027815 A1 | 2/2003 | Failli et al. ............... | 514/220 |
| 2003/0055046 A1 | 3/2003 | Failli et al. ............... | 514/220 |
| 2003/0055047 A1 | 3/2003 | Failli et al. ............... | 514/220 |

FOREIGN PATENT DOCUMENTS

| | | |
|---|---|---|
| EP | 0 382 185 | 8/1990 |
| EP | 0 470 514 | 2/1992 |
| EP | 0 514 667 | 11/1992 |
| EP | 0 533 240 | 3/1993 |
| EP | 0 533 242 | 3/1993 |
| EP | 0 533 243 | 3/1993 |
| EP | 0 533 244 | 3/1993 |
| EP | 0 620 216 | 10/1994 |
| EP | 0 636 625 B1 | 1/1999 |
| GB | 2 326 410 | 12/1998 |
| GB | 2 326 639 | 12/1998 |
| WO | WO 91/05549 | 5/1991 |
| WO | WO 94/01113 | 1/1994 |
| WO | WO 94/04525 | 3/1994 |
| WO | WO 94/12476 | 6/1994 |
| WO | WO 94/14796 | 7/1994 |
| WO | WO 94/20473 | 9/1994 |
| WO | WO 96/09824 | 4/1996 |
| WO | WO 96/22282 | 7/1996 |
| WO | WO 96/22292 | 7/1996 |

(Continued)

OTHER PUBLICATIONS

Zingg et al., The Oxytocin Receptor, TRENDS in Endocrinology and Metabolism, vol. 14, No. 5, pp. 222-227, Jul. 2003.*

(Continued)

*Primary Examiner*—Brenda Coleman
(74) *Attorney, Agent, or Firm*—Woodcock Washburn LLP

(57) ABSTRACT

The present invention provides novel tricyclic diazepine compounds and methods and pharmaceutical compositions utilizing them for the treating or preventing disorders including diabetes insipidus, nocturnal enuresis, nocturia, urinary incontinence, bleeding and coagulation disorders, congestive heart failure or for inducing temporary delay of urination, and in conditions with increased vascular resistance and coronary vasoconstriction; and for the treating or preventing disorders remedied or alleviated by oxytocin antagonist activity, including suppression of preterm labor, dysmenorrhea, endometritis, and for suppressing labor at term prior to caesarean delivery. These compounds are also useful in enhancing fertility rates, enhancing survival rates and synchronizing estrus in farm animals; and treatment of disfunctions of the oxytocin system in the central nervous system including obsessive compulsive disorder (OCD) and neuropsychiatric disorders.

15 Claims, No Drawings

FOREIGN PATENT DOCUMENTS

| | | |
|---|---|---|
| WO | WO 96/22294 | 7/1996 |
| WO | WO 96/22775 | 8/1996 |
| WO | WO 97/25992 | 7/1997 |
| WO | 98/20011 | 5/1998 |
| WO | 99/06409 | 2/1999 |
| WO | WO 99/24051 | 5/1999 |

OTHER PUBLICATIONS

Mats Akerlund, Acta Obstet. Gynecol. Scand., 1987, 459-461, 66.
Mats Akerlund, Reg. Pept., 1993, 187-191, 45.
Ian M. Bell et al., J. Med. Chem., 1998, 2146-2163, 41.
Ya Li Chen et al., Eur. J. Pharmacol., 1999, 25-51, 376.
J.J. Evans et al., J. Endocrinol., 1989, 107-116, 122.
Ben E. Evans et al., J. Med. Chem., 1993, 3993-4006, 36.
Ben E. Evans et al., J. Med. Chem., 1992, 3919-3927, 35.
Anna-Riitta Fuchs et al., Science, 1982, 1396-1398, 215.
Andre Giroux et al., Tetr. Lett., 1997, 3841-3844, 38.
T. Murphy Goodwin et al., Obstet. Gynecol., 1996, 331-336, 88.
Aleksandar Jovanovic et al., Br. J. Pharmacol., 1997, 1468-1474, 12.
Mario Maggi et al., J. Clin. Endocrinol. Metab., 1990, 1142-1154, 70.
A. Okano, J. Reprod. Dev., 1996, 67-70, 42 (Suppl.).
D.J. Pettibone et al., Biochem. Soc. Trans., 1997, 1051-1057, 25(3).
V. Rettori et al., Proc. Nat. Acad. Sci. U.S.A., 1997, 2741-2744, 94.
G. Robinson et al., J. Endocrinol., 1990, 425-432, 125.
Olga Wellnitz et al., J. Dairy Res., 1999, 1-8, 66.
Gabor L. Kovacs et al., Psychoneuroendocrinology, 1998, 945-962, 23(8).
Margaret M. McCarthy et al., Molecular Medicine Today, 1997, 269-275, 3(6).
James. F. Leckman et al., Psychoeuroendocrinology, 1994, 723-749, 19(8).
Banker, G. S. et al., "Modern Pharmaceutics, 3ed.", Marcel Dekker, New York, 1996, p. 596.
PubMed Abstract 12848639, also cited as Acta Obstet Gynecol, 2003, 82(8), 687-704.
PubMed Abstract 12436949, also cited as Prog Brain Res, 2002, 139, 359-65.
PubMed Abstract 9891619, also cited as Clin Perinatol, 1998, 25(4), 859-71.
Wolff, Manfred E., "Burger's Medicinal Chemistry, 5ed, Part 1", John Wiley & Sons, 1995, pp. 975-977.

* cited by examiner

CYCLOHEXENYL PHENYL DIAZEPINES VASOPRESSIN AND OXYTOCIN RECEPTOR MODULATORS

This application claims priority from provisional application Ser. No. 60/283,265, filed Apr. 12, 2001, the entire disclosure of which is hereby incorporated by reference.

This invention concerns novel tricyclic diazepines with affinity for the vasopressin and/or oxytocin receptors which can act as modulators of vasopressin and/or oxytocin effects in vivo, as well as methods of their manufacture, methods of treatment and pharmaceutical compositions utilizing these compounds. The compounds of the present invention are useful therapeutic agents for treating conditions in mammals, particularly in humans where decreased levels of vasopressin are desired, such as in congestive heart failure, in disease conditions with excessive renal water reabsorption and in conditions with increased vascular resistance and coronary vasoconstriction. They are also useful therapeutic agents for treating diseases in mammals, particularly humans, affecting the vasopressin system which are characterized by excretion of excessive volumes of diluted urine, including central or nephrogenic diabetes insipidus, for treating nocturnal enuresis, nocturia, urinary incontinence, bleeding and coagulation disorders, or temporary delay of urination. By preventing oxytocin from binding to its receptors they are useful in the prevention and/or suppression of preterm labor, for the suppression of labor at term prior to caesarean delivery, to facilitate transport to a medical facility, and for the treatment of dysmenorrhea. They are also useful in enhancing fertility rates, enhancing survival rates and synchronizing estrus in farm animals; and they may be useful in the prevention and treatment of disfunctions of the oxytocin system in the central nervous system, including obsessive compulsive disorder (OCD) and neuropsychiatric disorders.

BACKGROUND OF THE INVENTION

Vasopressin is involved in some cases of congestive heart failure where peripheral resistance is increased. The hormone exerts its action through two well defined receptor subtypes: vascular $V_{1a}$ and renal epithelial $V_2$ receptors. $V_{1a}$ receptor antagonists may decrease systemic vascular resistance, increase cardiac output and prevent vasopressin induced coronary vasoconstriction. Thus, in conditions with vasopressin induced increases in total peripheral resistance and altered local blood flow, $V_{1a}$ receptor antagonists may be therapeutically useful agents. $V_{1a}$ receptor antagonists may decrease blood pressure, induce hypotensive effects and thus be therapeutically useful in treatment of some types of hypertension.

Vasopressin-induced antidiuresis, mediated by renal epithelial $V_2$ receptors, helps to maintain normal plasma osmolality, blood volume and blood pressure. Antidiuresis is regulated by the hypothalamic release of vasopressin (antidiuretic hormone) which binds to specific $V_2$ receptors on renal collecting tubule cells. This binding stimulates adenyl cyclase and promotes the cAMP-mediated incorporation of water pores into the luminal surface of these cells. The blockade of vasopressin $V_2$ receptors is useful in treating diseases characterized by excess renal reabsorption of free water. Vasopressin-induced antidiuresis, mediated by renal epithelial $V_2$ receptors, helps to maintain normal plasma osmolality, blood volume and blood pressure. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of the antiduretic hormone. On the basis of biochemical and pharmacological effects of the hormone, antagonists of vasopressin are expected to be therapeutically useful in the treatment or prevention of state diseases involving vasopressin disorders in mammals, which include inducing vasodilation and aquaresis (free-water diuresis), treating hypertension, and inhibiting platelet aggregation. They are useful in the treatment of cardiac insufficiency, coronary vasospam, cardiac ischemia, renal vasospasm, cirrhosis with ascites, the syndrome of inappropriate antidiuretic hormone secretion (SIADH), congestive heart failure, nephritic syndrome, brain edema, cerebral ischemia, cerebral hemorrhage-stroke, thrombosis bleeding, and abnormal states of water retention. Furthermore, vasopressin receptor antagonists have been found to be useful in treating disturbances or illnesses of the inner ear, particularly those related to Meniere's disease (Zenner et al., WO 99/2405-A2 (1999); and for the prevention and treatment of ocular circulatory disorders, particularly intraocular hypertension or glaucoma and vision disorders such as shortsightedness (Ogawa et al., WO 99/38533-A1 (1999)).

Vasopressin plays a vital role in the conservation of water by concentrating the urine at the site of the collecting ducts of the kidney. The collecting ducts of the kidney are relatively impermeable to water without the presence of vasopressin at the receptors and therefore, the hypotonic fluid formed after filtering through the glomeruli, passing the the proximal convoluted tubule, the loops of Henle, and the distal convoluted tubules, is excreted as dilute urine. However, during dehydration, volume depletion or blood loss, vasopressin is released from the brain and activates the vasopressin $V_2$ receptors in the collecting ducts of the kidney rendering the ducts permeable to water; hence water is reabsorbed and a concentrated urine is excreted. In patients and animals with central or neurogenic diabetes insipidus, the synthesis of vasopressin in the brain is defective and therefore, they produce no or very little vasopressin, but their vasopressin receptors in the kidneys are normal. Because they cannot concentrate the urine, they may produce as much as ten times the urine volumes of their healthy counterparts and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination whenever desirable.

Premature labor remains the leading cause of perinatal mortality and morbidity. Infant mortality dramatically decreases with increased gestational age. While many agents have been developed for the treatment of premature labor in the last 40 years, the incidence of pre-term births and low birth weight infants has remained relatively unchanged. Therefore, there is an unmet need for safer and more efficacious agents for the treatment of preterm labor with better patient tolerability. Currently available agents (terbutaline, albuterol), magnesium sulfate, NSAIDs (indomethacin), and calcium channel blockers are not very effective and their safety profile is not ideal. One target of interest is the oxytocin receptor and a selective oxytocin receptor antagonist has been proposed as an ideal tocolytic agent. There is evidence strongly suggesting that oxytocin may play a critical role in the initiation and progression of labor in humans (Fuchs et al. *Science* 215, 1396–1398 (1982); Maggi et al. *J. Clin. Endocrinol. Metab.* 70, 1142–1154 (1990); Åkerlund, *Reg. Pept.* 45, 187–191 (1993); Åkerlund, Int. Congr. Symp. Semin. Ser., *Progress in Endocrinology* 3, 657–660 (1993); Åkerlund et al., in *Oxytocin*, Ed. R. Ivell and J. Russel, Plenum Press, New York, pp 595–600 (1995)). Thus, a selective oxytocin antagonist is expected to block the major effects of oxytocin exerted mainly on the uterus at term, and to be more efficacious than current therapies for the treatment of preterm labor. By virtue of its direct action on the receptors in the uterus an oxytocin antagonist is also expected have fewer side effects and an improved safety profile.

Oxytocin antagonists can produce contraception in mammals by inhibiting the release of oxytocin-stimulated luteneizing hormone (LH) from pituitary cells (Rettori et al., *Proc. Nat. Acad. Sci. U.S.A.* 94, 2741–2744 (1997); Evans et al., *J. Endocrinol.*, 122, 107–116 (1989); Robinson et al., *J. Endocrinol.* 125, 425–432 (1990)).

The administration of oxytocin receptor antagonists to farm animals after fertilization have been found to enhance fertility rates by blocking oxytocin induced luteolysis leading to embryonic loss (Hickey et al., WO 96/09824 A1 (1996), Sparks et al., WO 97/25992 A1 (1997); Sparks et al., U.S. Pat. No. 5,726,172 A (1998)). Thus, oxytocin receptor antagonists can be useful in farm animal husbandry to control timing of parturition and delivery of newborns resulting in enhanced survival rates. They can be also useful for the synchronization of estrus by preventing oxytocin induced corpus luteum regression and by delaying estrus (Okano, *J. Reprod. Dev.* 42 (Suppl.), 67–70 (1996)). Furthermore oxytocin receptor antagonists have been found to have a powerful effect in inhibiting oxytocin-induced milk ejection in dairy cows (Wellnitz et al., *Journal of Dairy Research* 66, 1–8 (1999)).

Oxytocin is also synthesized in the brain and released in the central nervous system. Recent studies have established the importance of central oxytocin in cognitive, affiliative, sexual and reproductive behavior, and in regulating feeding, grooming and responses to stress in animals. Oxytocin may also influence normal behavior in humans. Modulators of oxytocin binding to its receptors in the central nervous system may be useful in the prevention and treatment of disfunctions of the oxytocin system, including obsessive compulsive disorder (OCD) and other neuropsychiatric disorders (Lovacs et al., *Psychoneuroendocrinology* 23, 945–962 (1998); McCarthy et al., *U.K. Mol. Med. Today* 3, 269–275 (1997); Bohus, *Peptidergic Neuron [Int. Symp. Neurosecretion]*, 12th (1996), 267–277, Publ, Birkhauser, Basel, Switz.; Leckman et al., *Psychoneuroendocrinology* 19, 723–749 (1994).

Oxytocin antagonists also showing antagonist activity at the vasopressin $V_{1a}$ receptors have the ability to block uterine contractions induced by oxytocin and vasopressin. Thus, these compounds can be useful in the treatment of dysmenorrhea, a condition characterized by pain during menstruation. Primary dysmenorrhea is associated with ovulatory cycles, and it is the most common complain of gynecologic patients. Myometrial hypercontractility and decreased blood flow to the uterus are thought to be causative factors for the symptoms of primary dismenorrhea (Åkerlund, *Acta Obstet. Gynecol. Scand.* 66, 459–461 (1987)). In particular, vasoconstriction of small uterine arteries by vasopressin and oxytocin is thought to produce tissue ischemia and pain (Jovanovic et al., *Br. J. Pharmacol.*, 12, 1468–1474 (1997); Chen et al., *Eur. J. Pharmacol.*, 376, 25–51 (1999)).

The following prior art references describe peptidic vasopressin antagonists: Manning et al. *J. Med. Chem.*, 35, 382 (1992); Manning et al, *J. Med. Chem.*, 35, 3895 (1992); Gavras et al., U.S. Pat. No. 5,070,187 (1991); Manning et al., U.S. Pat. No. 5,055,448 (1991); Ali, U.S. Pat. No. 4,766,108 (1988); Ruffolo et al., *Drug News and Perspectives*, 4(4), 217 (1991).

The following prior art references describe peptidic oxytocin antagonists: Hruby et al., Structure-Activity Relationships of Neurohypophyseal Peptides, in *The Peptides: Analysis, Synthesis and Biology*, Udenfriend and Meienhofer Eds., Academic Press, New York, Vol. 8, 77–207 (1987); Pettibone et al., *Endocrinology*, 125, 217 (1989); Manning et al., Synthesis and Some Uses of Receptor-Specific Agonists and Antagonists of Vasopressin and Oxytocin, *J. Recept. Res.*, 13, 195–214 (1993); Goodwin et al., Dose Ranging Study of the Oxytocin Antagonist Atosiban in the Treatment of Preterm Labor, *Obsetet. Gynecol.*, 88, 331–336 (1996). Peptidic oxytocin antagonists suffer from a lack of oral activity and many of these peptides are non-selective antagonists since they also exhibit vasopressin antagonist activity. Bock et al. [*J. Med. Chem.* 33, 2321 (1990)], Pettibone et al. [*J. Pharm. Exp. Ther.* 256, 304 (1991)], and Williams et al. [*J. Med. Chem.*, 35, 3905 (1992)] have reported on potent hexapeptide oxytocin antagonists which also exhibit weak vasopressin antagonistic activity in binding to $V_1$ and $V_2$ receptors.

Various non-peptidic oxytocin antagonists and/or oxytocin/vasopressin (AVP) antagonists have recently been reported by Pettibone et al., *Endocrinology*, 125, 217 (1989); Yamamura et al., *Science*, 252, 572–574 (1991); Yamamura et al., *Br. J. Pharmacol.*, 105, 787 (1992); Evans et al., *J. Med. Chem.*, 35, 3919–3927 (1992); Pettibone et al., *J. Pharmacol. Exp. Ther*, 264, 308–314 (1992); Ohnishi et al., *J. Clin. Pharmacol.* 33, 230–238, (1993); Evans et al., *J. Med. Chem.* 36, 3993–4006 (1993); Pettibone et al., *Drug Dev. Res.* 30, 129–142 (1993); Freidinger et al., General Strategies in Peptidomimetic Design: Applications to Oxytocin Antagonists, in *Perspect. Med. Chem.* 179–193 (1993), Ed. B. Testa, Verlag, Basel, Switzerland; Serradeil-LeGal, *J. Clin. Invest*, 92, 224–231 (1993); Williams et al., *J. Med. Chem.* 37, 565–571 (1994); Williams et al., *Bioorg. Med. Chem.* 2, 971–985 (1994); Yamamura et al., *Br. J. Pharmacol.*, 105, 546–551 (1995); Pettibone et al., *Advances in Experimental Medicine and Biology* 395, 601–612 (1995); Williams et al., *J. Med. Chem.* 38, 4634–4636 (1995); Hobbs et al., *Biorg. Med. Chem. Lett.* 5, 119 (1995); Williams et al., *Curr. Pharm. Des.* 2, 41–58 (1996); Freidinger et al., *Medicinal Research Reviews*, 17, 1–16 (1997); Pettibone et al., *Biochem. Soc. Trans.* 25 (3), 1051–1057 (1997); Bell et al., *J. Med. Chem.* 41, 2146–2163 (1998); Kuo et al., *Bioorg. Med. Chem. Lett.* 8, 3081–3086 (1998); Williams et al., *Biorg. Med. Chem. Lett.* 9, 1311–1316 (1999).

Non-peptidic vasopressin antagonists have recently been disclosed, Albright et al. U.S. Pat. No. 5,536,718-A, U.S. Pat. No. 5,532,235-A, U.S. Pat. No. 5,516,774-A, U.S. Pat.

No. 5,512,563-A, U.S. Pat. No. 5,459,131-A; Venkatesan et al. U.S. Pat. No. 5,521,173-A; Ogawa et al., EP 0514667-A1, EPO 382185-A2, WO 91/05549 and U.S. Pat. No. 5,258,510, WO 94/04525; Yamanouchi Pharm. Co. Ltd. WO 94/20473, WO 94/12476, WO94/14796; Fujisawa Co, Ltd. EP 620216-A1; Ogawa et al. EP470514A; Bock et al. EP 0533242-A and EP 0533244-A; Erb et al. EP 0533240-A; Gilbert et al. EP 0533243 A. Certain carbostyril derivatives and bicyclic azepines are disclosed as oxytocin and vasopressin antagonists by Ogawa et al. in WO 94/01113 (1994); benzoheterocyclic derivatives as vasopressin and oxytocin antagonists are disclosed by Ogawa et al. in WO 95/34540-A (1995); benzazepine derivatives with anti-vasopressin activity, oxytocin antagonistic activity and vasopressin agonist activity, useful as vasopressin antagonists, vasopressin agonists and oxytocin antagonists are disclosed by Ogawa et al. in WO 97/22591 (1997) and U.S. Pat. No. 6,096,736 (2000); benzoxazinones are disclosed as oxytocin and vasopressin receptor antagonists by Sparks et al. in WO 97/25992 (1997); Williams et al. disclose piperidine oxytocin and vasopressin receptor antagonists in WO 96/22775 (1996); Bock et al. disclose benzoxazinone and benzopyrimidinone piperidines useful as oxytocin and vasopressin receptor antagonists in U.S. Pat. No. 5,665,719 (1997); piperazines and spiropiperidines useful as oxytocin and vasopressin receptor antagonists are disclosed by Evans et al. in U.S. Pat. No. 5,670,509 (1997) and by Bock et al. in U.S. Pat. No. 5,756,504 (1998); Bell et al. disclose piperazine oxytocin receptor antagonists in UK Patent Application, GB 2 326 639 A (1998); Bell et al. disclose benzoxazinone and quinolinone oxytocin and vasopressin receptor antagonists in UK Patent Application GB 2 326 410 A (1998); Bell et al. disclose benzoxazinone oxytocin and vasopressin receptor antagonists in U.S. Pat. No. 5,756,497 (1998); Matsuhisa et al. disclose difluoro tetrahydrobenzazepine derivatives as oxytocin antagonists in WO 98/39325 (1998); and Ogawa et al. disclose heterocyclic bisamides with vasopressin and oxytocin antagonist activity in U.S. Pat. No. 5,753,644 (1998). Ohtake et al. disclose ocular tension lowering agents and phosphoric ester derivatives exhibiting vasopressin $V_1$ receptor antagonism in WO 99/65525 (1999); and Hoekstra et al. disclose tricyclic benzodiazepines useful as vasopressin receptor antagonists for treating conditions involving increased vascular resistance and cardiac insufficiency in WO 00/43398 (2000).

Trybulski et al. disclose 3-carboxamide derivatives of pyrrolobenzodiazepine bisamides with vasopressin antagonist activity in U.S. Pat. No. 5,880,122 (1999); bicyclic thienoazepines with vasopressin and oxytocin receptor antagonist activity are disclosed by Albright et al. in WO 96/22294 (1996) and U.S. Pat. No. 5,654,297 (1997); and tricyclic benzazepines with vasopressin and oxytocin receptor antagonist activity are disclosed by Albright et al. in U.S. Pat. No. 5,849,735 (1998); and Venkatesan et al. in U.S. Pat. No. 5,436,333 teach a process for the preparation of tricyclic heterocycles which are useful as intermediates in the production of cardiovascular agents.

Venkatesan et al. broadly disclose tricyclic benzazepines with vasopressin and oxytocin antagonist activity in U.S. Pat. No. 5,521,173 (1996), WO 96/22292 (1996), and in U.S. Pat. No. 5,780,471 (1998).

Albright et al. broadly disclose tricyclic benzazepine vasopressin antagonists in WO 96/22282A1 (1996) which possess antagonistic activity at the $V_1$ and/or $V_2$ receptors and exhibit in vivo vasopressin antagonistic activity, as well as antagonistic activity at the oxytocin receptors.

SUMMARY OF THE INVENTION

This invention relates to novel compounds selected from those of Formula (I):

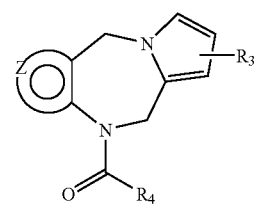

wherein:

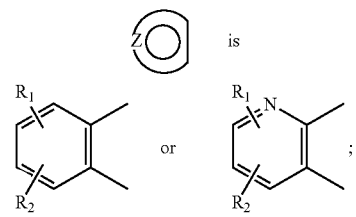

$R_1$ and $R_2$ are, independently, selected from hydrogen, $(C_1-C_6)$lower alkyl, halogen, cyano, trifluoromethyl, hydroxy, amino, $(C_1-C_6)$ lower alkylamino, $(C_1-C_6)$ lower alkoxy, —$OCF_3$, —$(C_1-C_6)$ lower alkoxycarbonyl, —NHCO[lower alkyl], carboxy, —$CONH_2$, —CONH $(C_1-C_6)$ lower alkyl, or —CON[$(C_1-C_6)$ lower alkyl]$_2$;

$R_3$ is a substituent selected from hydrogen, $(C_1-C_6)$ lower alkyl, $(C_1-C_6)$ lower alkoxy, hydroxy, amino, $(C_1-C_6)$ lower alkylamino, —CO lower alkyl $(C_1-C_6)$, or halogen;

$R_4$ consists of the moiety B-C;

wherein B is selected from the group of

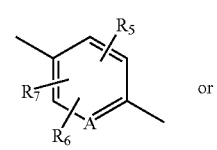

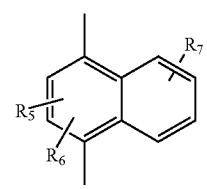

and C is defined as:

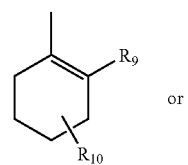

-continued (d)

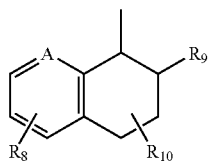

wherein:

A is CH or N;

R₅, R₆, R₇ and R₈ are independently, selected from hydrogen, (C₁–C₆) lower alkyl, (C₁–C₆) lower alkoxy, hydroxy (C₁–C₆) lower alkyl, alkoxy (C₁–C₆) lower alkyl, acyloxy (C₁–C₆) lower alkyl, (C₁–C₆) lower alkylcarbonyl, (C₃–C₆) lower alkenyl, (C₃–C₆) lower alkynyl, (C₃–C₈) cycloalkyl, formyl, cycloalkylcarbonyl, carboxy, alkoxycarbonyl, cycloalkyloxycarbonyl, aryl alkyloxycarbonyl, carbamoyl, —O—CH₂—CH=CH₂, halogen, halo lower alkyl, trifluoromethyl, —OCF₃, —S(lower alkyl), —OC(O)N[lower alkyl]₂, —CONH(lower alkyl), —CON[lower alkyl]₂, lower alkylamino, di-lower alkylamino, lower alkyl di-lower alkylamino, hydroxy, cyano, trifluoromethylthio, nitro, amino, lower alkylsulfonyl, aminosulfonyl, lower alkylaminosulfonyl, naphthyl, phenyl, or

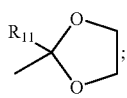

R₉ is chosen from the group of hydrogen, (C₁–C₆) lower alkyl, hydroxy (C₁–C₆) lower alkyl, alkoxy (C₁–C₆) lower alkyl, acyloxy (C₁–C₆) lower alkyl, alkoxycarbonyl, —CON[(C₁–C₆) lower alkyl]₂, cyano; or aryl, optionally substituted by halogen, or lower alkoxy;

R₁₀ represents one to two substituents chosen independently, from the group of hydrogen, (C₁–C₆) lower alkyl, hydroxy (C₁–C₆) lower alkyl, alkoxy (C₁–C₆) lower alkyl, acyloxy (C₁–C₆) lower alkyl, [(C₁–C₆) lower alkyl]₂, carbonyl,

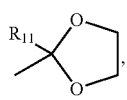

azido, amino, —NH[lower alkyl], —N[lower alkyl]₂, amino carbonyl lower alkyl, phthalimido, cyano, halogen, thio lower alkyl, aryloxy, arylthio, aryl optionally substituted with one to three substituents chosen from (C₁–C₆) lower alkyl, alkoxy or halogen; hydroxy, lower alkoxy, —OSO₂R₁₂, or OP' wherein P' is tert-butyl dimethylsilyl, tert-butyl diphenylsilyl, carbonyl loweralkyl, carbonyl trifluoro lower alkyl, aryl lower alkyl, arylcarbonyl, methoxymethyl, or methylthiomethyl; with the proviso that when R₁₀ represents two substituents, the two substituents may be joined together to form with the cyclohexene ring to which they are attached a bicyclic system including but not limited to bicyclo[3.2.1]oct-2-ene, or (6,6-dimethyl)-bicyclo[3.1.1]hept-2-ene;

R₁₁ is selected from the group of hydrogen, or (C₁–C₆) lower alkyl;

R₁₂ is selected from the group of (C₁–C₆) lower alkyl, trifluoro lower alkyl, or aryl optionally substituted by halogen or lower alkyl;

and the pharmaceutically acceptable salts, or pro-drug forms thereof.

One group of compounds of this invention include those of formula (I), above, wherein:

 is

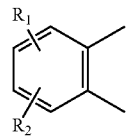 or 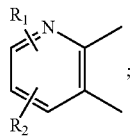;

R₁ and R₂ are, independently, selected from hydrogen, C₁–C₆ alkyl, halogen, cyano, trifluoromethyl, hydroxy, amino, C₁–C₆ alkylamino, C₁–C₆ alkoxy, —OCF₃, —(C₁–C₆) alkoxycarbonyl, —NHCO[C₁–C₆ alkyl], carboxy, —CONH₂, —CONH—(C₁–C₆ alkyl), or —CON[C₁–C₆ alkyl]₂;

R₃ is a substituent selected from hydrogen, C₁–C₆ alkyl, C₁–C₆ alkoxy, hydroxy, amino, C₁–C₆ alkylamino, —CO-alkyl (C₁–C₆), or halogen;

R₄ consists of the moiety B-C;

wherein B is selected from the group of (a)

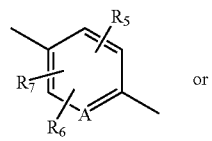

or (b)

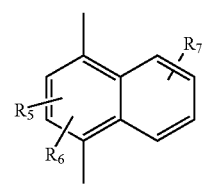

and C is defined as:

(c)

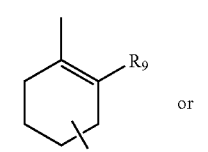

or (d)

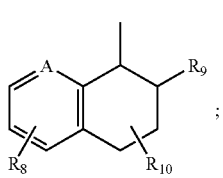

wherein:

A is CH;

R₅, R₆, R₇ and R₈ are independently selected from hydrogen, (C₁–C₆) lower alkyl, (C₁–C₆) lower alkoxy, hydroxy ($C_1$–$C_6$) lower alkyl, alkoxy ($C_1$–$C_6$) lower alkyl, acyloxy ($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, carbamoyl, —O—$CH_2$—CH=$CH_2$, halogen, halo lower alkyl, trifluoromethyl, —$OCF_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, or lower alkylaminosulfonyl;

$R_9$ is chosen from the group of hydrogen, $C_1$–$C_6$ alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, cyano; or phenyl optionally substituted by halogen, or $C_1$–$C_6$ alkoxy;

$R_{10}$ represents one to two substituents chosen independently, from the group of hydrogen, ($C_1$–$C_6$) lower alkyl, hydroxy ($C_1$–$C_6$) lower alkyl, alkoxy ($C_1$–$C_6$) lower alkyl, acyloxy ($C_1$–$C_6$) lower alkyl, [($C_1$–$C_6$) lower alkyl]$_2$, carbonyl, azido, amino, —NH[lower alkyl], —N[lower alkyl]$_2$, amino carbonyl lower alkyl, phthalimido, cyano, halogen, thio lower alkyl; hydroxy, lower alkoxy, —$OSO_2R_{12}$, or OP' wherein P' is tert-butyl dimethylsilyl, tert-butyl diphenylsilyl, carbonyl loweralkyl, carbonyl trifluoro $C_1$–$C_6$ alkyl, methoxymethyl, or methylthiomethyl; with the proviso that when $R_{10}$ represents two substituents, the two substituents may be joined together to form with the cyclohexene ring to which they are attached a bicyclic system such as bicyclo[3.2.1]oct-2-ene, or (6,6-dimethyl)-bicyclo[3.1.1]hept-2-ene;

$R_{12}$ is selected from the group of $C_1$–$C_6$ alkyl, or trifluoro $C_1$–$C_6$ alkyl;

or a pharmaceutically acceptable salt or pro-drug form thereof.

As used herein the term "lower", as used in relation to alkoxy or alkyl, is understood to refer to those groups having from 1 to 6 carbon atoms. Halogen refers to fluorine, chlorine, bromine or iodine.

Among the preferred compounds of this invention include:

10-(5-Chloro-4-cyclohex-1-en-1-yl-2-methoxybenzoyl)-10,11-dihydro-5H-pyrrolo[2,1-c][1,4]benzodiazepine;

(10,11-Dihydro-5H-pyrrolo[2,1-c][1,4]benzodiazepin-10-yl)-(4-cyclohex-1-en-1-yl-3-methyl-phenyl)-methanone;

(10,11-Dihydro-5H-pyrrolo[2,1-c][1,4]benzodiazepin-10-yl)-[4-(3,4-dihydro-naphthalen-1-yl)-3-methyl-phenyl]-methanone;

3-[2-Methyl-4-(5H-pyrrolo[2,1-c][1,4]benzodiazepin-10(11H)-yl-carbonyl)phenyl]-2-methyl-cyclohex-2-en-1-one;

(10,11-Dihydro-5H-pyrrolo[2,1-c][1,4]benzodiazepin-10-yl)-[4-(3-hydroxy-2-methyl-cyclohex-1-en-1-yl)-3-methyl-phenyl]-methanone;

(10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone;

(10,11-Dihydro-5H-pyrrolo[2,1-c][1,4]benzodiazepin-10-yl)-[4-(2-methyl-cyclohex-1-en-1-yl)-phenyl]-methanone;

10-[5-Chloro-4-(3,4-dihydro-naphthalen-1-yl)-2-methoxybenzoyl]-10,11-dihydro-5H-pyrrolo[2,1-c][1,4]benzodiazepine;

3-[2-Chloro-5-methoxy-4-(5H-pyrrolo[2,1-c][1,4]benzodiazepin-10(11H)-yl-carbonyl)phenyl]-2-methyl-cyclohex-2-en-1-one;

(10,11-dihydro-5H-pyrrolo[2,1-c][1,4]benzodiazepin-10-yl)-[2-chloro-4-(cyclohex-1-en1-yl)-phenyl]-methanone (10,11-Dihydro-5H-pyrrolo[2,1-c][1,4]benzodiazepin-10-yl)-[2-chloro-4-(3,4-dihydro-naphthalen-1-yl)-phenyl]-methanone;

(10,11-Dihydro-5H-pyrrolo[2,1-c][1,4]benzodiazepin-10-yl)-[2-chloro-4-(6,6-dimethyl-cyclohex-1-en-1-yl)-phenyl]-methanone;

(10,11-Dihydro-5H-pyrrolo[2,1-c][1,4]benzodiazepin-10-yl)-[2-chloro-4-(2-methyl-3-oxo-cyclohex-1-en-1-yl)-phenyl]-methanone;

(10,11-Dihydro-5H-pyrrolo[2,1-c][1,4]benzodiazepin-10-yl)-[2-chloro-4-(3-hydroxy-2-methyl-cyclohex-1-en-1-yl)-phenyl]-methanone;

(10,11-Dihydro-5H-pyrrolo[2,1-c][1,4]benzodiazepin-10-yl)-(4-cyclohex-1-en-1-yl-phenyl)-methanone;

(10,11-Dihydro-5H-pyrrolo[2,1-c][1,4]benzodiazepin-10-yl)-[4-(6-methyl-cyclohex-1-en-1-yl)-phenyl]-methanone;

(10,11-Dihydro-5H-pyrrolo[2,1-c][1,4]benzodiazepin-10-yl)-[4-(6,6-dimethyl-cyclohex-1-en-1-yl)-phenyl]-methanone;

(10,11-Dihydro-5H-pyrroio[2,1-c][1,4]benzodiazepin-10-yl)-[4-(3,4-dihydro-naphthalen-1-yl)-phenyl]-methanone;

(10,11-Dihydro-5H-pyrrolo[2,1-c][1,4]benzodiazepin-10-yl)-[4-(2,6-dimethyl-cyclohex-1-en-1-yl)-phenyl]-methanone;

(10,11-5H-Dihydro-pyrrolo[2,1-c][1,4]benzodiazepin-10-yl)-[4-(6-tert-butyl-cyclohex-1-en-1-yl)-phenyl]-methanone;

(10,11-Dihydro-5H-pyrrolo[2,1-c][1,4]benzodiazepin-10-yl)-(4-bicyclo[3.2.1]oct-2-en-2-yl-phenyl)-methanone;

(10,11-Dihydro-5H-pyrrolo[2,1-c][1,4]benzodiazepin-10-yl)-[4-(6,6-dimethyl-bicyclo[3.1.1]hept-2-en-2-yl)-phenyl]-methanone;

(10,11-Dihydro-5H-pyrrolo[2,1-c][1,4]benzodiazepin-10-yl)-[4-(3,3,5,5-tetramethyl-cyclohex-1-en-1-yl)-phenyl]-methanone;

3-[4-(10,11-Dihydro-5H-pyrrolo[2,1-c][1,4]benzodiazepine-10-carbonyl)-phenyl]-cyclohex-2-en-1-one;

(10,11-Dihydro-5H-pyrrolo[2,1-c][1,4]benzodiazepin-10-yl)-[4-(3-hydroxy-cyclohex-1-en-1-yl)-phenyl]-methanone;

3-[4-(10,11-Dihydro-5H-pyrrolo[2,1-c][1,4]benzodiazepine-10-carbonyl)-phenyl]-2-methyl-cyclohex-2-en-1-one;

(10,11-Dihydro-5H-pyrrolo[2,1-c][1,4]benzodiazepin-10-yl)-[4-(3-hydroxy-2-methyl-cyclohex-1-en-1-yl)-phenyl]-methanone;

(10,11-Dihydro-5H-pyrrolo[2,1-c][1,4]benzodiazepin-10-yl)-[3-methyl-4-(6-methyl-cyclohex-1-en-1-yl)-phenyl]-methanone;

(10,11-Dihydro-5H-pyrrolo[2,1-c][1,4]benzodiazepin-10-yl)-[4-(6,6-dimethyl-cyclohex-1-en-1-yl)-3-methyl-phenyl]-methanone;

(10,11-Dihydro-5H-pyrrolo[2,1-c][1,4]benzodiazepin-10-yl)-[4-(3,4-dihydro-naphthalen-1-yl)-3-methyl-phenyl]-methanone;

(10,11-Dihydro-5H-pyrrolo[2,1-c][1,4]benzodiazepin-10-yl)-[4-(2,6-dimethyl-cyclohex-1-en-1-yl)-3-methyl-phenyl]-methanone;

(10,11-Dihydro-5H-pyrrolo[2,1-c][1,4]benzodiazepin-10-yl)-[4-(6-tert-butyl-cyclohex-1-en-1-yl)-3-methyl-phenyl]-methanone;
(10,11-Dihydro-5H-pyrrolo[2,1-c][1,4]benzodiazepin-10-yl)-(4-bicyclo[3.2.1]oct-2-en-2-yl-3-methyl-phenyl)-methanone;
(10,11-Dihydro-5H-pyrrolo[2,1-c][1,4]benzodiazepin-10-yl)-[4-(6,6-dimethyl-bicyclo[3.1.1]hept-2-en-2-yl)-3-methyl-phenyl]-methanone;
(10,11-Dihydro-5H-pyrrolo[2,1-c][1,4]benzodiazepin-10-yl)-[3-methyl-4-(3,3,5,5-tetramethyl-cyclohex-1-en-1-yl)-phenyl]-methanone;
(10,11-Dihydro-5H-pyrrolo[2,1-c][1,4]benzodiazepin-10-yl)-{4-[2-(3-methoxy-phenyl)-cyclohex-1-en-1-yl]-3-methyl-phenyl}-methanone;
3-[4-(10,11-Dihydro-5H-pyrrolo[2,1-c][1,4]benzodiazepine-10-carbonyl)-2-methyl-phenyl]-cyclohex-2-en-1-one;
(10,11-Dihydro-5H-pyrrolo[2,1-c][1,4]benzodiazepin-10-yl)-[4-(3-hydroxy-cyclohex-1-en-1-yl)-3-methyl-phenyl]-methanone;
(10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone;
(10,11-Dihydro-5H-pyrrolo-[2,1-c][1,4]benzodiazepin-10-yl)-[4-((3S)-3-hydroxy-2-methyl-cyclohex-1-en-1-yl)-3-methyl-phenyl]-methanone;
10-{4-[(3R)-3-Methoxy-2-methylcyclohex-1-en-1-yl]-3-methylbenzoyl}-10,11-dihydro-5H-pyrrolo[2,1-c][1,4]benzodiazepine;
[4-(3-Azido-2-methyl-cyclohex-1-en-1-yl)-3-methyl-phenyl]-(10,11-dihydro-5H-pyrrolo[2,1-c][1,4]benzodiazepin-10-yl)-methanone;
[4-(3-Amino-2-methyl-cyclohex-1-en-1-yl)-3-methyl-phenyl]-(10,11-dihydro-5H-pyrrolo[2,1-c][1,4]benzodiazepin-10-yl)-methanone;

It is understood by those practicing the art that some of the compounds of this invention depending on the definition of $R_1$, $R_2$, $R_3$, and $R_4$ may contain one or more asymmetric centers and may thus give rise to enantiomers and diastereomers. The present invention includes all stereoisomers including individual diastereomers and resolved, enantiomerically pure R and S stereoisomers; as well as racemates, and all other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, E/Z isomers, endo-exo isomers, and mixtures thereof which possess the indicated activity. Such isomers may be obtained in pure form by standard separation procedures known to those skilled in the art. It is understood also by those practicing the art that some of the compounds of this invention depending on the definition of $R_5$, $R_6$, $R_7$, $R_9$ and $R_{10}$ may be chiral due to hindered rotation, and give rise to atropisomers which can be resolved and obtained in pure form by standard procedures known to those skilled in the art. Also included in the present invention are all polymorphs and hydrates of the compounds of the present invention.

DETAILED DESCRIPTION OF THE INVENTION

The present invention comprises the compounds described above, as well as pharmaceutical compositions comprising the compounds of this invention in combination or association with one or more pharmaceutically acceptable carriers or excipients. In particular, the present invention provides a pharmaceutical composition which comprises a therapeutically or pharmaceutically effective amount of one or more compounds of this invention and a pharmaceutically acceptable carrier or excipient.

This invention also comprises methods for treating, inhibiting or preventing conditions in a mammal, preferably in a human, where decreased vasopressin effects are desired, such as in congestive heart failure, in disease conditions with excessive renal water reabsorption and in conditions with increased vascular resistance and coronary vasoconstriction.

Also according to the present invention there is provided a method of treating, preventing or inhibiting disorders which are remedied or alleviated by vasopressin agonist activity including, but not limited to, diabetes insipidus, nocturnal enuresis, nocturia, urinary incontinence, or bleeding and coagulation disorders,. This invention also provides a method for inducing temporary delay of urination whenever desirable in humans and other mammals, the method comprising administering to a recipient in need thereof a pharmaceutically or therapeutically effective amount of a compound of this invention.

This invention also comprises methods for treating conditions in a mammal, preferably a human, which are remedied or alleviated by oxytocin antagonist activity including, but not limited to, treatment or prevention of preterm labor, dysmenorrhea and suppressing labor prior to caesarian delivery whenever desirable in a mammal, preferably in a human. The methods comprise administering to a mammal in need thereof a therapeutically effective amount of one or more of the compounds of this invention.

The present invention also comprises combinations of the compounds of the present invention with one or more agents useful in the treatment of disorders such as congestive heart failure, in disease conditions with excessive renal water reabsorption and in conditions with increased vascular resistance and coronary vasoconstriction; in the treatment of disorders such as diabetes insipidus, nocturnal enuresis, nocturia, urinary incontinence, bleeding and coagulation disorders, or temporary delay of urination; and in the prevention and/or suppression of preterm labor or dysmenorrhea, and stopping labor prior to caesarian delivery. More specifically, the compounds of the present invention may be effectively administered in combination with effective amounts of other agents used in the treatment or prevention of congestive heart failure, excessive renal water reabsorption and in conditions with increased vascular resistance and coronary vasoconstriction, diabetes insipidus, nocturia, urinary incontinence, preterm labor, dysmenorrhea or suppressing labor prior to caesarean delivery including other vasopressin antagonists, vasopressin agonists, β-adrenergic agonists, calcium channel blockers, prostaglandin synthesis inhibitors, other oxytocin antagonists (e.g. atosiban), magnesium sulfate, ethanol, and other agents useful in the treatment of said disorders. The present invention is to be understood as embracing all simultaneous or alternating treatments of any combination of the compounds of the present invention with other tocolytic agents with any pharmaceutical composition useful for the treatment of preterm labor, dysmenorrhea, and suppressing labor prior to caesarean delivery in mammals.

The compositions are preferably adapted for intravenous (both bolus and infusion) and oral administration. However, they may be adapted for other modes of administration including subcutaneous, intraperitoneal, or intramuscular administration to a human or a farm animal in need of decreased levels of vasopressin, in need of vasopressin or a vasopressin agonist whenever the synthesis of vasopressin in the brain is defective, or in need of a tocolytic agent.

The compounds of the present invention can be used in the form of salts derived from non toxic pharmaceutically acceptable acids or bases. These salts include, but are not limited to, the following: salts with inorganic acids such as hydrochloric acid, hydrobromic acid, sulfuric acid, nitric acid, phosphoric acid and, as the case may be, such organic acids as acetic acid, oxalic acid, citric acid, tartaric acid, succinic acid, maleic acic, benzoic acid, benzene sulfonic acid, fumaric acid, malic acid, methane sulfonic acid, pamoic acid, and para-toluenesulfonic acid . Other salts include salts with alkali metals or alkaline earth metals, such as sodium, potassium, calcium or magnesium, or with organic bases including quaternary ammonium salts. The compounds can also be used in the form of esters, carbamates and other conventional prodrug forms, which in general, will be functional derivatives of the compounds of this invention which are readily converted to the active moiety in vivo. This is meant to include the treatment of the various conditions described hereinbefore with a compound of this invention or with a compound which is not specifically disclosed but which converts to a compound of this invention in vivo upon administration. Also included are metabolites of the compounds of the present invention defined as active species produced upon introduction of these compounds into a biological system.

When the compounds of this invention are employed for the above utilities, they may be combined with one or more pharmaceutically acceptable excipients or carriers, for example, solvents, diluents and the like, and may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredients employed may vary depending on the particular compound or salt employed, the mode of administration, age, weight, sex and medical condition of the patient, and the severity of the condition being treated. An ordinarily skilled physician, veterinarian or clinician can readily determine and prescribe the effective amount of the agent required to prevent, counter or arrest the progress of the condition. However, in general, satisfactory results are obtained when the compounds of the invention are administered at a daily dose of from about 0.5 to about 500 mg/Kg of mammal body weight, preferably given in divided doses two to four times a day, or in a sustained release form. For most large mammals the total daily dosage is from about 0.5 to 100 mg, preferably from 0.5 to 80 mg/Kg. Dosage forms suitable for internal use comprise from about 0.05 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, glycerol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol (e.g. glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally using transdermal skin patches known to those ordinarily skilled in the art. When using a transdermal delivery system, the dosage administration will be continuous rather than in a single or divided daily doses. The compounds of the present invention can also be administered in the form of liposome delivery system wherein the liposomal lipid bilayers are formed from a variety of phospholipids.

Compounds of the present invention may also be delivered by the use of carriers such as monoclonal antibodies to which the active compounds are coupled. The compounds of the present invention may also be coupled to soluble polymers as drug carriers or to biodegradable polymers useful in achieving controlled release of the active agent.

Also according to the present invention there are provided processes for producing the compounds of the present invention.

Process of the Invention

The compounds of the present invention may be prepared according to one of the general processes outlined below.

The compounds of general formula (I) wherein

$R_3$, and $R_4$ are defined hereinbefore, can be conveniently prepared as shown in Scheme I.

Scheme I

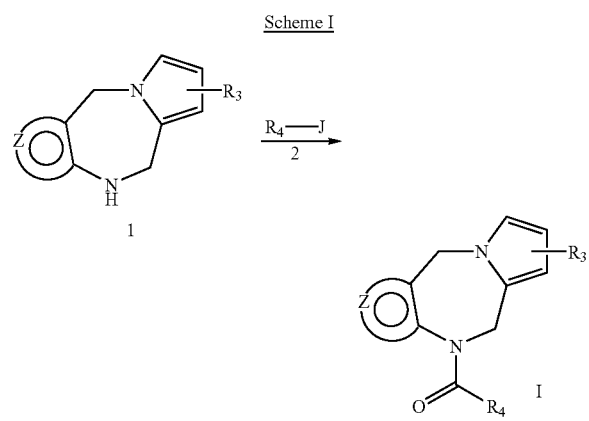

Thus, a tricyclic diazepine of formula (1) is treated with an appropriately substituted acylating agent such as an aroyl halide, preferably an appropriately substituted acyl chloride or bromide of formula (2, J=COCl or COBr) wherein $R_4$ is ultimately chosen on the basis of its compatibility with the present reaction scheme, in the presence of an inorganic base such as potassium carbonate, or in the presence of an organic base such as pyridine, 4-(dimethylamino)pyridine, or a tertiary amine such as triethylamine or N,N-diisopropylethyl amine in an aprotic solvent such as dichloromethane, N,N-dimethylformamide or tetrahydrofuran at temperatures ranging from –5° C. to 50° C. to provide intermediates of general formula (1) wherein $R_4$ is defined hereinbefore.

Alternatively, the acylating species of formula (2) can be a mixed anhydride of the corresponding carboxylic acid, such as that prepared by treating said acid with 2,4,6-trichlorobenzoyl chloride in an aprotic organic solvent such as dichloromethane according to the procedure of Inanaga et al., Bull. Chem. Soc. Jpn., 52, 1989 (1979). Treatment of said mixed anhydride of general formula (2) with a tricyclic diazepine of formula (1) in a solvent such as dichloromethane and in the presence of an organic base such as 4-(dimethylamino)pyridine, at temperatures ranging from 0° C. to the reflux temperature of the solvent, yields the desired acylated derivative (I) of Scheme I.

The acylating intermediate of formula (2) is ultimately chosen on the basis of its compatibility with the $R_4$ groups, and its reactivity with the tricyclic diazepine of formula (1).

The desired intermediates of formula (2) of Scheme I wherein $R_4$ consists of the moiety B-C wherein B is (a) and C is (c) can be conveniently prepared by a process shown in Scheme II. Thus, an appropriately substituted aryl(heteroaryl) iodide (bromide) of formula (3) wherein P is a carboxylic acid protecting group, preferably P=alkyl or benzyl, M=I or Br, and A, $R_5$, $R_6$ and $R_7$ are defined hereinbefore, is reacted with a tri(alkyl)tin(IV) derivative of formula (4, W=Sn(trialkyl)$_3$, preferably Sn(n-Bu)$_3$) wherein $R_9$, $R_{10}$ are ultimately chosen on the basis of their compatibility with the present reaction scheme, in the presence of a Pd(0) catalyst, in the presence or absence of inorganic salts (e.g. LiCl), in an aprotic solvent such as dioxane or N-methylpyrrolidinone, to provide the intermediate ester (5). Subsequent unmasking of the carboxylic acid by hydrolysis, hydrogenolysis or similar methods known in the art, followed by activation of the intermediate acid (6) provide the desired compounds of formula (7) wherein A, $R_5$, $R_6$, $R_7$, $R_9$ and $R_{10}$ are hereinbefore defined, suitable for coupling with the tricyclic diazepine of formula (1).

The desired intermediates of formula (2) of Scheme I wherein $R_4$ consists of the moiety B-C where B is (a) and C is (d) or B is (b) and C is either (c) or (d) can be prepared by a process analogous to that exemplified in Scheme II by replacing intermediates of formulas (3 and 4) with appropriately substituted naphthyl, dihydronaphthyl or dihydroquinolinyl intermediates.

Scheme II

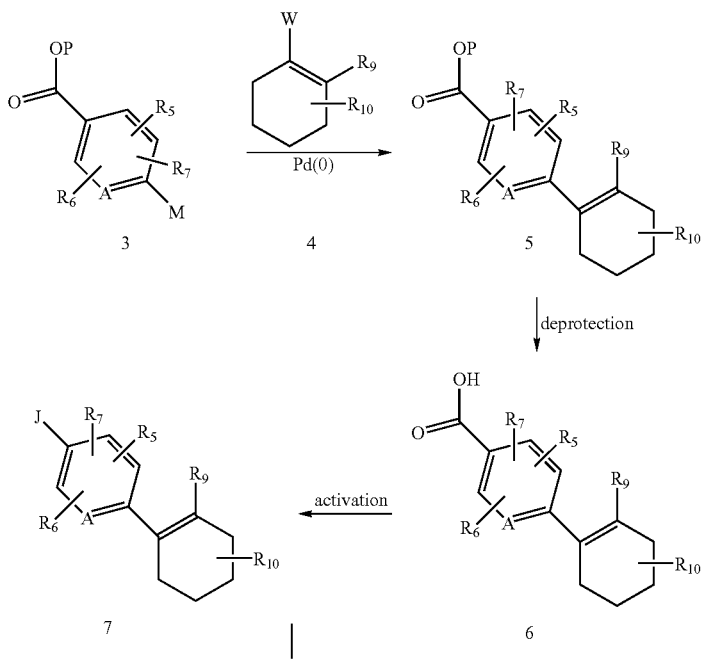

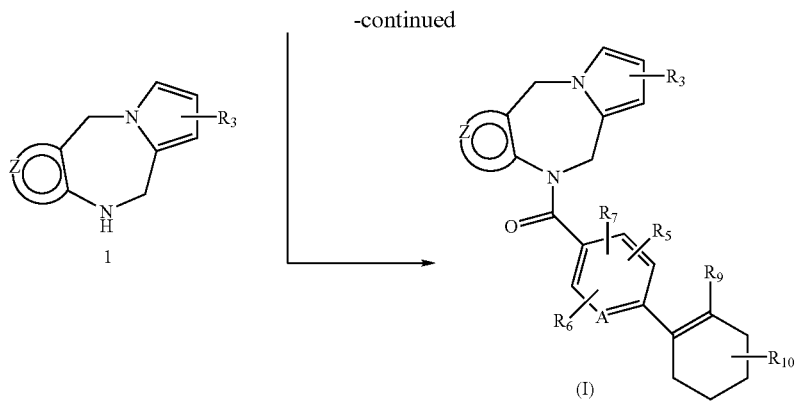

Alternatively, the desired intermediates of formula (5) of Scheme II wherein $R_4$ consists of the moiety B-C where B is (a) and C is (c) can be prepared by Suzuki coupling from the iodide(bromide, trifluoromethanesulfonate) (3, M=I, Br or OTf) and an appropriately substituted boron derivative of formula 4 (preferably, W=B(OH)$_2$) in the presence of a palladium catalyst such as palladium(II) acetate or tetrakis(triphenylphosphine) palladium(0) and an organic base such as triethylamine, or an inorganic base such as sodium (potassium or cesium) carbonate with or without added tetrabutylammonium bromide(iodide), in a mixture of solvents such as toluene-ethanol-water, acetone-water, water or water-acetonitrile at temperatures ranging from ambient to the reflux temperature of the solvent (Suzuki, *Pure & Appl. Chem.* 66, 213–222 (1994), Badone et al., *J. Org. Chem.* 62, 7170–7173 (1997)). The exact conditions for the Suzuki coupling of the halide and the boronic acid intermediates are chosen on the basis of the nature of the substrate and the substituents. The desired intermediates of formula (5) of Scheme II can be similarly prepared from the bromide (3, M=Br) and the boronic acid (4) in a solvent such as dioxane, N,N-dimethylformamide or dimethylsulfoxide, in the presence of potassium phosphate and a Pd(0) catalyst.

Alternatively, a cross coupling reaction of an iodide (bromide, or trifluoromethanesulfonate) of formula (4, W=Br, I, OTf) with a bis(pinacolato)diboron [boronic acid, or trialkyl tin(IV)] derivative of formula (3, M=

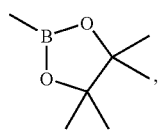

B(OH)$_2$, or SnBu$_3$) yields the desired intermediate of formula (5) which is converted to (I) in the manner of Scheme II.

The desired intermediates of formula (5) of Scheme II wherein $R_4$ consists of the moiety B-C wherein B is (a) and C is (d) or B is (b) and C is either (c) or (d) can be prepared in analogous fashion by replacing intermediates of formulas (3 and 4) with appropriately substituted naphthyl, dihydronaphthyl, or dihydroquinolyl intermediates.

The required appropriately substituted aryl(heteroaryl) halides of formula (3, M=Br or I) of Scheme II are either available commercially, or are known in the art or can be readily accessed in quantitative yields and high purity by diazotization of the corresponding substituted anilines (3, P=H, alkyl or benzyl, M=NH$_2$) followed by reaction of the intermediate diazonium salt with iodine and potassium iodide in aqueous acidic medium essentially according to the procedures of Street et al,. *J. Med. Chem.* 36, 1529 (1993) and Coffen et al., *J. Org. Chem.* 49, 296 (1984) or with copper(I) bromide, respectively (March, *Advanced Organic Chemistry*, 3$^{rd}$ Edn., p.647–648, John Wiley & Sons, New York (1985).

Alternatively, the desired intermediates of formula (6, A=CH) of Scheme II wherein $R_4$ consists of the moiety B-C wherein B is (a, A=CH) and C is (c) can be conveniently prepared as shown in Scheme III by cross-coupling reaction of an appropriately substituted pinacolato borane of formula (10) wherein $R_9$, $R_{10}$ are ultimately chosen on the basis of their compatibility with the present reaction scheme, with an aryl triflate of formula (11, Y=OTf) or an aryl halide (11, Y=Br, I) wherein $R_5$, $R_6$ and $R_7$ are defined hereinbefore, according to the general procedures of Ishiyama et al., *Tetr. Lett.* 38, 3447–3450 (1997) and Giroux et al. *Tetr. Lett.* 38, 3841–3844 (1997), followed by basic or acidic hydrolysis of the intermediate nitrile of formula (12) (cf. March, *Advanced Organic Chemistry*, 3$^{rd}$ Edn., John Wiley & Sons, New York, p. 788 (1985)).

Scheme III

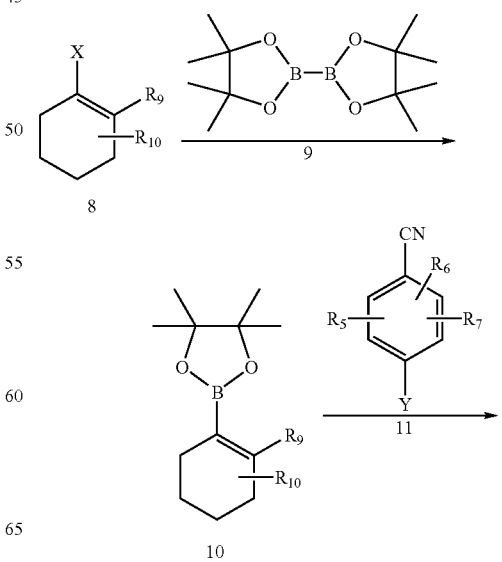

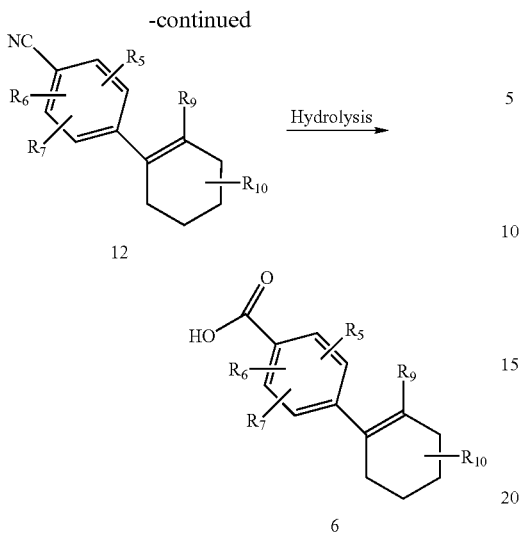

12

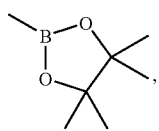

6

Alternatively, reaction of an iodide (bromide, or trifluoromethanesulfonate) of formula (8, X=Br, I, or OTf) with a bis(pinacolato)diboron [boronic acid or trialkyl tin(IV)] derivative of formula (11, Y=

B(OH)$_2$, or SnBu$_3$) yields the desired intermediate of formula (12) which is converted to (6) in the manner of Scheme III.

The desired intermediates of formula (6) of Scheme II wherein R$_4$ consists of the moiety B-C wherein B is (a), A=CH) and C is (d) or B is (b) and C is either (c) or (d, A=CH), can be prepared in analogous fashion by replacing intermediates of formulas (10 and 11) with appropriately substituted naphthyl or dihydronaphthyl intermediates.

The desired boronic esters of formula (10) of Scheme III can be conveniently prepared by the palladium-catalyzed cross-coupling reaction of the pinacol ester of diboronic acid (9) with an appropriately substituted alkenyl halide preferably a bromide or iodide (8, X=Br, I) or alkenyl trifluoromethanesulfonate (8, X=OTf) according to the described procedures of Ishiyama et al., *J. Org. Chem.* 60, 7508–7510 (1995) and Giroux et al., *Tetr. Lett.* 38, 3841–3844 (1997).

The desired compounds of formula (I) of Scheme II wherein R$_4$ consists of the moiety B-C wherein B is (a) and C is (c) can be alternatively prepared by a process shown in Scheme IV.

Scheme IV

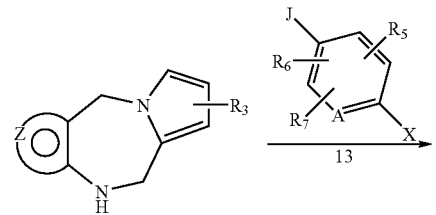

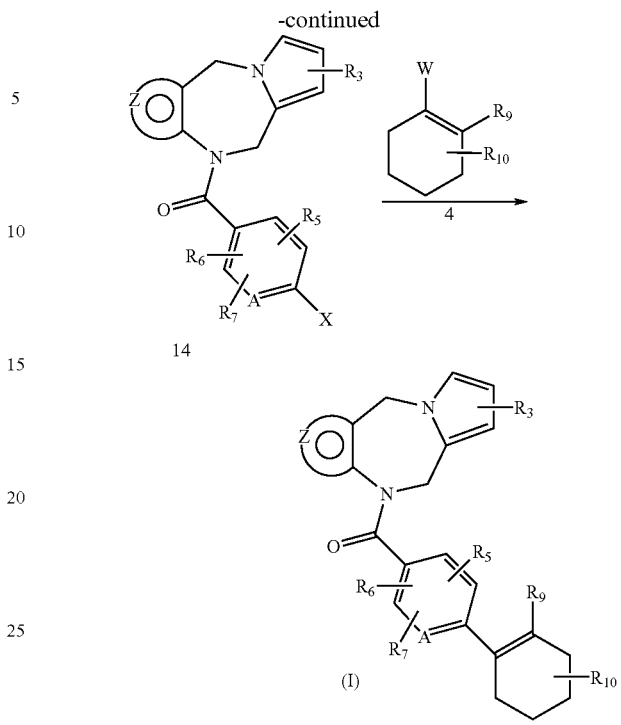

Thus, a tricyclic diazepine of formula (1) is treated with an appropriately substituted acylating agent such as a halo aroyl(heteroaroyl) halide, preferably an iodo(bromo) aroyl (heteroaroyl) chloride(bromide) of formula (13, J=COCl or COBr; X=I, Br) wherein R$_5$, R$_6$ and R$_7$ are hereinbefore defined, using any of the procedures hereinbefore described to provide the acylated intermediate of general formula (14) of Scheme IV.

Alternatively, the acylating species of formula (13) can be a mixed anhydride of the corresponding carboxylic acid. Treatment of said mixed anhydride of general formula (13) with a tricyclic diazepine of formula (1) according to the procedure described hereinbefore yields the intermediate acylated derivative (14).

The acylating intermediate of formula (13) is ultimately chosen on the basis of its compatibility with A and the R$_5$, R$_6$ and R$_7$ groups, and its reactivity with the tricyclic benzodiazepine of formula (1).

A Stille coupling reaction of (14, X=I) with an appropriately substituted organotin reagent such as a trialkyltin(IV) derivative, preferably a tri-n-butyltin(IV) derivative of formula (4, W=SnBu$_3$) wherein R$_9$, R$_{10}$ are ultimately chosen on the basis of their compatibility with the present reaction scheme, in the presence of a catalyst such as tetrakis (triphenylphosphine) palladium (0) in an aprotic organic solvent such as toluene or N,N-dimethylformamide at temperatures ranging from ambient to 150° C. (cf. Farina et al., *J. Org. Chem,* 59, 5905 (1994) and references cited therein) affords the desired compounds of formula (I) wherein

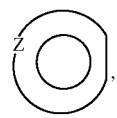

A, R$_3$, R$_5$, R$_6$, R$_7$, R$_9$ and R$_{10}$ are as defined hereinbefore.

Alternatively, reaction of a compound of formula (14, X=Cl, Br or I) with an appropriately substituted boronic acid of formula (4, W=B(OH)$_2$) wherein R$_9$, R$_{10}$ are chosen on the basis of their compatibility with the reaction scheme, in a mixture of solvents such as toluene-ethanol-water, and in the presence of a Pd(0) catalyst, and a base such as sodium carbonate, at temperatures ranging from ambient to the reflux temperature of the solvent, yields the desired compounds of formula (I) wherein

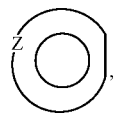

A, R$_3$, R$_5$, R$_6$, R$_7$, R$_9$ and R$_{10}$ are as defined hereinbefore.

Alternatively, a cross-coupling reaction of a compound of formula (14, X=Br or I) with a bis(pinacolato) diboron of formula (9) in the presence of a catalyst such as dichloro-[1,1'-bis(diphenylphosphino)ferrocene]palladium(II) dichloromethane adduct and potassium acetate, in an aprotic solvent such as dimethylsulfoxide, at temperatures ranging from ambient to 100° C., yields the intermediate of formula (14, X=

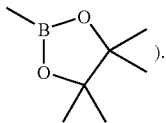

).

Subsequent reaction of (14) with an appropriately substituted trifluoromethanesulfonate of formula (4, W=OTf) in the presence of a base such as aqueous sodium carbonate, in an aprotic solvent such as N,N-dimethylformamide, at temperatures ranging from ambient to the reflux temperature of the solvent, provides the desired compounds of formula (1) wherein

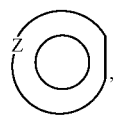

A, R$_3$, R$_5$, R$_6$, R$_7$, R$_9$, and R$_{10}$ are as defined hereinbefore.

The preferred substituted aroyl(heteroaroyl) chlorides (bromides) of formula (13) of Scheme IV (X=I, Br; J=COCl or COBr) wherein A, R$_5$, R$_6$ and R$_7$ are as defined hereinbefore, are either available commercially, or are known in the art, or can be readily prepared by procedures analogous to those in the literature for the known compounds.

The intermediates of formula (4, W=Sn(alkyl)$_3$, alkyl n-butyl) of Scheme IV are either commercially available or can be conveniently prepared as shown in Scheme V from the corresponding bromo starting materials of formula (15) wherein R$_9$, R$_{10}$ are ultimately chosen on the basis of their compatibility with the reaction scheme, by first reacting them with n-butyl lithium followed by reaction of the intermediate lithiated species with a trialkyl (preferably trimethyl or tri-n-butyl) tin(IV) chloride.

Scheme V

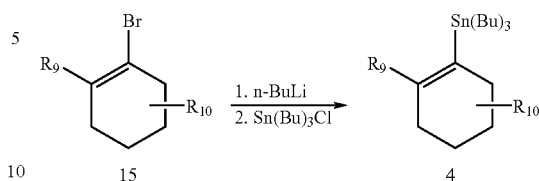

The preferred substituted boronic acids of formula (4, W=B(OH)$_2$) are either available commercially, or are known in the art, or can be readily prepared by procedures analogous to those in the literature for the known compounds.

The desired compounds of formula (I) of Scheme IV wherein R$_4$ consists of the moiety B-C wherein B is (a) and C is (d) or B is (b) and C is either (c) or (d) can be prepared in analogous fashion by replacing intermediates of formulas (13 and 4) with appropriately substituted naphthyl, dihydronaphthyl or dihydroquinolinyl intermediates.

Alternatively, as shown in Scheme VI, the appropriately substituted aroyl(heteroaroyl) halides, preferably aroyl(heteroaroyl) chlorides of formula (16, J=COCl) where A, R$_5$, R$_6$ and R$_7$ are hereinbefore defined, are reacted with a tricyclic diazepine of formula (1) to provide the intermediate bromides of formula (17). Subsequent reaction of (17) with a bis-alkyl-tin reagent (preferably bis-(tri-n-butyl)-tin(IV)) in the presence of a Pd(0) catalyst such as tetrakis(triphenylphosphine)-palladium(0) and lithium chloride, provides the stannane intermediate of formula (18). Further reaction of the tri-n-butyl tin(IV) derivative (18) with the appropriately substituted alkenyl halide of formula (19, M=Br or I) wherein R$_9$, R$_{10}$ are ultimately chosen on the basis of their compatibility with the present reaction scheme, in the presence of a Pd(0) catalyst such as tetrakis(triphenylphosphine) palladium(0), yields the desired compounds of formula (I) wherein R$_4$ consists of the moiety B-C wherein B is (a) and C is (c), and

A and R$_5$, R$_6$, R$_7$, R$_9$ and R$_{10}$ are defined hereinbefore.

Scheme VI

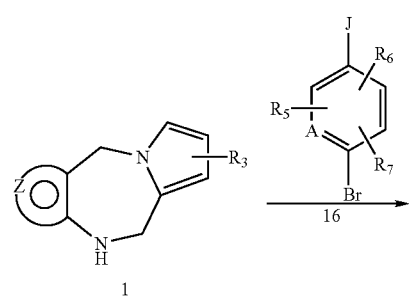

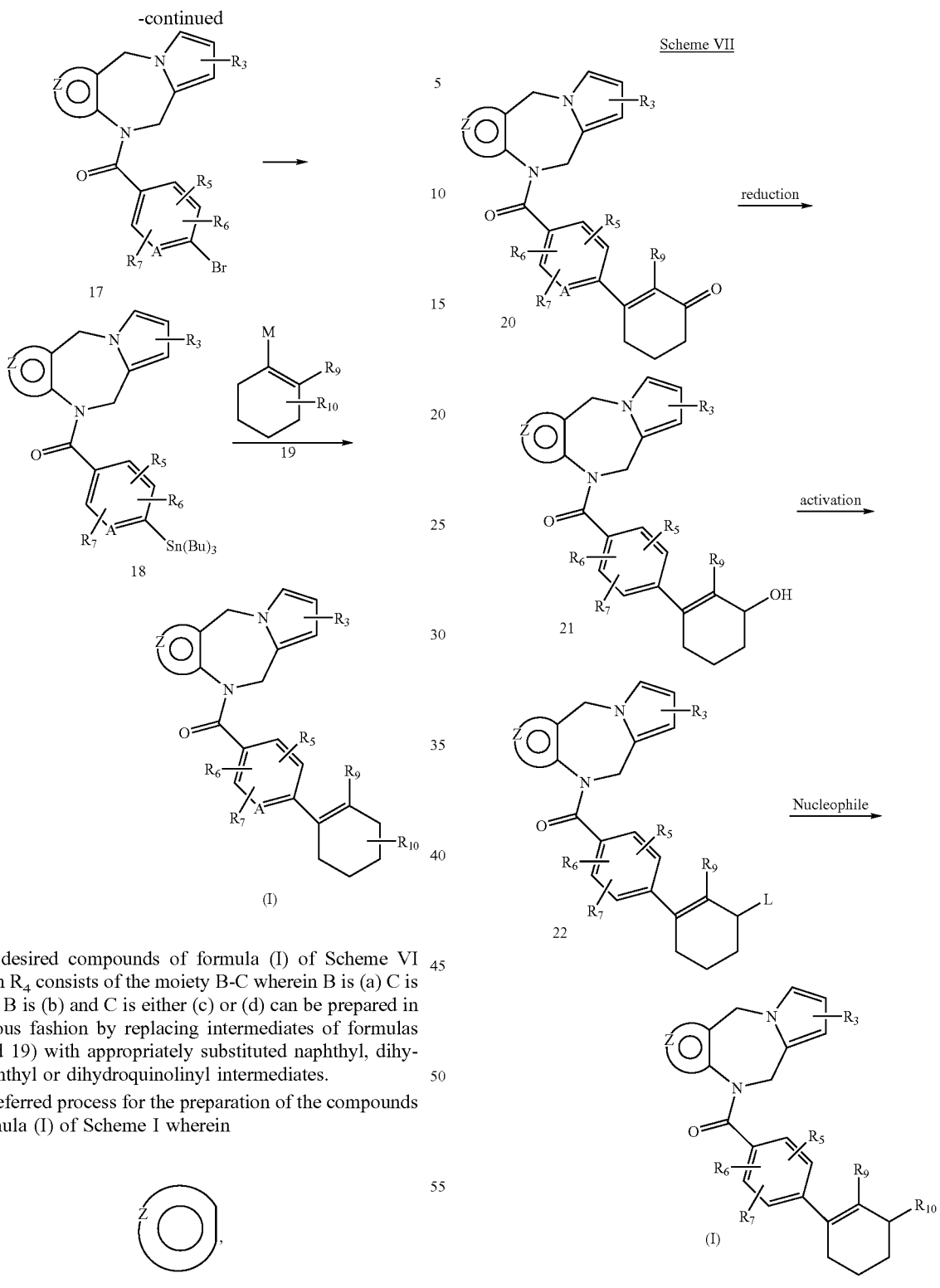

The desired compounds of formula (I) of Scheme VI wherein R₄ consists of the moiety B-C wherein B is (a) C is (d) and B is (b) and C is either (c) or (d) can be prepared in analogous fashion by replacing intermediates of formulas (16 and 19) with appropriately substituted naphthyl, dihydronaphthyl or dihydroquinolinyl intermediates.

A preferred process for the preparation of the compounds of formula (I) of Scheme I wherein $R_3$, $R_5$, $R_6$, and $R_7$ are defined hereinbefore, and $R_4$ consists of the moiety B-C wherein B is (a, A=CH) and C is (c), wherein $R_9$ is defined hereinbefore, and $R_{10}$ is hydroxy, alkoxy, OP', azido, phthalimido, cyano, phenoxy, thiophenoxy, thioalkyl, and related nucleophiles, is shown in Scheme VII.

Thus, an appropriately substituted diazepine cyclohexenone of formula (20) is converted to the corresponding cyclohexenol (21) by reduction with a metal hydride preferably sodium borohydride in the presence of cerium (III) chloride in an hydroxylic solvent such as methanol at temperatures ranging from −78° C. to ambient. The hydroxy function of (21) is then activated by conversion to a leaving group (22, L=leaving group) preferably a para-toluenesulfonate, methanesulfonate, trifluoromethanesulfonate, phosphate and the like. $S_N2$ displacement of the leaving group with a nucleophile such as azide, phthalimide, cyanide, halide, phenol, carbon or sulfur nucleophiles and the like, provides the desired compound (I) wherein

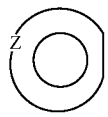

and $R_3$ are defined hereinbefore, and $R_4$ consists of the moiety B-C wherein B is (a, A=CH) and C is (c) and $R_5$, $R_6$, $R_7$, $R_9$ and $R_{10}$ are defined hereinbefore.

Alternatively, the racemic cyclohexenol of formula (21) is separated by chiral HPLC into its respective enantiomers of formulas (23) and (24) according to Scheme VIII. Each enantiomer can then be individually activated and subjected to $S_N2$ displacement with a nucleophile in the manner of Scheme VII.

Alternatively, the chiral cyclohexenols of formula (23) and (24) are obtained by asymmetric reduction of the cyclohexenone of formula (20) with a borane-tetrahydrofuran complex in an aprotic solvent such as tetrahydrofuran in the presence of a chiral auxiliary such as (S)-tetrahydro-1-methyl-3,3-diphenyl-1H,3H-pyrrolo[1,2-c][1,3,2]oxazaborole or (R)-tetrahydro-1-methyl-3,3-diphenyl-1H,3H-pyrrolo[1,2-c][1,3,2]oxazaborole respectively, at ambient temperature.

The subject compounds of the present invention were tested for biological activity according to the following procedures.

Vasopressin Binding in Chinese Hamster Ovary Cell Membranes Expressing Human Vasopressin $V_{1a}$ Subtype Receptors Receptor source:

Chinese hamster ovary cells (CHO cells) stably transfected with the human vasopressin $V_{1a}$ subtype receptors were either obtained from Biosignal Inc., 1744 rue Williams, Montreal, Quebec, Canada or obtained from M. Thibonnier, Case Western Reserve University School of Medicine, Cleveland, Ohio.

Scheme VIII

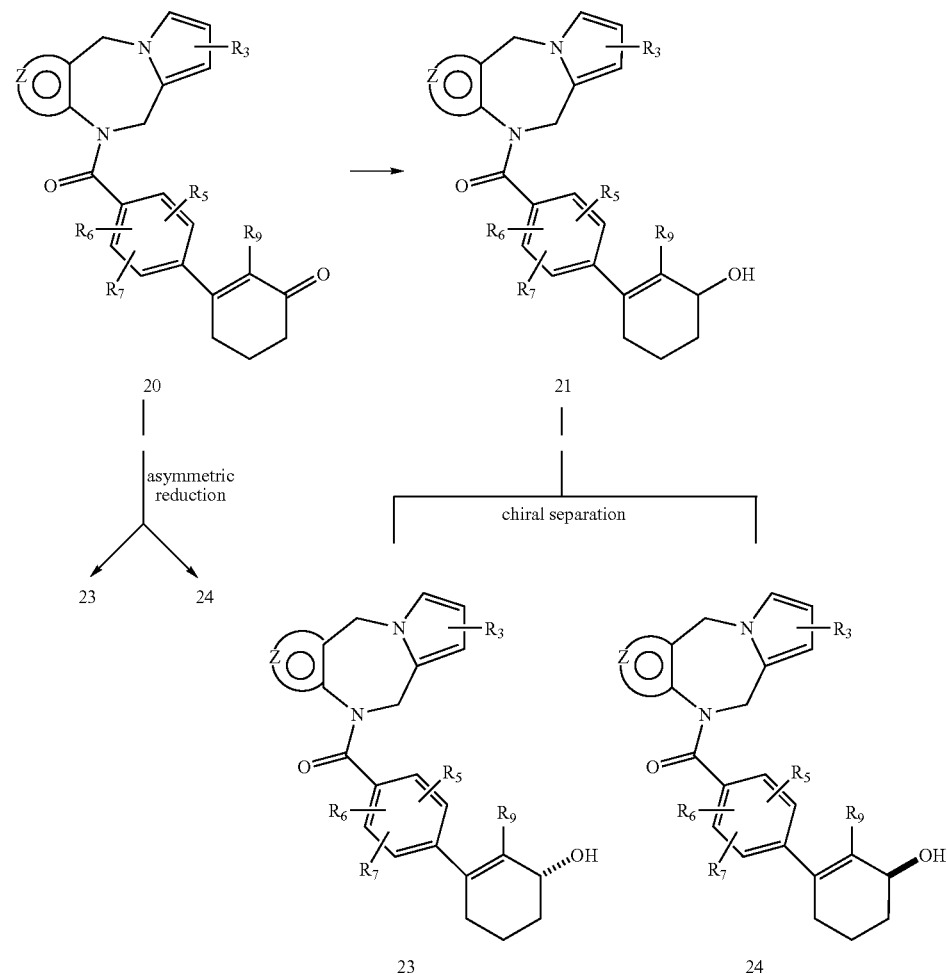

A. Passaging and Amplification of Cells:

CHO cells transfected with the human vasopressin $V_{1a}$ subtype receptors obtained from M. Thibonnier (pZeoSV vector) are allowed to grow to confluency (approx. >90%) in T-150 flasks under sterile conditions, in a cell culture medium of F-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 250 µg/mL Zeocin (add 1.25 mL of 100 mg/mL Invitrogen R-250-01 per 500 mL F-12) and 10% Fetal Bovine Serum (Qualified, heat inactivated, Gibco Cat. #16140-063). The medium is removed by aspiration and the cells are washed with 10 mL of Hank's Balanced Salt solution (Gibco Cat. #14175-095). The salt solution is removed by aspiration and the cells are trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (eg, 30 mL for 1:30 split) is immediately added and mixed well to inactivate trypsin. 1 mL of detached cells is added to new culture flasks containing fresh cell culture medium (eg, into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g.,. use 10 mL per T-150 flask). The excess is removed and the cells are bathed for 15–30 min. in an enzyme-free Cell Dissociation Buffer (e.g. use 8 mL Hank's Based, Gibco Cat. #13150-016 per T-150 flask) until the cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 µL (to make up a final volume of 200 µL) of assay buffer containing 50 mM of Tris-HCl (pH 7.4), BSA (heat inactivated, protease-free), 0.1% of 5 mM $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 µL of unlabeled Manning ligand (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. 20 µL of 50% DMSO is added for Manning and other peptide ligands and the assay buffer volume is adjusted accordingly. To each well is added 50 µL of frozen membrane suspension thawed immediately prior to use and diluted in the assay buffer to the required concentration (equivalent to 25 to 50 µg of protein/well as needed). 20 µL of 8 nM [$^3$H]Manning ligand in the assay buffer, prepared just before use, is added, and incubated at room temperature for 60 min. shaking the plate on a mechanical shaker for the first 15 min. The incubation is stopped by rapid filtration of the the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Vasopressin Binding in Chinese Hamster Ovary Cell Membranes Expressing Human Vasopressin $V_2$ Subtype Receptors Receptor Source:

Chinese Hamster Ovary (CHO) cells stably transfected with the human $V_2$ subtype receptors were obtained from M. Thibonnier, Case Western Reserve University School of Medicine, Cleveland, Ohio.

A. Passaging and Amplification of Cells:

CHO cells transfected with the human vasopressin $V_2$ subtype receptors obtained from M. Thibonnier (pZeoSV vector) are allowed to grow to confluency (approx. >90%) in T-150 flasks under sterile conditions, in a cell culture medium of F-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 250 µg/mL Zeocin (add 1.25 mL of 100 mg/mL Invitrogen R-250-01 per 500 mL F-12) and 10% Fetal Bovine Serum (Qualified, heat inactivated, Gibco Cat. #16140-063). The medium is removed by aspiration and the cells washed with 10 mL of Hank's Balanced Salt solution (Gibco Cat. #14175-095). The salt solution is removed by aspiration and the cells trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 day interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g. use 10 mL per T-150 flask). The excess solution is removed and the cells bathed for 15–30 min. in an enzyme-free Cell Dissociation Buffer (e.g. use 8 mL Hank's Based, Gibco Cat. # 13150-016 per T-150 flask) until cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogeneizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogeneizer and homogenized with 3 strokes. The homogenate is centrifuged at 1500×g for 60 min at 4° C. (3100 rpm using SORVAL, model RT6000D, using rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 µL (to make up a final volume of 200 µL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 µL of unlabeled arginine vasopressin (AVP) (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For vasopressin and other peptide ligands is added 20 µL of 50% DMSO and the assay buffer volume is adjusted accordingly.

To each well is added 50 µL of frozen membrane suspension thawed immediately prior to use and diluted in assay buffer to the required concentration (equivalent to 25 to 50 µg of protein/well as needed). 20 µL of 8 nM[$^3$H]arginine vasopressin (AVP) ligand in the assay buffer, prepared just before use is added and incubated at room temperature for 60 min. shaking the plate on a mechanical shaker for the first 15 min. The incubation is stopped by rapid filtration of the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Oxytocin Binding in Chinese Hamster Ovary Cell Membranes Expressing Human Oxytocin Receptors Receptor Source:

Chinese Hamster Ovary (CHO) cells stably transfected with the human oxytocin (cf. Tanizawa et al., U.S. Pat. No. 5,466,584 (1995) to Rohto Pharmaceutical Co. Ltd., Osaka, Japan) were obtained from M. Thibonnier, Case Western Reserve University School of Medicine, Cleveland, Ohio.

A. Passaging and Amplification of Cells:

CHO cells transfected with the human oxytocin receptors obtained from M. Thibonnier (pcDNA3.1 vector) are allowed to grow to confluency (approx. >90%) in T-150 flasks under sterile conditions, in a cell culture medium of F-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 400 µg/mL of Geneticin (add 4 mL of 50 mg/mL per 500 mL F-12) and 10% Fetal Bovine Serum (Qualified, heat inactivated, Gibco Cat. #16140-063). The medium is removed by aspiration and the cells are washed with 10 mL of Hank's Balanced Salt solution (Gibco Cat. #14175-095). The salt solution is removed by aspiration and the cells trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g., use 10 mL per T-150 flask). The excess is removed and the cells bathed for 15–30 min. in an enzyme-free Cell Dissociation Buffer (e.g., use 8 mL Hank's Based, Gibco Cat. #13150-016 per T-150 flask) until cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using rotor for 50 mL tubes). The pellet. is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microliter plate, is added 90, 110 or 130 µL (to make up a final volume of 200 µL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 µL of unlabeled oxytocin (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For oxytocin and other peptide ligands 20 µL of 50% DMSO is added and the assay buffer volume is adjusted accordingly.

To each well is added 50 µL of frozen membrane suspension thawed immediately prior to use and diluted in assay buffer to the required concentration (equivalent to 25 to 50 µg of protein/well as needed). 20 µL of 8 nM [$^3$H]oxytocin in the assay buffer, prepared just before use is added and incubated at room temperature for 60 min. shaking the plate on a mechanical shaker for the first 15 min. The incubation is stopped by rapid filtration of the the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Binding data is either reported as percent inhibition at a certain concentration or if an $IC_{50}$ was calculated, as a nanomolar concentration.

The results of these tests on representative compounds of this invention are shown in Table I.

TABLE 1

Binding to membranes of Chinese Hamster Ovary (CHO) cell line stably transfected with human vasopressin $V_{1a}$ receptor subtype, human vasopressin $V_2$ receptor subtype and human oxytocin receptor

| Example | OT % inhibition @ 100 nM ($IC_{50}$, nM)* | $V_{1a}$ % inhibition @ 100 nM ($IC_{50}$, nM)* | $V_2$ % inhibition @ 100 nM ($IC_{50}$, nM)* |
| --- | --- | --- | --- |
| 1 | (7.74) | (232) | (176) |
| 2 | 96 | 74 | 42 |
| 3 | (24) | (432) | (66) |
| 4 | 46 | 7 | 74 |
| 5 | 13 | 0 | 2 |
| 6 | 95 | 45 | 49 |
| 7 | (9.06) | (45.68) | (162.24) |
| 8 | 93 | −9 | 77 |
| 9 | 90 | 17 | 69 |
| 10 | 95 | 94 | 65 |
| 11 | 65 | 6 | 90 |
| 12 | 74 | 54 | 82 |
| 13 | 98 | 95 | 55 |
| 14 | 27 | 10 | 38 |
| 15 | (48.9) | (35.32) | (773.89) |
| 16 | (21.83) | (77.75) | (294.69) |
| 17 | 76 | 51 | 43 |
| 18 | 80 | 51 | 61 |
| 19 | 47 | 23 | 5 |
| 20 | 27 | 4 | 10 |
| 21 | 38 | 37 | 5 |
| 22 | 32 | 13 | 17 |
| 23 | 7 | −10 | 18 |
| 24 | 70 | 49 | 29 |
| 25 | 39 | 76 | 39 |
| 26 | 80 | 27 | 58 |
| 27 | 96 | 89 | 58 |

TABLE 1-continued

Binding to membranes of Chinese Hamster Ovary (CHO) cell line stably transfected with human vasopressin $V_{1a}$ receptor subtype, human vasopressin $V_2$ receptor subtype and human oxytocin receptor

| Example | OT % inhibition @ 100 nM ($IC_{50}$, nM)* | $V_{1a}$ % inhibition @ 100 nM ($IC_{50}$, nM)* | $V_2$ % inhibition @ 100 nM ($IC_{50}$, nM)* |
| --- | --- | --- | --- |
| 29 | 81 | 27 | 13 |
| 30 | 67 | 18 | 13 |
| 31 | (24) | (432) | (66) |
| 33 | 56 | 6 | 0 |
| 34 | 20 | −5 | 4 |
| 35 | 48 | 36 | 18 |
| 36 | 14 | 11 | 3 |
| 37 | 30 | 10 | 20 |
| 38 | 16 | 5 | −9 |
| 39 | 76 | 48 | 38 |
| 40 | 63 | 91 | 48 |
| 41 | 90 | 36 | 40 |
| 43 | 96 | 93 | 45 |
| 44 | 96 | 85 | 86 |
| 45 | 67 | 50 | 27 |

*Binding in Chinese Hamster Ovary cell membranes expressing human vasopressin $V_{1a}$ and $V_2$ subtype receptors, and human oxytocin receptors.

The following examples are presented to illustrate rather than limit the scope of this invention.

EXAMPLE 1

10-(5-Chloro-4-cyclohex-1-en-1-yl-2-methoxybenzoyl)-10,11-dihydro-5H-pyrrolo[2,1-c][1,4]benzodiazepine Step A. 4-Amino-5-chloro-2-methoxy-benzoic acid methyl ester 4-Amino-5-chloro-2-methoxy benzoic acid (50.0 g, 248 mmol) was suspended in methanol (500 mL) and the slurry cooled to 0° C. Thionyl chloride (54.3 mL, 744 mmol) was then added dropwise over the course of 20 minutes. Initially, a clear solution formed, which subsequently turned to a white suspension. The reaction was warmed to room temperature and stirred for 3 hours. The solvent was evaporated and the resulting slurry suspended in diethyl ether (1 L). The solid was filtered and rinsed thoroughly with diethyl ether to afford the title compound (50.9 g) as the hydrochloride salt. The salt was suspended in 1 N sodium hydroxide and stirred vigorously for 30 minutes. Filtration and thorough rinsing with water afforded the free base as a white solid, m.p. 136–137° C.

$^1$H NMR (DMSO-$d_6$, 400 MHz): δ 7.57 (s, 1H), 6.43 (s, 1H), 6.14 (s, 2H), 3.71 (s, 3H), 3.67 (s, 3H).

Anal. Calcd. for $C_9H_{10}ClNO_3$: C, 50.13; H, 4.67; N, 6.50. Found: C, 49.85; H, 4.46; N, 6.65.

MS [(+)-APCI, m/z]: 216 [M+H]$^+$. Calcd. for $C_9H_{11}ClNO_3$: 216.0428.

Step B. 5-Chloro-4-iodo-2-methoxy-benzoic acid methyl ester

4-Amino-5-chloro-2-methoxy benzoic acid methyl ester of Step A (5.00 g, 23.2 mmol) was suspended in water (52 mL) and concentrated sulfuric acid (13 mL) was added. The resulting suspension was cooled to −1° C. and a solution of sodium nitrite (1.76 g, 25.5 mmol) in water (10 mL) was added at a rate which maintained the temperature below 0° C., resulting in the formation of a clear yellow solution. A mixture of potassium iodide (4.23 g, 25.5 mmol) and iodine (3.24 g, 12.8 mmol) in water (50 mL) was then added dropwise and the reaction stirred at 0° C. for 1.5 hours. The reaction mixture was warmed to room temperature and extracted with ethyl acetate (200 mL). The organic extract was washed with 1 M sodium thiosulfate, 1 N sodium hydroxide and brine. The extract was dried over anhydrous magnesium sulfate, filtered and concentrated. Upon concentration, the product crystallized. The resulting orange crystals were suspended in petroleum ether, filtered and dried in vacuo to afford the title iodide (6.38 g), m.p. 72–73° C.

$^1$H NMR (DMSO-$d_6$, 400 MHz): δ 7.72 (s, 1H), 7.66 (s, 1H), 3.83 (s, 3H), 3.77 (s, 3H).

Anal. Calc. for $C_9H_8ClIO_3$: C, 33.11; H, 2.47. Found: C, 33.21; H, 2.23.

MS [(+)-APCI, m/z]: 327 [M+H]$^+$. Calcd. for $C_9H_9ClIO_3$: 326.9285.

Step C. 5-Chloro-4-iodo-2-methoxy-benzoic acid

5-Chloro-4-iodo-2-methoxy benzoic acid methyl ester of Step B (3.00 g, 9.19 mmol) and sodium hydroxide (1.10 g, 27.6 mmol) were combined in methanol (92 mL) and the mixture refluxed for 12 hours. The reaction was cooled to room temperature and solvent evaporated. The residue was dissolved in 1 N sodium hydroxide (75 mL), washed with diethyl ether and the organic washings discarded. The aqueous phase was acidified with 2 N hydrochloric acid and extracted with diethyl ether. The combined extracts were dried over anhydrous sodium sulfate, filtered and concentrated to afford the title carboxylic acid (2.64 g) as orange crystals, m.p. 150–151° C.

$^1$H NMR (DMSO-$d_6$, 400 MHz): δ 13.03 (bs, 1H), 7.70 (s, 1H), 7.63 (s, 1H), 3.82 (s, 3H).

Anal. Calcd. for $C_8H_6ClIO_3$: C, 30.75; H, 1.94. Found: C, 31.28; H, 1.78.

MS [(−)-APCI, m/z]: 311 [M−H]$^-$. Calcd. for $C_8H_5ClIO_3$ 310.8972.

Step D. (5H,11H-Benzo[e]pyrrolo[1,2-a][1,4]diazepin-10-yl)-(5-chloro-4-iodo-2-methoxy-phenyl)-methanone 5-Chloro-4-iodo-2-methoxy benzoic acid of Step C (0.900 g, 2.88 mmol) and N,N-dimethylformamide (0.0067 mL, 0.0864 mmol) were combined in anhydrous dichloromethane (14.4 mL) followed by dropwise addition of oxalyl chloride (0.263 mL, 3.02 mmol). The mixture was heated to reflux for 1 hour, then cooled to room temperature and evaporated. Fresh anhydrous dichloromethane (25 mL) was added, the resulting solution concentrated and the residue dried in vacuo.

The above crude acid chloride and 10,11-dihydro-5H-pyrrolo[2,1-c][1,4]benzodiazepine (0.584 g, 3.17 mmol) were combined in anhydrous dichloromethane (14.4 mL), followed by addition of N,N-diisopropylethyl amine (0.447 mL, 3.46 mmol). After stirring at room temperature for 18 hours, the reaction mixture was diluted with dichloromethane (15 mL) and washed with 1 N hydrochloric acid, 1 N sodium hydroxide and brine. The organic phase was dried over anhydrous magnesium sulfate, filtered and concentrated to afford the crude amide which was recrystallized from diethyl ether to provide slightly orange crystals (1.23 g), m.p. 191–192° C.

$^1$H NMR (DMSO-$d_6$, 400 MHz): δ 7.60–7.28 (m, 3H), 7.14–7.01 (m, 3H), 6.79 (s, 1H), 5.95 (s, 1H), 5.89 (t, J=3.1, 1H), 5.15 (bs, 4H), 3.56 (s, 3H).

Anal. Calcd. for $C_{20}H_{16}ClIN_2O_2$: C, 50.18; H, 3.37; N, 5.85. Found: C, 50.47; H, 3.28; N, 5.74.

MS [EI, m/z]: 478 [M]$^+$. Calcd. for $C_{20}H_{16}ClIN_2O_2$: 477.9946.

Step E. (10,11-Dihydro-5H-pyrrolo[2,1-c][1,4]benzodiazepin-10-yl)-[5-chloro-2-methoxy-4-(4,4,5,5-tetramethyl-[1,3,2]dioxaborolan-2-yl)-phenyl]-methanone (5H,11H-Benzo[e]pyrrolo[1,2-a][1,4]diazepin-10-yl)-(5-chloro-4-iodo-2-methoxy-phenyl)-methanone of Step D (0.500 g, 1.04 mmol), bis(pinacolato)diboron (0.289 g, 1.14 mmol), potassium acetate (0.306 g, 3.12 mmol) and dichloro[1,1'-bis(diphenylphosphino)ferrocene]palladium(II) dichloromethane adduct (0.025 g, 0.031 mmol) were combined in anhydrous dimethyl sulfoxide (5.2 mL) and heated to 80° C. overnight. The reaction mixture was cooled to room temperature, diluted with ethyl acetate (60 mL) and washed with water and brine. The organic phase was dried over anhydrous sodium sulfate, diluted with hexane and filtered through a plug of silica gel. The filtrate was concentrated to an oil and the product recrystallized from diethyl ether/petroleum ether (−20° C.) to provide the title compound (0.430 g) as a white, crystalline solid, m.p. 92–98° C.

$^1$H NMR (DMSO-$d_6$, 400 MHz): δ 7.48–7.36 (m, 2H), 7.12–7.03 (m, 4H), 6.79 (s, 1H), 5.95 (m, 1H), 5.89 (t, J=3.1, 1H), 5.20 (bs, 4H), 3.48 (bs, 3H), 1.26 (s, 12H).

Anal. Calcd. for $C_{26}H_{28}BClN_2O_4$: C, 56.22; H, 5.89; N, 5.85. Found: C, 56.23; H, 5.63; N, 6.24.

MS [(+)-ESI, m/z]: 479 [M+H]$^+$. Calcd. for $C_{26}H_{29}BClN_2O_4$: 479.1910.

Step F. 10-(5-Chloro-4-cyclohex-1-en-1-yl-2-methoxybenzoyl)-10,11-dihydro-5H-pyrrolo[2,1-c][1,4]benzodiazepine (10,11-Dihydro-5H-pyrrolo[2,1-c][1,4]benzodiazepin-10-yl)-[5-chloro-2-methoxy-4-(4,4,5,5-tetramethyl-[1,3,2]dioxaborolan-2-yl)-phenyl]-methanone of Step E (0.220 g, 0.459 mmol), cyclohex-1-en-1-yl trifluoromethanesulfonate (0.116 g, 0.505 mmol) and dichloro[1,1'-bis(diphenylphosphino)ferrocene]palladium(II) dichloromethane adduct (0.011 g, 0.014 mmol) were combined in N,N-dimethylformamide (2.3 mL). 2 M aqueous sodium carbonate (1.15 mL, 2.30 mmol) was added and the reaction heated to 60° C. for 2 hours. After cooling to room temperature, the reaction mixture was diluted ethyl acetate and washed with water and brine. The organic phase was dried over anhydrous magnesium sulfate, filtered and concentrated. Flash column chromatography on silica gel eluting with a solvent gradient from 30 to 40% ethyl acetate in hexane afforded the title compound (0.140 g) as an oil. The oil was dissolved in diethyl ether/petroleum ether and concentrated to afford an amorphous white solid.

$^1$H NMR (DMSO-$d_6$, 400 MHz): δ 7.38 (d, J=7.0, 2H), 7.11 (t, J=7.0, 1H), 7.06–7.00 (m, 2H), 6.79 (s, 1H), 6.57 (s, 1H), 5.95 (s, 1H), 5.89 (t, J=3.0, 1H), 5.55 (s, 1H), 5.24–4.60 (m, 4H), 3.52 (s, 3H), 2.13–2.09 (m, 4H), 1.68–1.57 (m, 4H).

Anal. Calcd. for $C_{26}H_{25}ClN_2O_2+0.03C_4H_{10}O$: C, 71.76; H, 5.79; N, 6.44. Found: C, 71.66; H, 5.59; N, 6.10.

MS [(+)-APCI, m/z]: 433 [M+H]$^+$. Calcd. for $C_{26}H_{26}ClN_2O_2$: 433.1684.

EXAMPLE 2

(10,11-Dihydro-5H-pyrrolo[2,1-c][1,4]benzodiazepin-10-yl)-(4-cyclohex-1-en-1-yl-3-methyl-phenyl)-methanone Step A. (10,11-Dihydro-5H-pyrrolo[2,1-c][1,4]benzodiazepin-10-yl)-(4-bromo-3-methyl-phenyl)-methanone To a stirred mixture of 4-bromo-3-methyl benzoic acid (21.5 g, 100 mmol) and N,N-dimethylformamide (0.251 mL, 3.00 mmol) in anhydrous dichloromethane (200 mL) was added dropwise oxalyl chloride (9.16 mL, 105 mmol). The mixture was heated to reflux for 1.5 hours, then cooled to room temperature and the solvent evaporated. Fresh anhydrous dichloromethane (200 mL) was added and the resulting solution concentrated and the residue was dried in vacuo. The crude acid chloride thus obtained and 10,11-dihydro-5H-pyrrolo[2,1-c][1,4]benzodiazepine (17.5 g, 95.0 mmol) were combined in anhydrous dichloromethane (200 mL), followed by addition of N,N-diisopropylethyl amine (19.2 mL, 110 mmol). After stirring at room temperature for 18 hours, the reaction mixture was washed with 1 N hydrochloric acid, 1 N sodium hydroxide and brine. The organic phase was dried over anhydrous magnesium sulfate, filtered and concentrated to afford the crude amide which was recrystallized from ethyl acetate to provide slightly orange crystals (34.8 g) of the title compound, m.p. 175–176° C.

$^1$H NMR (DMSO-$d_6$, 400 MHz): δ 7.45 (dd, 1H), 7.38 (d, 1H), 7.33 (d, 1H), 7.18 (dt, 1H), 7.10 (t, 1H), 6.92 (s, 1H), 6.90 (s, 1H), 6.82 (t, 1H), 5.94 (s, 1H), 5.91 (t, 1H), 5.27–4.80 (br, 4H), 2.22 (s, 3H).

Anal. Calcd. for $C_{20}H_{17}BrN_2O+0.20H_2O$: C, 62.42; H, 4.56; N, 7.28. Found: C, 62.43; H, 4.60; N, 7.24.

MS [(+)-ESI, m/z]: 381 [M+H]$^+$. Calcd. for $C_{20}H_{18}BrN_2O$: 381.0598.

Step B. (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone (10,11-Dihydro-5H-pyrrolo[2,1-c][1,4]benzodiazepin-10-yl)-(4-bromo-3-methyl-phenyl)-methanone of Step A (20.0 g, 52.5 mmol), bis(pinacolato)diboron (14.7 g, 57.8 mmol), potassium acetate (15.5 g, 158 mmol) and dichloro[1,1'-bis(diphenylphosphino) ferrocene]palladium (II) dichloromethane adduct (1.29 g, 1.58 mmol) were combined in anhydrous dimethyl sulfoxide (263 mL) and heated to 80° C. for 18 hours. The reaction was cooled to room temperature and additional catalyst (1.29 g, 1.58 mmol) and bis(pinacolato)diboron (3.33 g, 13.1 mmol) were added. Heating was resumed at 80° C. for an additional 18 hours. The reaction mixture was cooled to room temperature, diluted with ethyl acetate (500 mL) and filtered through silica gel. The filtrate was washed with water and brine. The organic phase was dried over anhydrous sodium sulfate, diluted with hexane and filtered through a plug of silica gel. The filtrate was concentrated to an oil and pentane added, causing the product to crystallize. The off-white crystals were filtered and dried in vacuo to provide 18.4 g of the title compound, m.p. 190–193° C.

$^1$H NMR (DMSO-$d_6$, 400 MHz): δ 7.45 (dd, 1H), 7.39 (d, 1H), 7.18–7.06 (m, 3H), 6.98 (d, 1H), 6.91 (br, 1H), 6.81 (t, 1H), 5.94 (br, 1H), 5.91 (t, 1H), 5.33–4.60 (br, 4H), 2.32 (s, 3H), 1.25 (s, 12H).

Anal. Calcd for $C_{26}H_{29}BN_2O_3+0.12C_4H_8O_2$: C, 72.46; H, 6.88; N, 6.38. Found: C, 70.80; H, 6.83; N, 6.06.

MS [(+)-ESI, m/z]: 429 [M+H]$^+$. Calcd. for $C_{26}H_{30}BN_2O_3$: 429.2348.

Step C. (10,11-Dihydro-5H-pyrrolo[2,1-c][1,4]benzodiazepin-10-yl-(4-cyclohex-1-enyl-3-methyl-phenyl)-methanone (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Step B (3.50 g, 8.17 mmol), cyclohex-1-en-1-yl trifluoromethanesulfonate (2.26 g, 9.80 mmol) and dichloro[1,1'-bis(diphenylphosphino)ferrocene] palladium (II) dichloromethane adduct (0.200 g, 0.245 mmol) were combined in N,N-dimethylformamide (40.9 mL). Aqueous sodium carbonate (2M, 20.5 mL, 40.9 mmol) was added and the reaction heated to 60° C. overnight. After cooling to room temperature, the reaction mixture was diluted with ethyl acetate and washed with water and brine. The organic phase was dried over anhydrous magnesium sulfate, filtered and concentrated. The residue was dissolved in hot ethyl acetate/petroleum ether (1:1) and filtered. The filtrate was concentrated and the residue recrystallized from petroleum ether to afford 2.52 g of the title compound as pale brown crystals, m.p. 182–183° C.

$^1$H NMR (DMSO-$d_6$, 400 MHz): δ 7.47 (dd, 1H), 7.21–7.10 (m, 3H), 6.93 (d, 2H), 6.83 (d, 1H), 6.81 (t, 1H), 5.93–5.91 (m, 2H), 5.43 (m, 1H), 5.26 (br, 2H), 5.20–4.80 (br, 2H), 2.11 (s, 3H), 2.09–2.05 (m, 4H), 1.67–1.56 (m, 4H).

Anal. Calcd. for $C_{26}H_{26}N_2O+0.15H_2O$: C, 81.07; H, 6.88; N, 7.27. Found: C, 81.03, H, 6.86; N, 7.24.

MS [(+)-ESI, m/z]: 383 [M+H]$^+$. Calcd. for $C_{26}H_{27}N_2O$: 383.2128.

EXAMPLE 3

(10,11-Dihydro-5H-pyrrolo[2,1-c][1,4]benzodiazepin-10-yl)-[4-(3,4-dihydro-naphthalen-1-yl)-3-methyl-phenyl]-methanone (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2, Step B (0.760 g, 1.89 mmol), 3,4-dihydro-naphthalen-1-yl trifluoromethanesulfonate (0.579 g, 2.08 mmol) and dichloro[1,1'-bis(diphenylphosphino)ferrocene]palladium (II) dichloromethane adduct (0.046 g, 0.057 mmol) were combined in N,N-dimethylformamide (9.5 mL). Aqueous sodium carbonate (2M, 4.73 mL, 9.45 mmol) was added and the was heated to 60° C. for 3 hours. After cooling to room temperature, the mixture was diluted with ethyl acetate and washed with water and brine. The organic phase was dried over anhydrous magnesium sulfate, filtered and concentrated and the residue purified by flash column chromatography on silica gel eluting with 30% ethyl acetate in hexane. Recrystallization from hexane afforded 0.740 g of the title compound as white crystals, m.p. 108° C.

$^1$H NMR (DMSO-$d_6$, 400 MHz): δ 7.46 (d, 1H), 7.22–6.91 (m, 9H), 6.93 (s, 1H), 6.22 (d, H), 5.95 (s, 1H), 5.92 (t, 1H), 5.84 (t, 1H), 5.30 (br, 4H), 2.77 (t, 2H), 2.35–2.32 (m, 2H), 1.88 (s, 3H).

Anal. Calcd. for $C_{30}H_{26}N_2O+0.16C_6H_{14}+0.30H_2O$: C, 82.68; H, 6.46; N, 6.23. Found: C, 82.47; H, 6.63; N, 6.05.

MS [(+)-APCI, m/z]: 431 [M+H]$^+$. Calcd. for $C_{30}H_{27}N_2O$ 431.2128.

EXAMPLE 4

3-[2-Methyl-4-(5H-pyrrolo[2,1-c][1,4]benzodiazepin-10(11H)-yl-carbonyl)phenyl]-2-methyl-cyclohex-2-en-1-one (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2 Step B (6.75 g, 15.8 mmol), 3-oxo-2-methylcyclohexen-1-yl trifluoromethanesulfonate (4.49 g, 17.4 mmol) and dichloro[1,1'-bis(diphenylphosphino)ferrocene]palladium (II) dichloromethane adduct (0.387 g, 0.474 mmol) were combined in dimethylsulfoxide (79 mL). Aqueous sodium carbonate (2M, 39.5 mL, 79.0 mmol) was added and the reaction heated to 60° C. for 3 hours. After cooling to room temperature, the reaction mixture was diluted with water and washed with ethyl acetate. The combined extracts were washed with water and brine. The organic phase was dried over anhydrous sodium sulfate, filtered through silica gel and concentrated. The residue was purified by flash column chromatography on silica gel eluting with 50% ethyl acetate in hexane to provide 3.55 g of the title compound as a pale orange foam.

$^1$H NMR (DMSO-d$_6$, 400 MHz): δ 7.45 (dd, 1H), 7.24 (s, 1H), 7.17 (t, 1H), 7.07 (t, 1H), 7.05 (d, 1H), 6.91 (d, 1H), 6.85 (d, 1H), 6.82 (t, 1H), 5.94 (s, 1H), 5.91 (t, 1H), 5.34–4.65 (br, 4H), 2.42–2.32 (m, 4H), 2.02 (s, 3H), 2.00–1.93 (m, 2H), 1.25 (s, 3H).

Anal. Calcd. for $C_{27}H_{26}N_2O_2+0.50H_2O+0.05C_6H_{14}$: C, 77.37; H, 6.59; N, 6.60. Found: C, 77.40; H, 6.76; N, 6.51.

MS [(+)-APCI, m/z]: 411.1 [M+H]$^+$. Calcd. for $C_{27}H_{27}N_2O_2$: 411.2078.

EXAMPLE 5

(10,11-Dihydro-5H-pyrrolo[2,1-c][1,4]benzodiazepin-10-yl)-[4-(3-hydroxy-2-methyl-cyclohex-1-en-1-yl)-3-methyl-phenyl]-methanone 3-[2-Methyl-4-(5H-pyrrolo[2,1-c][1,4]benzodiazepin-10(11H)-yl-carbonyl)phenyl]-2-methyl-cyclohex-2-en-1-one of Example 4 (0.350 g, 0.853 mmol), and cerium (III) chloride (0.210 g, 0.853 mmol) were combined in methanol (4.3 mL) followed by addition of sodium borohydride (0.032 g, 0.853 mmol). The reaction was stirred at room temperature until gas evolution ceased (approximately 2 minutes), then quenched with 0.1 N hydrochloric acid (100 mL), causing a white precipitate to form. The precipitate was filtered and purified by flash column chromatography on silica gel eluting with 50% ethyl acetate in hexane to afford 0.310 g of the title alcohol as a white solid.

$^1$H NMR (DMSO-d$_6$, 400 MHz): δ 7.45 (dd, 1H), 7.19–7.15 (m, 2H), 7.07 (t, 1H), 6.95 (t, 1H), 6.89 (d, 1H), 6.81 (t, 1H), 6.73 (t, 1H), 5.94–5.90 (m, 2H), 5.27–4.65 (br, 4H), 4.62 (dd, 1H), 3.91–3.83 (m, 1H), 1.98 (d, 3H), 1.90 (br, 2H), 1.76–1.59 (m, 3H), 1.54–1.49 (m, 1H), 1.24 (s, 3H).

Anal. Calcd. for $C_{27}H_{28}N_2O_2+0.04C_4H_{10}O$: C, 78.05; H, 6.79; N, 6.74. Found: C, 78.00; H, 7.07; N, 6.49.

MS [(+)-APCI, m/z]: 413.1 [M+H]$^+$. Calcd. for $C_{27}H_{29}N_2O_2$: 413.2228.

EXAMPLE 6

(10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone (S)-(–)-tetrahydro-1-methyl-3,3-diphenyl-1H,3H-pyrrolo[1,2-c][1,3,2]oxazaboro-borane [(S)-2-methyl-CBS-oxazaborolidine] (1.0 M in tetrahydrofuran, 1.06 mL, 1.06 mmol) was dissolved in anhydrous tetrahydrofuran (53.1 mL, distilled from sodium/benzophenone ketyl). To this solution was simultaneously added a solution of 3-[4-(5H,1H-benzo[e]pyrrolo[1,2-a][1,4]diazepine-10-carbonyl)-2-methyl-phenyl]-2-methyl-cyclohex-2-enone of Example 4 (2.18 g, 5.31 mmol) in anhydrous tetrahydrofuran (20 mL) via syringe pump (1.6 mL/min) and borane-tetrahydrofuran complex (1.0 M in tetrahydrofuran, 3.19 mL, 3.19 mmol) at a rate such that enone addition was complete upon addition of approximately ⅔ of the borane-tetrahydrofuran complex. Upon completion of the borane-tetrahydrofuran complex addition, the reaction mixture was diluted with water and extracted with ethyl acetate. The combined extracts were washed with 1 N sodium hydroxide, 1 N hydrochloric acid and brine and dried over anhydrous magnesium sulfate, filtered and concentrated. The residue was purified by flash column chromatography on silica gel eluting with 50% ethyl acetate in hexane followed by reprecipitation from diethyl ether upon addition of petroleum ether, to afford 2.02 g of the title compound as a white solid, $[\alpha]_{589}$=+34.30 (c=1, chloroform). Analytical HPLC (Chiralpak AD, 4.6×250 mm, 50% ethanol/hexane, 0.5 mL/min.) indicated an enantiomeric excess of 96.4%.

$^1$H NMR (DMSO-d$_6$, 400 MHz): δ 7.45 (dd, 1H), 7.18–7.14 (m, 2H), 7.07 (t, 1H), 6.95 (t, 1H), 6.88 (d, 1H), 6.81 (t, 1H), 6.73 (t, 1H), 5.93 (s, 1H), 5.91 (t, 1H), 5.27 (br, 2H), 5.25–4.80 (br, 2H), 3.90–3.84 (m, 1H), 1.99 (d, 3H), 1.90 (br, 2H), 1.75–1.59 (m, 3H), 1.54–1.49 (m, 1H), 1.24 (s, 3H).

Anal. Calcd. for $C_{27}H_{28}N_2O_2+0.50H_2O+0.10C_4H_{10}O$: C, 75.60; H, 6.81; N, 6.53. Found: C, 75.52; H, 6.92; N, 6.54.

MS [(+)-APCI, m/z]: 413.2 [M+H]$^+$. Calcd. for $C_{27}H_{29}N_2O_2$: 413.2230.

EXAMPLE 7

(10,11-Dihydro-5H-pyrrolo[2,1-c][1,4]benzodiazepin-10-yl)-[4-(2-methyl-cyclohex-1-en-1-yl)-phenyl]-methanone Step A. 4-(4,4,5,5-Tetramethyl-[1,3,2]dioxaborolan-2-yl)-benzoic acid methyl ester 4-Bromo benzoic acid methyl ester (20.0 g, 93.0 mmol), bis(pinacolato)diboron (26.0 g, 102 mmol), potassium acetate (27.4 g, 279 mmol) and dichloro[1,1'-bis(diphenylphosphino) ferrocene]palladium (II) dichloromethane adduct (2.28 g, 2.79 mmol) were combined in anhydrous dimethyl sulfoxide (465 mL) and heated to 80° C. for 18 hours. The reaction mixture was cooled to room temperature, diluted with diethyl ether and filtered through silica gel. The filtrate was washed with water and brine, dried over anhydrous sodium sulfate, filtered and concentrated to afford the title compound (22 g) as an oil, which was recrystallized from pentane (–20° C.), m.p. 79° C.

$^1$H NMR (CDCl$_3$, 400 MHz): δ 8.03–8.01 (m, 2H), 7.88–7.86 (m, 2H), 3.92 (s, 3H), 1.36 (s, 12H).

Anal. Calcd for $C_{14}H_{19}BO_4$: C, 64.15; H, 7.31. Found: C, 64.30; H, 7.20.

MS [EI, m/z]: 262 [M]$^+$. Calcd. for $C_{14}H_{19}BO_4$: 262.138.

Step B. 4-(2-Methyl-cyclohex-1-en-1-yl)-benzoic acid methyl ester 4-(4,4,5,5-Tetramethyl-[1,3,2]dioxaborolan-2-yl)-benzoic acid methyl ester of Step A (2.0 g, 7.63 mmol) and a mixture of 2-methyl-cyclohex-1-en-1-yl trifluoromethanesulfonate and 6-methyl cyclohex-1-en-1-yl trifluoromethanesulfonate (2.24 g, 9.16 mmol, approximately 5:1 ratio) were reacted in the manner of Example 1, Step F. Purification by preparative HPLC (Primesphere 5 silica, 5% methyl tert-butyl ether in hexane) afforded the title compound as an amorphous white solid.

$^1$H NMR (DMSO-d$_6$, 400 MHz): δ 7.91–7.87 (m, 2H), 7.29–7.26 (m, 2H), 3.83 (s, 3H), 2.21–2.18 (m, 2H), 2.06–2.04 (m, 2H), 1.69–1.60 (m, 4H), 1.52 (s, 3H).

Anal. Calcd. for $C_{15}H_{18}O_2$: C, 78.23; H, 7.88. Found: C, 77.79; H, 7.74.

MS [(+)-APCI, m/z]: 231.0 [M+H]$^+$. Calcd. for $C_{15}H_{19}O_2$: 231.1386.

Step C. 4-(2-Methyl-cyclohex-1-en-1-yl)-benzoic acid 4-(2-Methyl-cyclohex-1-en-1-yl)-benzoic acid methyl ester of Step B (0.827 g, 3.59 mmol) was saponified in the manner of Example 1, Step C to provide the title compound (0.760 g) as a white crystalline solid, m.p. 176–178° C.

$^1$H NMR (DMSO-d$_6$, 400 MHz): δ 12.79 (b, 1H), 7.89–7.86 (m, 2H), 7.26–7.23 (m, 2H), 2.20 (br, 2H), 2.06 (br, 2H), 1.69–1.61 (m, 4H), 1.52 (s, 3H).

Anal. Calcd. for $C_{14}H_{16}O_2$: C, 77.75; H, 7.46. Found: C, 77.56; H, 7.55.

MS [EI, m/z]: 216 [M]$^+$. Calcd. for $C_{14}H_{16}O_2$: 216.115.

Step D. (10,11-Dihydro-5H-pyrrolo[2,1-c][1,4]benzodiazepin-10-yl)-[4-(2-methyl-cyclohex-1-en-1-yl)-phenyl]-methanone 4-(2-Methyl-cyclohex-1-en-1-yl)-benzoic acid of Step C (0.720 g, 3.33 mmol) and 10,11-dihydro-5H-pyrrolo[2,1-c][1,4]benzodiazepine (0.674 g, 3.66 mmol) were reacted in the manner of Example 1, Step D. The title compound was purified by recrystallization from petroleum ether to afford white crystals (1.17 g), m.p. 119–120° C.

$^1$H NMR (DMSO-d$_6$, 400 MHz): δ 7.45 (dd, 1H), 7.21–7.14 (m, 3H), 7.07 (t, 1H), 6.97 (d, 2H), 6.89 (d, 1H), 6.81 (t, 1H), 5.94 (s, 1H), 5.91 (t, J 1H), 5.35–4.60 (br, 4H), 2.10 (br, 2H), 1.99 (br, 2H), 1.63–1.56 (m, 4H), 1.40 (s, 3H).

Anal. Calc'd for $C_{26}H_{26}N_2O$: C, 81.64; H, 6.85; N, 7.32. Found: C, 81.34; H, 7.31; N, 7.32.

MS [(+)-APCI, m/z]: 383.2 [M+H]$^+$. Calcd. for $C_{26}H_{27}N_2O$: 383.2125.

EXAMPLE 8

10-[5-Chloro-4-(3,4-dihydro-naphthalen-1-yl)-2-methoxybenzoyl]-10,11-dihydro-5H-pyrrolo[2,1-c][1,4]benzodiazepine (10,11-Dihydro-5H-pyrrolo[2,1-c][1,4]benzodiazepin-10-yl)-[5-chloro-2-methoxy-4-(4,4,5,5-tetramethyl-[1,3,2]dioxaborolan-2-yl)-phenyl]-methanone of Example 1 Step E (0.170 g, 0.355 mmol) and naphthalen-1-yl trifluoromethanesulfonate (0.109 g, 0.391 mmol) were reacted in the manner of Example 1, Step F. Purification by flash column chromatography on silica gel, eluting with 40% ethyl acetate in hexane followed by recrystallization from diethyl ether/pentane afforded the title compound (0.150 g) as white crystals, m.p.: 209–210° C.

$^1$H NMR (DMSO-d$_6$, 400 MHz): δ 7.50 (br, 1H), 7.39 (d, J=6.6, 1H), 7.18–7.02 (m, 5H), 6.81 (m, 1H), 6.66 (b, 1H), 6.20 (br, 1H), 5.98 (s, 1H), 5.93–5.88 (m, 2H), 5.35–4.60 (br, 5H), 3.51 (br, 3H), 2.78 (t, J=7.9, 2H), 2.40–2.24 (m, 2H).

Anal. Calcd. for $C_{30}H_{25}ClN_2O_2+0.10C_4H_8O_2$: C, 74.55; H, 5.31; N, 5.72. Found: C, 74.37; H, 5.14; N, 5.53.

MS [(+)-APCI, m/z]: 481.2 [M+H]$^+$. Calcd. for $C_{30}H_{26}ClN_2O_2$: 481.1684.

EXAMPLE 9

3-[2-Chloro-5-methoxy-4-(5H-pyrrolo[2,1-c][1,4]benzodiazepin-10(11H)-yl-carbonyl)phenyl]-2-methyl-cyclohex-2-en-1-one (10,11-Dihydro-5H-pyrrolo[2,1-c][1,4]benzodiazepin-10-yl)-[5-chloro-2-methoxy-4-(4,4,5,5-tetramethyl-[1,3,2]dioxaborolan-2-yl)-phenyl]-methanone of Example 1, Step E (0.700 g, 1.46 mmol) and 2-methyl-3-oxo-cyclohex-1-en-1-yl trifluoromethanesulfonate (0.416 g, 1.61 mmol) were reacted by the procedure described in Example 1, Step F. Purification by flash column chromatography on silica gel, eluting with 50% ethyl acetate in hexane followed by precipitation from diethyl ether with pentane afforded the title compound (0.270 g) as an amorphous yellow solid.

$^1$H NMR (DMSO-d$_6$, 400 MHz): δ 7.58–7.47 (m, 1H), 7.37 (d, J=7.5, 1H), 7.15–7.08 (m, 1H), 6.98 (d, J=3.7, 2H), 6.80 (s, 1H), 6.67 (s, 1H), 5.96 (s, 1H), 5.89 (t, J=3.1, 1H), 5.35–4.60 (br, 4H), 3.52 (br, 3H), 2.40 (t, J=6.5, 4H), 2.06–1.92 (m, 2H), 1.28 (s, 3H).

Anal. Calcd. for $C_{27}H_{25}ClN_2O_3+0.15C_4H_{10}O$: C, 68.70; H, 5.34; N, 5.93. Found: C, 68.63; H, 5.43; N, 5.73.

MS [(+)-ESI, m/z]: 461.2 [M+H]$^+$. Calcd. for $C_{27}H_{26}ClN_2O_3$: 461.1633.

EXAMPLE 10

(10,11-dihydro-5H-pyrrolo[2,1-c][1,4]benzodiazepin-10-yl)-[2-chloro-4-(cyclohex-1-en1-yl)-phenyl]-methanone Step A. 10-(4-Bromo-2-chloro)-10,11-dihydro-5H-pyrrolo[2,1-c][1,4]benzodiazepine 4-Bromo-2-chloro-benzoic acid (6.05 g, 25.7 mmol) and N,N-dimethylformamide (0.060 mL, 0.056 mmol) were combined in anhydrous dichloromethane (257 mL) followed by dropwise addition of oxalyl chloride (2.04 mL, 27.0 mmol). The mixture was heated to reflux for 1.5 hours, then cooled to room temperature and the solvent evaporated. Fresh anhydrous dichloromethane (150 mL) was added and the resulting solution concentrated and the residue dried in vacuo.

The above crude acid chloride and 10,11-dihydro-5H-pyrrolo[2,1-c][1,4]benzodiazepine (5.21 g, 28.3 mmol) were combined in anhydrous dichloromethane (257 mL), followed by addition of N,N-diisopropylethyl amine (5.37 mL, 30.8 mmol). After stirring at room temperature for 18 hours, the reaction mixture was concentrated and the residue diluted with ethyl acetate and washed with 1 N hydrochloric acid, 1 N sodium hydroxide and brine. The organic phase was dried over anhydrous magnesium sulfate, filtered and concentrated to afford the crude amide which was precipitated from diethyl ether with pentane to yield a slightly yellow, amorphous solid (9.82 g).

$^1$H NMR (DMSO-d$_6$, 400 MHz): δ 7.74 (m, 1H), 7.39–7.28 (m, 3H), 7.13 (dt, J=1.3, 7.5, 1H), 7.07 (dt, J=1.5, 7.5, 1H), 7.01 (dd, J=1.3, 7.7, 1H), 6.81 (t, J=2.1, 1H), 5.99 (m, 1H), 5.89 (t, J=3.1, 1H), 5.40–4.90 (br, 4H).

Anal. Calcd. for $C_{19}H_{14}BrClN_2O$: C, 56.81; H, 3.51; N, 6.97. Found: C, 55.92; H, 3.66; N, 6.17.

MS [(+)-APCI, m/z]: 401.1 [M+H]$^+$. Calcd. for $C_{19}H_{15}BrClN_2O$: 401.0058.

Step B. (10,11-Dihydro-5H-pyrrolo[2,1-c][1,4]benzodiazepin-10-yl)-[2-chloro-4-(4,4,5,5-tetramethyl-[1,3,2]dioxaborolan-2-yl)-phenyl]-methanone 10-(4-Bromo-2-chloro)-10,11-dihydro-5H-pyrrolo[2,1-c][1,4]benzodiazepine of Step A (2.00 g, 4.98 mmol) and bis(pinacolato)diboron (1.39 g, 5.48 mmol) were reacted by the procedure described in Example 1, Step E. The crude boronate was isolated and carried on without purification.

Step C. (10,11-Dihydro-5H-pyrrolo[2,1-c][1,4]benzodiazepin-10-yl)-[2-chloro-4-(cyclohex-1-en-1-yl)-phenyl]-methanone (10,11-Dihydro-5H-pyrrolo[2,1-c][1,4]benzodiazepin-10-yl)-[2-chloro-4-(4,4,5,5-tetramethyl-[1,3,2]dioxaborolan-2-yl)-phenyl]-methanone of Step B (0.300 g, 0.668 mmol) and cyclohexen-1-yl trifluoromethanesulfonate (0.169 g, 0.735 mmol) were reacted by the procedure described in Example 1, Step F. The crude product was purified by flash column chromatography on silica gel, eluting with 30% ethyl acetate/hexane to afford a clear oil. The oil was dissolved in diethyl ether and precipitated with petroleum ether to afford 0.250 g of a white solid.

$^1$H NMR (DMSO-$d_6$, 400 MHz): δ 7.57–7.45 (m, 1H), 7.37 (d, J=6.8, 1H), 7.32 (s, 1H), 7.25–7.01 (m, 4H), 6.81 (s, 1H), 6.21 (s, 1H), 5.98 (s, 1H), 5.89 (m, 1H), 5.36–4.95 (br, 4H), 2.23–2.08 (m, 4H), 1.66–1.50 (m, 4H).

Anal. Calcd. for $C_{25}H_{23}ClN_2O+0.15C_4H_{10}O$: C, 72.52; H, 5.60; N, 6.77. Found: C, 72.46; H, 5.90; N, 6.45.

MS [(+)-APCI, m/z]: 403.2 [M+H]$^+$. Calcd. for $C_{25}H_{24}ClN_2O$: 403.1578.

EXAMPLE 11

(10,11-Dihydro-5H-pyrrolo[2,1-c][1,4]benzodiazepin-10-yl)-[2-chloro-4-(3,4-dihydro-naphthalen-1-yl)-phenyl]-methanone (10,11-Dihydro-5H-pyrrolo[2,1-c][1,4]benzodiazepin-10-yl)-[2-chloro-4-(4,4,5,5-tetramethyl-[1,3,2]dioxaborolan-2-yl)-phenyl]-methanone of Example 10, Step B (0.300 g, 0.668 mmol) and naphthalen-1-yl trifluoromethanesulfonate (0.205 g, 0.735 mmol) were reacted by the procedure described in Example 1, Step F. The crude product was purified by flash column chromatography on silica gel, eluting with 30% ethyl acetate in hexane to afford a clear oil. The oil was recrystallized from diethyl ether/petroleum ether to afford white crystals (0.290 g), m.p. 174–176° C.

$^1$H NMR (DMSO-$d_6$, 400 MHz): δ 7.60–7.47 (m, 1H), 7.40–7.29 (m, 2H), 7.23–7.01 (m, 7H), 6.82 (s, 1H), 6.58 (d, J=7.5, 1H), 6.07 (t, J=4.6, 1H), 6.00 (s, 1H), 5.90 (t, J=3.1, 1H), 5.30–4.90 (br, 4H), 2.73 (t, J=7.8, 2H), 2.32–2.27 (m, 2H).

Anal. Calcd. for $C_{29}H_{23}ClN_2O+0.15C_4H_{10}O$: C, 75.38; H, 5.02; N, 6.06. Found: C, 75.27; H, 5.35; N, 6.00.

MS [(+)-APCI, m/z]: 451.2 [M+H]$^+$. Calcd. for $C_{29}H_{24}ClN_2O$: 451.1578.

EXAMPLE 12

(10,11-Dihydro-5H-pyrrolo[2,1-c][1,4]benzodiazepin-10-yl)-[2-chloro-4-(6,6-dimethyl-cyclohex-1-en-1-yl)-phenyl]-methanone (10,11-Dihydro-5H-pyrrolo[2,1-c][1,4]benzodiazepin-10-yl)-[2-chloro-4-(4,4,5,5-tetramethyl-[1,3,2]dioxaborolan-2-yl)-phenyl]-methanone of Example 10, Step B (0.350 g, 0.780 mmol) and 6,6-dimethyl-cyclohex-1-en-1-yl trifluoromethanesulfonate (0.222 g, 0.858 mmol) were reacted by the procedure described in Example 1, Step F. The crude product was purified by flash column chromatography on silica gel, eluting with 30% ethyl acetate in hexane to afford a clear oil. The oil was dissolved in diethyl ether and precipitated with petroleum ether to afford a white solid (0.240 g).

$^1$H NMR (DMSO-$d_6$, 400 MHz): δ 7.57–7.45 (m, 1H), 7.36 (d, J=7.3, 1H), 7.21 (m, 1H), 7.09 (dt, J=1.5, 1H), 7.02–6.96 (m, 2H), 6.87 (d, J=7.7, 1H), 6.81 (t, J=2.0, 1H), 5.99 (s, 1H), 5.89 (t, J=3.1, 1H), 5.30 (t, J=3.6, 1H), 5.25 (br, 2H), 5.25–4.90 (br, 2H), 2.04–1.99 (m, 2H), 1.65–1.57 (m, 2H), 1.49–1.45 (m, 2H), 0.84 (s, 6H).

Anal. Calcd. for $C_{27}H_{27}ClN_2O$: C, 75.25; H, 6.31; N, 6.50. Found: C, 74.81; H, 6.47; N, 6.10.

MS [(+)-APCI, m/z]: 431.1 [M+H]$^+$. Calcd. for $C_{27}H_{28}ClN_2O$: 431.1888.

EXAMPLE 13

(10,11-Dihydro-5H-pyrrolo[2,1-c][1,4]benzodiazepin-10-yl)-[2-chloro-4-(2-methyl-3-oxo-cyclohex-1-en-1-yl)-phenyl]-methanone (10,11-Dihydro-5H-pyrrolo[2,1-c][1,4]benzodiazepin-10-yl)-[2-chloro-4-(4,4,5,5-tetramethyl-[1,3,2]dioxaborolan-2-yl)-phenyl]-methanone of Example 10, Step B (0.350 g, 0.780 mmol) and 2-methyl-3-oxo-cyclohex-1-en-1-yl trifluoromethanesulfonate (0.222 g, 0.858 mmol) were reacted by the procedure described in Example 1, Step F. The crude product was purified by flash column chromatography on silica gel, eluting with 50% ethyl acetate in hexane to afford an orange oil. The oil was dissolved in diethyl ether and precipitated with petroleum ether to afford orange solid (0.180 g).

$^1$H NMR (DMSO-$d_6$, 400 MHz): δ 7.37 (d, J=7.3, 2H), 7.29 (s, 1H), 7.13–7.00 (m, 4H), 6.81 (s, 1H), 5.99 (s, 1H), 5.90 (t, J=3.1, 1H), 5.35–4.90 (br, 4H), 2.51–2.44 (m, 2H), 2.36 (t, J=6.6, 2H), 1.92 (t, J=6.4, 2H), 1.40 (s, 3H).

Anal. Calcd. for $C_{26}H_{23}ClN_2O_2+0.15C_4H_8O_2$: C, 71.93; H, 5.49; N, 6.31. Found: C, 71.98; H, 5.88; N, 6.24.

MS [(+)-APCI, m/z]: 431.1 [M+H]$^+$. Calcd. for $C_{26}H_{24}ClN_2O_2$: 431.1528.

EXAMPLE 14

(10,11-Dihydro-5H-pyrrolo[2,1-c][1,4]benzodiazepin-10-yl)-[2-chloro-4-(3-hydroxy-2-methyl-cyclohex-1-en-1-yl)-phenyl]-methanone (10,11-Dihydro-5H-pyrrolo[2,1-c][1,4]benzodiazepin-10-yl)-[2-chloro-4-(2-methyl-3-oxo-cyclohex-1-en-1-yl)-phenyl]-methanone of Example 13 (0.060 g, 0.139 mmol) and cerium(III) chloride (0.034 g, 0.139 mmol) were dissolved in methanol (0.7 mL) followed by addition of solid sodium borohydride (0.0053 g, 0.139 mmol). Gas was vigorously evolved from the reaction mixture for approximately two minutes, after which 0.1 N hydrochloric acid (25 mL) was added. A white precipitate formed which was extracted with ethyl acetate. The combined extracts were dried over magnesium sulfate, concentrated and the residue purified by flash column chromatography on silica gel, eluting with 50% ethyl acetate in hexane. A clear oil was isolated which was dissolved in ether and precipitated with pentane to afford the title compound (0.050 g) as a white solid.

$^1$H NMR (DMSO-$d_6$, 400 MHz): δ 7.56–7.42 (m, 1H), 7.37 (d, J=7.5, 1H), 7.31–7.20 (m, 1H), 7.10–6.97 (m, 3H), 6.88 (d, J=7.5, 1H), 6.81 (s, 1H), 5.99 (s, 1H), 5.89 (t, J=3.0, 1H), 5.30–4.95 (br, 4H), 4.67 (br, 1H), 3.85 (s, 1H), 2.04 (s, 2H), 1.75–1.48 (m, 4H), 1.42 (s, 3H).

Anal. Calcd. for $C_{26}H_{25}ClN_2O_2+0.05C_4H_{10}O$: C, 71.52; H, 5.77; N, 6.42. Found: C, 71.28; H, 6.17; N, 5.99.

MS [(+)-APCI, m/z]: 433.1 [M+H]$^+$. Calcd. for $C_{26}H_{26}ClN_2O_2$ 433.1688.

EXAMPLE 15

(10,11-Dihydro-5H-pyrrolo[2,1-c][1,4]benzodiazepin-10-yl)-(4-cyclohex-1-en-1-yl-phenyl)-methanone Step A. 4-(Tri-n-butyl-stannyl)-benzoic acid ethyl ester Ethyl 4-bromobenzoate (20.0 g, 87.3 mmol), bis(tri-n-butyl)tin (66.2 mL, 131 mmol) and lithium chloride (11.1 g, 262 mmol) were combined in dioxane (175 mL) and the resulting suspension deoxygenated by sparging with nitrogen for 45 minutes. Tetrakis(triphenylphosphine)palladium (0) (1.01 g, 0.873 mmol) was added and the reaction refluxed for 18 hours. After cooling to room temperature, dioxane was evaporated and the residue taken up in ethyl acetate (400 mL) and filtered through celite. The filtrate was washed with 1 M potassium fluoride, pH 7 phosphate buffer and brine. The organic phase was then dried over anhydrous magnesium sulfate, filtered and concentrated. Purification of the residue by flash column chromatography on silica gel eluting with a solvent gradient of from 0 to 8% ethyl acetate in hexane afforded the title compound (31.2 g) as a clear oil.

$^1$H NMR (CDCl$_3$, 300 MHz): δ 7.97–7.93 (m, 2H), 7.55–7.50 (m, 2H), 4.36 (q, J=7.1, 2H), 1.69–1.48 (m, 6H), 1.40–1.24 (m, 15H), 0.91–0.83 (m, 9H).

Step B. 4-Cyclohex-1-en-1-yl-benzoic acid ethyl ester

Cyclohexen-1-yl trifluoromethanesulfonate (1.00 g, 4.34 mmol), lithium chloride (0.551 g, 13.0 mmol) and tris-dibenzylideneacetone di-palladium (0) (79.5 mg, 0.0868 mmol) were combined in anhydrous N-methylpyrrolidinone (20 mL) and the resulting solution deoxygenated by sparging with nitrogen for 30 minutes. To the catalyst solution was added a solution of 4-(tri-n-butyl-stannyl)-benzoic acid ethyl ester of Step A (2.10 g, 4.77 mmol) in anhydrous N-methylpyrrolidinone (9 mL). The reaction was stirred at room temperature for 38 hours, followed by addition of 1 M potassium fluoride (5 mL). After stirring for 3 hours, the reaction mixture was diluted with ethyl acetate (200 mL) and filtered through celite. The filtrate was washed with 1 M potassium fluoride, water and brine. The organic phase was dried over anhydrous magnesium sulfate, filtered and concentrated. The residue was purified by flash column chromatography on silica gel, eluting with a solvent gradient of from 0 to 10% ethyl acetate in hexane. A solid was isolated which was recrystallized from pentane (−20° C.) to afford the title compound (0.608 g) as a white solid, m.p. 66° C.

$^1$H NMR (DMSO-d$_6$, 400 MHz): δ 7.89–7.87 (m, 2H), 7.54–7.51 (m, 2H), 6.33–6.31 (m, 1H), 4.29 (q, J=7.0, 2H), 2.39–2.35 (m, 2H), 2.22–2.17 (m, 2H), 1.75–1.69 (m, 2H), 1.63–1.57 (m, 2H), 1.39 (t, J=7.1, 3H).

Anal. Calcd. for C$_{15}$H$_{18}$O$_2$+0.07H$_2$O: C, 77.80; H, 7.90. Found: C, 77.51; H, 7.90.

MS [EI, m/z]: 230 [M]$^+$. Calcd. for C$_{15}$H$_{18}$O$_2$: 230.131.

Step C. 4-Cyclohex-1-en-1-yl-benzoic acid

4-Cyclohex-1-en-1-yl-benzoic acid ethyl ester of Step B (0.153 g, 0.756 mmol) was dissolved in methanol (10 mL) followed by addition of solid sodium hydroxide (0.060 g, 1.51 mmol), and the resulting mixture was refluxed overnight. After cooling to room temperature, methanol was evaporated and the residue dissolved in water (50 mL). The aqueous phase was washed with diethyl ether and the organic washings discarded. Acidification of the aqueous phase with 1 N hydrochloric acid resulted in the precipitation of a white solid, which was filtered and dried in vacuo to afford the title compound (0.110 g) as a white solid.

$^1$H NMR (DMSO-d$_6$, 400 MHz): δ 7.87–7.82 (m, 2H), 7.49–7.46 (m, 2H), 6.30–6.27 (m, 1H), 2.39–2.35 (m, 2H), 2.22–2.16 (m, 2H), 1.75–1.69 (m, 2H), 1.62–1.55 (m, 2H) [carboxylic acid proton is not observed.]

MS [(−)-ESI, m/z]: 201.1 [M−H]$^−$. Calcd. for C$_{13}$H$_{13}$O$_2$: 201.0912.

Step D. (10,11-Dihydro-5H-pyrrolo[2,1-c][1,4]benzodiazepin-10-yl)-(4-cyclohex-1-en-1-yl-phenyl)-methanone 4-Cyclohex-1-en-1-yl-benzoic acid of Step C (0.099 g, 0.489 mmol) and oxalyl chloride (0.065 g, 0.513 mmol) were dissolved in anhydrous methylene chloride (5 mL) and N,N-dimethylformamide (0.00114 mL, 0.0147 mmol) added. The resulting mixture was refluxed for 1 hour, then cooled to room temperature and solvent evaporated. The crude acid chloride thus prepared was combined with 10,11-dihydro-5H-pyrrolo[2,1-c][1,4]benzodiazepine (0.090 g, 0.489 mmol) and N,N-diisopropyl ethylamine (0.103 mL, 0.589 mmol) in anhydrous dichloromethane (5 mL). After stirring at room temperature for 1.5 hours, 1 N hydrochloric acid (50 mL) was added and the resulting mixture extracted with diethyl ether (50 mL). The organic phase was washed with 1 N hydrochloric acid, 1 N sodium hydroxide and brine. The organic phase was dried over anhydrous magnesium sulfate, filtered and concentrated, and the residue purified by flash column chromatography on silica gel, eluting with 20% ethyl acetate in hexane. A slightly orange solid was isolated which was recrystallized from petroleum ether to afford the title compound (0.131 g) as white crystals, m.p. 156° C.

$^1$H NMR (DMSO-d$_6$, 400 MHz): δ 7.35 (dd, J=1.5, 7.5, 1H), 7.27–7.19 (m, 4H), 7.15 (dt, J=1.2, 7.7, 1H), 7.08 (t, J=7.5, 1H), 6.85 (br, 1H), 6.68 (dd, J=1.8, 2.5, 1H), 6.15–6.12 (m, 1H), 6.08 (dd, J=1.6, 3.5, 1H), 6.03 (br, 1H), 5.19 (br, 4H), 2.34–2.29 (m, 2H), 2.21–2.15 (m, 2H), 1.77–1.71 (m, 2H), 1.65–1.59 (m, 2H).

Anal. Calcd. for C$_{25}$H$_{24}$N$_2$O: C, 81.49; H, 6.57; N, 7.60. Found: C, 81.01; H, 6.68; N, 7.35.

MS [(+)-ESI, m/z]: 369.2 [M+H]$^+$. Calcd. for C$_{25}$H$_{25}$N$_2$O: 369.1968.

EXAMPLE 16

(10,11-Dihydro-5H-pyrrolo[2,1-c][1,4]benzodiazepin-10-yl)-[4-(6-methyl-cyclohex-1-en-1-yl)-phenyl]-methanone Step A. 4-(6-Methyl-cyclohexen-1-yl)benzoic acid, methyl ester The title compound was prepared in the manner of Example 15, Step B and isolated as an amorphous white solid.

$^1$H NMR (DMSO-d$_6$, 400 MHz): δ 7.91–7.87 (m, 2H), 7.48–7.44 (m, 2H), 6.03 (dt, J=1.1, 4.0, 1H), 3.83 (s, 3H), 2.91–2.87 (m, 1H), 2.17–2.13 (m, 2H), 1.84–1.77 (m, 1H), 1.68–1.50 (m, 3H), 0.87 (d, J=7.0, 3H).

Anal. Calcd. for C$_{15}$H$_{18}$O$_2$: C, 78.23; H, 7.88. Found: C, 78.23; H, 7.79.

MS [(+)-APCI, m/z]: 231.0 [M+H]$^+$. Calcd. for C$_{15}$H$_{19}$O$_2$: 231.1386.

Step B. 4-(6-Methyl-cyclohex-1-en-1-yl)-benzoic acid 4-(6-Methyl-cyclohex-1-en-1-yl)-benzoic acid methyl ester of Step A (0.108 g, 0.469 mmol) was saponified in the manner of Example 15, Step C to provide the title compound (0.100 g) as a white, crystalline solid, m.p. 146–147° C.

$^1$H NMR (DMSO-d$_6$, 400 MHz): δ 12.78 (s, 1H), 7.89–7.85 (m, 2H), 7.44–7.41 (m, 2H), 6.02 (t, J=3.7, 1H), 2.90–2.86 (m, 1H), 2.17–2.13 (m, 2H), 1.85–1.77 (m, 1H), 1.68–1.50 (m, 3H), 0.87 (d, J=7.0, 3H).

Anal. Calcd. for C$_{14}$H$_{16}$O$_2$: C, 77.75; H, 7.46. Found: C, 77.74; H, 7.61.

MS [(−)-APCI, m/z]: 215.1 [M−H]$^−$. Calcd. for C$_{14}$H$_{15}$O$_2$: 215.1073.

Step C. (10,11-Dihydro-5H-pyrrolo[2,1-c][1,4]benzodiazepin-10-yl)-[4-(6-methyl-cyclohex-1-en-1-yl)-phenyl]-methanone 4-(6-Methyl-cyclohex-1-en-1-yl)-benzoic acid of Step B (0.070 g, 0.324 mmol) and 10,11-dihydro-5H-pyrrolo[2,1-c][1,4]benzodiazepine (0.066 g, 0.356 mmol) were reacted in the manner of Example 15, Step D. The title compound was purified by recrystallization from a mixture of diethyl ether and petroleum ether to afford 0.120 g of white crystals, m.p. 108–109° C.

$^1$H NMR (DMSO-$d_6$, 400 MHz): δ 7.46 (dd, J=1.3, 7.5, 1H), 7.20–7.14 (m, 5H), 7.07 (dt, J=0.9, 7.7, 1H), 6.88 (d, J=7.5, 1H), 6.81 (t, J=2.4, 1H), 5.95 (s, 1H), 5.91 (t, J=3.5, 1H), 5.89 (t, J=3.7, 1H), 5.40–4.65 (br, 4H), 2.78–2.74 (m, 1H), 2.10–2.07 (m, 2H), 1.77–1.70 (m, 1H), 1.63–1.44 (m, 3H), 0.77 (d, J=7.0, 3H).

Anal. Calcd. for $C_{26}H_{26}N_2O$: C, 81.64; H, 6.85; N, 7.32. Found: C, 81.14; H, 7.17; N, 7.25.

MS [(+)-APCI, m/z]: 383.1 [M+H]$^+$. Calcd. for $C_{26}H_{27}N_2O$: 383.2125.

EXAMPLE 17

(10,11-Dihydro-5H-pyrrolo[2,1-c][1,4]benzodiazepin-10-yl)-[4-(6,6-dimethyl-cyclohex-1-en-1-yl)-phenyl]-methanone Step A. 4-(6,6-Dimethyl-cyclohex-1-en-1-yl)-benzoic acid ethyl ester 4-(Tri-n-butyl-stannyl)-benzoic acid ethyl ester of Example 15, Step A (3.20 g, 7.28 mmol) and 6,6-dimethyl-cyclohex-1-en-1-yl trifluoromethanesulfonate (1.71 g, 6.62 mmol) were reacted in the manner of Example 15, Step B. Purification by flash column chromatography on silica gel, eluting with a solvent gradient of from 0 to 5% ethyl acetate in hexane afforded the title compound (1.18 g) as a clear oil.

$^1$H NMR (CDCl$_3$, 400 MHz): δ 7.98–7.93 (m, 2H), 7.23–7.19 (m, 2H), 5.44 (t, J=3.7, 1H), 4.37 (q, J=7.0, 2H), 2.14–2.10 (m, 2H), 1.77–1.70 (m, 2H), 1.61–1.55 (m, 2H), 1.39 (t, J=7.0, 3H), 1.02 (s, 6H).

Anal. Calcd. for $C_{17}H_{22}O_2$+0.10$H_2O$: C, 78.49; H, 8.60. Found: C, 78,14; H, 8.61.

Step B. 4-(6,6-Dimethyl-cyclohex-1-en-1-yl)-benzoic acid 4-(6,6-Dimethyl-cyclohex-1-en-1-yl)-benzoic acid methyl ester of Step A (0.900 g, 3.48 mmol) was saponified in the manner of Example 15, Step C to provide the title compound (0.570 g) as a white crystalline solid, m.p. 181° C.

$^1$H NMR (DMSO-$d_6$, 400 MHz): δ 12.75 (br, 1H), 7.89–7.83 (m, 2H), 7.26–7.21 (m, 2H), 5.41 (t, J=3.7, 1H), 2.10–2.06 (m, 2H), 1.71–1.65 (m, 2H), 1.55–1.52 (m, 2H), 0.98 (s, 6H).

Anal. Calcd. for $C_{15}H_{18}O_2$: C, 78.23; H, 7.88. Found: C, 68.68; H, 6.98.

MS [EI, m/z]: 230 [M]$^+$. Calcd. for $C_{15}H_{18}O_2$: 230.131.

Step C. (10,11-Dihydro-5H-pyrrolo[2,1-c][1,4]benzodiazepin-10-yl)-[4-(6,6-dimethyl-cyclohex-1-en-1-yl)-phenyl]-methanone 4-(6,6-Dimethyl-cyclohex-1-en-1-yl)-benzoic acid of Step B (0.235 g, 1.02 mmol) and 10,11-dihydro-5H-pyrrolo[2,1-c][1,4]benzodiazepine (0.205 g, 1.11 mmol) were reacted in the manner of Example 15, Step D. Purification by flash column chromatography on silica gel, eluting with 20% ethyl acetate in hexane, followed by recrystallization from petroleum ether afforded the title compound (0.346 g) as white crystals, m.p. 118° C.

$^1$H NMR (DMSO-$d_6$, 400 MHz): δ 7.45 (dd, J=1.5, 7.5, 1H), 7.18–7.14 (m, 3H), 7.06 (t, J=7.3, 1H), 6.94 (d, J=8.1, 2H), 6.87 (d, J=7.7, 1H), 6.81 (t, J=2.2, 1H), 5.94 (s, 1H), 5.91 (t, J=3.1, 1H), 5.29 (t, J=3.7, 1H), 5.29–4.80 (br, 4H), 2.05–2.01 (m, 2H), 1.65–1.62 (m, 2H), 1.49–1.46 (m, 2H), 0.87 (s, 6H).

Anal. Calcd. for $C_{27}H_{28}N_2O$: C, 81.78; H, 7.12; N, 7.06. Found: C, 81.52; H, 7.07; N, 6.99.

MS [EI, m/z]: 396 [M]$^+$. Calcd. for $C_{27}H_{28}N_2O$: 396.220.

EXAMPLE 18

(10,11-Dihydro-5H-pyrrolo[2,1-c][1,4]benzodiazepin-10-yl)-[4-(3,4-dihydro-naphthalen-1-yl)-phenyl]-methanone Step A. 4-(3,4-Dihydro-naphthalen-1-yl)-benzoic acid ethyl ester 4-(Tri-n-butyl-stannyl)-benzoic acid ethyl ester of Example 15, Step A (2.58 g, 5.88 mmol) and 3,4-dihydro-naphthalen-1-yl trifluoromethanesulfonate (1.80 g, 6.47 mmol) were reacted in the manner of Example 15, Step B. Purification by flash column chromatography on silica gel, eluting with a solvent gradient of from 0 to 10% ethyl acetate in hexane followed by recrystallization from pentane (−20° C.) afforded the title compound (1.53 g) as slightly yellow crystals, m.p. 81° C.

$^1$H NMR (DMSO-$d_6$, 400 MHz): δ 8.07–8.04 (m, 2H), 7.44–7.41 (m, 2H), 7.22–7.20 (m, 1H), 7.17 (dt, J=1.3, 7.0, 1H), 7.11 (dt, J=1.8, 7.4, 1H), 6.95 (dd, J=1.1, 7.5, 1H), 6.15 (t, J=4.6, 1H), 4.40 (q, J=7.1, 2H), 2.86 (t, J=8.0, 2H), 2.46–2.41 (m, 2H), 1.41 (t, J=7.0, 3H).

Anal. Calcd. for $C_{19}H_{18}O_2$+0.17$H_2O$: C, 81.09; H, 6.57. Found: C, 81.08; H, 6.63.

MS [EI, m/z]: 278 [M]$^+$. Calcd. for $C_{19}H_{18}O_2$: 278.131.

Step B. 4-(3,4-Dihydro-naphthalen-1-yl)-benzoic acid 4-(3,4-Dihydro-naphthalen-1-yl)-benzoic acid ethyl ester of Step A (0.700 g, 2.51 mmol) was saponified in the manner of Example 15, Step C to provide the title compound (0.392 g) as a white solid.

Step C. (10,11-Dihydro-5H-pyrrolo[2,1-c][1,4]benzodiazepin-10-yl)-[4-(3,4-dihydro-naphthalen-1-yl)-phenyl]-methanone 4-(3,4-Dihydro-naphthalen-1-yl)-benzoic acid of Step B (0.280 g, 1.12 mmol) and 10,11-dihydro-5H-pyrrolo[2,1-c][1,4]benzodiazepine (0.227 g, 1.23 mmol) were reacted in the manner of Example 15, Step D. Recrystallization from petroleum ether afforded the title compound (0.238 g) as white crystals, m.p. 166° C.

$^1$H NMR (DMSO-$d_6$, 400 MHz): δ 7.46 (dd, J=1.1. 7.2, 1H), 7.29 (d, J=8.1, 2H), 7.21–7.06 (m, 7H), 6.95 (d, J=7.2, 1H), 6.82 (t, J=2.1, 1H), 6.68 (d, J=7.5, 1H), 6.05 (t, J=4.6, 1H), 5.96 (s, 1H), 5.92 (t, J=2.9, 1H), 5.40–4.75 (br, 4H), 2.74 (t, J=7.9, 2H), 2.33–2.28 (m, 2H).

Anal. Calcd. for $C_{29}H_{24}N_2O$+0.20$H_2O$: C, 82.91; H, 5.85; N, 6.67. Found: C, 82.97; H, 5.95; N, 6.78.

MS [(+)-APCI, m/z]: 417.0 [M+H]$^+$. Calcd. for $C_{29}H_{25}N_2O$: 417.1968.

EXAMPLE 19

(10,11-Dihydro-5H-pyrrolo[2,1-c][1,4]benzodiazepin-10-yl)-[4-(2,6-dimethyl-cyclohex-1-en-1-yl)-phenyl]-methanone Step A. (10,11-Dihydro-5H-pyrrolo[2,1-c][1,4]benzodiazepin-10-yl)-(4-bromo-phenyl)-methanone 10,11-Dihydro-5H-pyrrolo[2,1-c][1,4]benzodiazepine (8.83 g, 47.9 mmol) and 4-bromobenzoyl chloride (10.0 g, 45.6 mmol) were dissolved in anhydrous dichloromethane (240 mL) followed by addition of N,N-diisopropylethyl amine (8.74 mL, 50.2 mmol) dropwise over the course of 30 minutes. After stirring at room temperature for four hours, the reaction mixture was washed with 1 N hydrochloric acid, 1 N sodium hydroxide and brine, dried over anhydrous magnesium sulfate, filtered and concentrated. Recrystallization of the residue from ethyl acetate afforded the title compound (15.4 g) as white crystals.

$^1$H NMR (DMSO-$d_6$, 400 MHz): δ 7.46–7.41 (m, 3H), 7.22–7.15 (m, 3H), 7.09 (t, J=7.5, 1H), 6.91 (d, J=7.2, 1H), 6.81 (dd, J=2.0, 2.4, 1H), 5.95 (s, 1H), 5.91 (dd, J=2.8, 3.5, 1H), 5.45-4.65 (br, 4H).

Anal. Calcd. for $C_{19}H_{15}BrN_2O$: C, 62.14; H, 4.12; N, 7.63. Found: C, 62.08; H, 3.99; N, 7.57.

MS [(+)-ESI, m/z]: 367.0 [M+H]$^+$. Calcd. for $C_{19}H_{16}BrN_2O$: 367.0448.

Step B. (10,11-Dihydro-5H-pyrrolo[2,1-c][1,4]benzodiazepin-10-yl)-[4-(4,4,5,5-tetramethyl-[1,3,2]dioxaborolan-2-yl)-phenyl]-methanone (10,11-Dihydro-5H-pyrrolo[2,1-c][1,4]benzodiazepin-10-yl)-(4-bromo-phenyl)-methanone of Step A (2.00 g, 5.45 mmol) and bis(pinacolato)diboron (1.52 g, 6.0 mmol) were reacted in the manner of Example 1, Step E. After aqueous work-up and concentration the residue was purified by trituration with diethyl ether to afford the title compound (1.65 g) as a light brown solid, m.p. 214–217° C. (dec.)

$^1$H NMR (DMSO-$d_6$, 400 MHz): δ 7.48 (d, J=7.7, 2H), 7.44 (dd, J=1.3, 7.7, 1H), 7.26 (d, J=7.9, 2H), 7.15 (t, J=7.5, 1H), 7.09–7.02 (m, 1H), 6.89 (br, 1H), 6.81 (t, J=2.4, 1H), 5.94 (s, 1H), 5.91 (t, J=3.1, 1H), 5.40–4.75 (br, 4H), 1.25 (s, 12H).

Anal. Calcd. for $C_{25}H_{27}BN_2O_3+0.12C_4H_8O_2$: C, 72.03; H, 6.63; N, 6.59. Found: C, 71.03; H, 6.44; N, 6.54.

MS [(+)-ESI, m/z]: 415.1 [M+H]$^+$. Calcd. for $C_{25}H_{28}BN_2O_3$ 415.2198.

Step C. (10,11-Dihydro-5H-pyrrolo[2,1-c][1,4]benzodiazepin-10-yl)-[4-(2,6-dimethyl-cyclohex-1-en-1-yl)-phenyl]-methanone (10,11-Dihydro-5H-pyrrolo[2,1-c][1,4]benzodiazepin-10-yl)-[4-(4,4,5,5-tetramethyl-[1,3,2]dioxaborolan-2-yl)-phenyl]-methanone of Step B (0.300 g, 0.746 mmol) and 2,6-dimethyl-cyclohex-1-en-1-yl trifluoromethanesulfonate (0.255 g, 0.821 mmol) were reacted by the procedure described in Example 1, Step F. Purification by flash column chromatography on silica gel, eluting with a solvent gradient of from 30 to 60% ethyl acetate in hexane, followed by recrystallization from petroleum ether (−20° C.) afforded the title compound as white crystals, m.p. 153–154° C.

$^1$H NMR (DMSO-$d_6$, 400 MHz): δ 7.44 (dd, J=1.3, 7.5, 1H), 7.19 (d, J=8.4, 2H), 7.14 (dt, J=1.1, 7.5, 1H), 7.02 (t, J=7.7, 1H), 6.90–6.85 (m, 3H), 6.81 (dd, J=2.0, 2.6, 1H), 5.95 (m, 1H), 5.91 (dd, J=2.6, 3.5, 1H), 5.40–4.80 (br, 4H), 2.41–2.36 (m, 1H), 2.03–1.90 (m, 2H), 1.76–1.69 (m, 1H), 1.64–1.52 (m, 2H), 1.44–1.38 (m, 1H), 1.33 (s, 3H), 0.61 (d, J=7.0, 3H).

Anal. Calcd. for $C_{27}H_{28}N_2O+0.30C_6H_{14}+0.05C_4H_{10}O$: C, 81.10; H, 7.62; N, 6.57. Found: C, 80.94; H, 7.76; N, 6.32.

MS [(+)-APCI, m/z]: 397.2 [M+H]$^+$. Calcd. for $C_{27}H_{29}N_2O$: 397.2281.

EXAMPLE 20

(10,11-5H-Dihydro-pyrrolo[2,1-c][1,4]benzodiazepin-10-yl)-[4-(6-tert-butyl-cyclohex-1-en-1-yl)-phenyl]-methanone Step A. 4-(6-tert-Butyl-cyclohex-1-en-1-yl)-benzoic acid ethyl ester 4-(Tri-n-butyl-stannyl)-benzoic acid ethyl ester of Example 15, Step A (2.00 g, 4.55 mmol) and 6-tert-butyl-cyclohex-1-en-1-yl trifluoromethanesulfonate (1.43 g, 5.01 mmol) were reacted by the procedure described in Example 15, Step B. Purification by flash column chromatography on silica gel, eluting with a solvent gradient of from 0 to 10% ethyl acetate in hexane followed by recrystallization from methanol (0° C.) afforded the title compound (0.870 g) as white crystals, m.p. 50° C.

$^1$H NMR (CDCl$_3$, 400 MHz): δ 7.94 (d, J=8.1, 2H), 7.30 (d, J=8.3, 2H), 5.90 (t, J=4.2, 1H), 4.36 (q, J=7.2, 2H), 2.69–2.66 (m, 1H), 2.20–2.15 (m, 2H), 1.99–1.93 (m, 1H), 1.86–1.66 (m, 2H), 1.61–1.52 (m, 1H), 1.39 (t, J=7.2, 3H), 0.75 (s, 9H).

Anal. Calcd. for $C_{19}H_{26}O_2$: C, 79.68; H, 9.15. Found: C, 79.86; H, 9.46.

MS [EI, m/z]: 286 [M]$^+$. Calcd. for $C_{19}H_{26}O_2$ 286.193.

Step B. 4-(6-tert-Butyl-cyclohex-1-en-1-yl)-benzoic acid 4-(6-tert-Butyl-cyclohex-1-en-1-yl)-benzoic acid ethyl ester of Step A (0.300 g, 1.05 mmol) was saponified in the manner of Example 15, Step C. The title compound (0.272 g) was isolated as a white solid which was recrystallized from diethyl ether/petroleum ether, m.p. 197° C.

$^1$H NMR (DMSO-$d_6$, 400 MHz): δ 12.73 (s, 1H), 7.85–7.82 (m, 2H), 7.37–7.34 (m, 2H), 5.88 (t, J=4.0, 1H), 2.73–2.71 (m, 1H), 2.23–2.05 (m, 2H), 1.94–1.87 (m, 1H), 1.79–1.60 (m, 2H), 1.55–1.46 (m, 1H), 0.72 (s, 9H).

Anal. Calcd. for $C_{17}H_{22}O_2$: C, 79.03; H, 8.58. Found: C, 78.90; H, 8.68.

MS [EI, m/z]: 258 [M]$^+$. Calcd. for $C_{17}H_{22}O_2$: 258.162.

Step C. (10,11-5H-Dihydro-pyrrolo[2,1-c][1,4]benzodiazepin-10-yl)-[4-(6-tert-butyl-cyclohex-1-en-1-yl)-phenyl]-methanone 4-(6-tert-Butyl-cyclohex-1-en-1-yl)-benzoic acid of Step B (0.109 g, 0.422 mmol) and 10,11-dihydro-5H-pyrrolo[2,1-c][1,4]benzodiazepine (0.085 g, 0.464 mmol) were reacted in the manner of Example 15, Step D. Recrystallization from petroleum ether afforded the title compound (0.152 g) as white crystals, m.p. 142° C.

$^1$H NMR (DMSO-$d_6$, 400 MHz): δ 7.43 (dd, J=1.1, 7.5, 1H), 7.16–7.06 (m, 5H), 6.98 (t, J=7.4, 1H), 6.84–6.80 (m, 2H), 5.94 (s, 1H), 5.90 (dd, J=2.7, 3.4, 1H), 5.73 (t, J=4.0, 1H), 5.35–4.80 (br, 4H), 2.57–2.53 (m, 1H), 2.16–1.98 (m, 2H), 1.87–1.80 (m, 1H), 1.73–1.52 (m, 2H), 1.50–1.41 (m, 1H), 0.61 (s, 9H).

Anal. Calcd. for $C_{29}H_{32}N_2O+0.50H_2O$: C, 80.33; H, 7.67; N, 6.46. Found: C, 80.64; H, 7.58; N, 6.53.

MS [EI, m/z]: 424 [M]$^+$. Calcd. for $C_{29}H_{32}N_2O$: 424.252.

EXAMPLE 21

(10,11-Dihydro-5H-pyrrolo[2,1-c[1,4]benzodiazepin-10-yl)-(4-bicyclo[3.2.1]oct-2-en-2-yl-phenyl)-methanone Step A. 4-Bicyclo[3.2.1]oct-2-en-2-yl-benzoic acid ethyl ester 4-(Tri-n-butyl-stannyl)-benzoic acid ethyl ester of Example 15, Step A (1.82 g, 4.15 mmol) and bicyclo[3.2.1]oct-2-en-2-yl trifluoromethanesulfonate (1.17 g, 4.57 mmol) were reacted in the manner of Example 15, Step B. Purification by flash column chromatography on silica gel, eluting with a solvent gradient of from 0 to 10% ethyl acetate in hexane afforded the crude title compound a yellow oil.

Step B. 4-Bicyclo[3.2.1]oct-2-en-2-yl-benzoic acid

The 4-bicyclo[3.2.1]oct-2-en-2-yl-benzoic acid ethyl ester of Step A was saponified in the manner of Example 15, Step C. Recrystallization from petroleum ether afforded 0.642 g of the title compound as white crystals, m.p. 180–181° C.

$^1$H NMR (DMSO-$d_6$, 400 MHz): δ 12.80 (br, 1H), 7.86 (d, J=7.3, 2H), 7.48 (d, J=7.6, 2H), 5.93 (t, J=3.7, 1H), 2.89 (br, 1H), 2.53–2.45 (m, 1H), 2.37 (br, 1H), 2.01 (dd, J=3.6, 9.5, 1H), 1.92–1.79 (m, 3H), 1.66–1.58 (m, 2H), 1.47–1.40 (m, 1H).

Anal. Calcd. for $C_{15}H_{16}O_2$: C, 78.92; H, 7.06. Found: C, 79.01; H, 7.09.

MS [(−)-APCI, m/z]: 227.1 [M−H]$^−$. Calcd. for $C_{15}H_{15}O_2$: 227.1072.

Step C. (10,11-Dihyro-5H-pyrrolo[2,1-c][1,4]benzodiazepin-10-yl)-(4-bicyclo[3.2.1]oct-2-en-2-yl-phenyl)-methanone 4-Bicyclo[3.2.1]oct-2-en-2-yl-benzoic acid of Step B (0.270 g, 1.18 mmol) and 10,11-dihydro-5H-pyrrolo[2,1-c][1,4]benzodiazepine (0.240 g, 1.30 mmol) were reacted in the manner of Example 15, Step D. Purification by flash column chromatography on silica gel, eluting with 20% ethyl acetate in hexane, followed by recrystallization from petroleum ether afforded the title compound (0.401 g) as white crystals, m.p. 157° C.

$^1$H NMR (DMSO-$d_6$, 400 MHz): δ 7.46 (dd, J=1.5, 7.5, 1H), 7.24–7.15 (m, 5H), 7.10 (dt, J=1.5, 7.6, 1H), 6.92–6.88 (m, 1H), 6.81 (t, J=2.3, 1H), 5.94 (s, 1H), 5.92 (t, J=3.7, 1H), 5.79 (t, J=3.5, 1H), 5.35–4.75 (br, 4H), 2.78 (br, 1H), 2.47–2.39 (m, 1H), 2.36–2.30 (m, 1H), 1.99–1.92 (m, 1H), 1.88–1.70 (m, 2H), 1.61–1.53 (m, 2H), 1.48–1.36 (m, 1H), 1.24–1.18 (m, 1H).

Anal. Calcd. for $C_{27}H_{26}N_2O$: C, 82.20; H, 6.64; N, 7.10. Found: C, 81.84; H, 6.81; N, 6.97.

MS [(+)-ESI, m/z]: 394.9 [M+H]$^+$. Calcd. for $C_{27}H_{27}N_2O$: 395.2148.

EXAMPLE 22

(10,11-Dihydro-5H-pyrrolo[2,1-c][1,4]benzodiazepin-10-yl)-[4-(6,6-dimethyl-bicyclo[3.1.1]hept-2-en-2-yl)-phenyl]-methanone Step A. 4-(6,6-Dimethyl-bicyclo[3.1.1]hept-2-en-2-yl)-benzoic acid ethyl ester 4-(Tri-n-butyl-stannyl)-benzoic acid ethyl ester of Example 15, Step A (1.45 g, 3.30 mmol) and 6,6-dimethyl-bicyclo[3.1.1]hept-2-en-2-yl trifluoromethanesulfonate (0.981 g, 3.63 mmol) were reacted in the manner of Example 15, Step B. Purification by flash column chromatography on silica gel, eluting with a solvent gradient of from 0 to 5% ethyl acetate in hexane afforded the crude title compound a yellow oil.

Step B. 4-(6,6-Dimethyl-bicyclo[3.1.1]hept-2-en-2-yl)-benzoic acid

The 4-(6,6-dimethyl-bicyclo[3.1.1]hept-2-en-2-yl)-benzoic acid ethyl ester of Step A (0.470 g, 1.74 mmol) was saponified in the manner of Example 15, Step C. Recrystallization from a mixture of diethyl ether and petroleum ether afforded the title compound (0.300 g) as white crystals.

$^1$H NMR (DMSO-$d_6$, 400 MHz): δ 12.80 (br, 1H), 7.87–7.82 (m, 2H), 7.43–7.40 (m, 2H), 6.07 (br, 1H), 2.71 (t, J=4.8, 1H), 2.62 (t, J=7.7, 1H), 2.43 (t, J=3.1, 1H), 2.37 (t, J=3.0, 1H), 2.15 (m, 2H), 1.35 (s, 3H), 0.82 (s, 3H).

MS [(−)-APCI, m/z]: 241.1 [M−H]$^−$. Calcd. for $C_{16}H_{17}O_2$: 241.1232.

Step C. (10,11-Dihydro-5H-pyrrolo[2,1-c][1,4]benzodiazepin-10-yl)-[4-(6,6-dimethyl-bicyclo[3.1.1]hept-2-en-2-yl)-phenyl]-methanone 4-(6,6-dimethyl-bicyclo[3.1.1]hept-2-en-2-yl)-benzoic acid of Step B (0.160 g, 0.66 mmol) and 10,11-dihydro-5H-pyrrolo[2,1-c][1,4]benzodiazepine (0.134 g, 0.726 mmol) were reacted in the manner of Example 15, Step D. Purification by flash column chromatography on silica gel, eluting with 20% ethyl acetate in hexane, followed by recrystallization from petroleum ether afforded the title compound (0.200 g) as white crystals, m.p. 118–119° C.

$^1$H NMR (DMSO-$d_6$, 400 MHz): δ 7.48 (m, 1H), 7.22–7.01 (m, 6H), 6.93–6.87 (m, 1H), 6.81 (t, J=2.4, 1H), 5.93–5.90 (m, 3H), 5.30–4.80 (br, 4H), 2.61 (dt, J=1.3, 5.5, 1H), 2.46–2.41 (m, 2H), 2.37 (t, J=3.1, 1H), 2.32 (t, J=3.0, 1H), 2.13–2.10 (m, 1H), 1.31 (s, 3H), 0.77 (s, 3H).

Anal. Calcd. for $C_{28}H_{28}N_2O+0.25H_2O$: C, 81.42; H, 6.95; N, 6.78. Found: C, 81.25; H, 6.99; N, 6.91.

MS [(+)-ESI, m/z]: 409.1 [M+H]$^+$. Calcd. for $C_{28}H_{29}N_2O$: 409.2282.

EXAMPLE 23

(10,11-Dihydro-5H-pyrrolo[2,1-c][1,4]benzodiazepin-10-yl)-[4-(3,3,5,5-tetramethyl-cyclohex-1-en-1-yl)-phenyl]-methanone (10,11-Dihydro-5H-pyrrolo[2,1-c][1,4]benzodiazepin-10-yl)-[4-(4,4,5,5-tetramethyl-1,3,2]dioxaborolan-2-yl)-phenyl]-methanone of Example 19 Step B (0.250 g, 0.62 mmol) and 3,3,5,5-tetramethyl-cyclohex-1-en-1-yl trifluoromethanesulfonate (0.212 g, 0.74 mmol) were reacted in the manner of Example 1, Step F. Purification by flash column chromatography on silica gel, eluting with 20% ethyl acetate in hexane, followed by recrystallization from petroleum ether afforded the title compound (0.080 g) as white crystals, m.p. 142–143° C.

$^1$H NMR (DMSO-$d_6$, 400 MHz): δ 7.47 (d, J=7.3, 1H), 7.25–7.20 (m, 4H), 7.18 (t, J=7.3, 1H), 7.11 (t, J=7.5, 1H), 6.91 (d, J=7.3, 1H), 6.81 (t, J=1.9, 1H), 5.94 (s, 1H), 5.91 (dt, J=0.6, 3.5, 1H), 5.84 (s, 1H), 5.36–4.80 (br, 4H), 2.02 (s, 2H), 1.33 (s, 2H), 1.02 (s, 6H), 0.94 (s, 6H).

Anal. Calcd. for $C_{29}H_{32}N_2O$: C, 82.04; H, 7.60; N, 6.60. Found: C, 81.77; H, 7.72; N, 6.47.

MS [(+)-ESI, m/z]: 425.5 [M+H]$^+$. Calcd. for $C_{29}H_{33}N_2O$: 425.2598.

EXAMPLE 24

3-[4-(10,11-Dihydro-5H-pyrrolo[2,1-c][1,4]benzodiazepine-10-carbonyl)-phenyl]-cyclohex-2-en-1-one (10,11-Dihydro-5H-pyrrolo[2,1-c][1,4]benzodiazepin-10-yl)-[4-(4,4,5,5-tetramethyl-[1,3,2]dioxaborolan-2-yl)-phenyl]-methanone of Example 19, Step B (0.500 g, 1.24 mmol) and 3-oxo-cylclohex-1-en-1-yl trifluoromethanesulfonate (0.332 g, 1.36 mmol) were reacted in the manner of Example 1, Step F. Purification by flash column chromatography on silica gel, eluting with 50% ethyl acetate in hexane, followed by recrystallization from a mixture of diethyl ether and petroleum ether afforded the title compound (0.320 g) as light yellow crystals, m.p. 205–207° C.

$^1$H NMR (DMSO-$d_6$, 400 MHz): δ 7.51 (d, J=8.4, 2H), 7.46 (dd, J=1.3, 7.5, 1H), 7.32 (d, J=8.2, 2H), 7.16 (dt, J=1.1, 7.5, 1H), 7.08 (t, J=7.5, 1H), 6.93 (d, J=7.3, 1H), 6.82 (dd, J=2.0, 2.6, 1H), 6.29 (s, 1H), 5.95 (s, 1H), 5.91 (dd, J=2.7, 3.4, 1H), 5.40–4.70 (br, 4H), 2.67 (t, J=5.5, 2H), 2.33 (t, J=6.7, 2H), 1.98 (p, J=6.4, 2H).

Anal. Calcd. for $C_{25}H_{22}N_2O_2+0.05C_4H_{10}O$: C, 77.76; H, 5.74; N, 7.25. Found: C, 77.75; H, 5.80; N, 7.11.

MS [(+)-APCI, m/z]: 383.1 [M+H]$^+$. Calcd. for $C_{25}H_{23}N_2O_2$: 383.1760.

EXAMPLE 25

(10,11-Dihydro-5H-pyrrolo[2,1-c][1,4]benzodiazepin-10-yl)-[4-(3-hydroxy-cyclohex-1-en-1-yl)-phenyl]-methanone 3-[4-(10,11-Dihydro-5H-pyrrolo[2,1-c][1,4]benzodiazepine-10-carbonyl)-phenyl]-cyclohex-2-enone of Example 24 (0.100 g, 0.261 mmol) and cerium (III) chloride (0.064 g, 0.261 mmol) were dissolved in methanol (1.3 mL) followed by addition of solid sodium borohydride (0.010 g, 0.261 mmol). After hydrogen evolution ceased (approximately 5 minutes), 0.1 N hydrochloric acid (50 mL) was added and the resulting mixture extracted with ethyl acetate. The extract was dried over anhydrous magnesium sulfate, filtered and concentrated. A slightly yellow solid was isolated which was dissolved in boiling diethyl ether and filtered. The product was precipitated from the filtrate by addition of pentane and the precipitate filtered and dried to afford the title compound (0.100 g) as an amorphous white solid.

$^1$H NMR (DMSO-$d_6$+$D_2$O, 400 MHz): δ 7.44 (dd, J=1.1, 7.5, 1H), 7.26–7.14 (m, 5H), 7.07 (t, J=7.5, 1H), 6.88 (d, J=7.3, 1H), 6.79 (t, J=2.2, 1H), 6.03 (m, 1H), 5.93 (s, 1H), 5.90 (t, J=2.6, 1H), 5.35–4.70 (br, 4H), 4.12 (m, 1H), 2.28–2.12 (m, 2H), 1.78–1.72 (m, 2H), 1.55–1.48 (m, 1H), 1.41–1.35 (m, 1H).

Anal. Calcd. for $C_{25}H_{24}N_2O_2+0.20H_2O$: C, 77.37; H, 6.34; N, 7.22. Found: C, 77.26; H, 6.34; N, 6.88.

MS [(+)-APCI, m/z]: 385.1 [M+H]$^+$. Calcd. for $C_{25}H_{25}N_2O_2$: 385.1917.

EXAMPLE 26

3-[4-(10,11-Dihydro-5H-pyrrolo[2,1-c][1,4]benzodiazepine-10-carbonyl)-phenyl]-2-methyl-cyclohex-2-en-1-one (10,11-Dihydro-5H-pyrrolo[2,1-c][1,4]benzodiazepin-10-yl)-[4-(4,4,5,5-tetramethyl-[1,3,2]dioxaborolan-2-yl)-phenyl]-methanone of Example 19, Step B (0.350 g, 0.87 mmol) and 3-oxo-2-methyl-cylclohex-1-en-1-yl trifluoromethanesulfonate (0.248 g, 0.96 mmol) were reacted in the manner of Example 1, Step F. Purification by flash column chromatography on silica gel, eluting with a solvent gradient of from 20 to 50% ethyl acetate in hexane afforded a light yellow oil. The oil thus isolated was dissolved in boiling diethyl ether and precipitated by addition of petroleum ether. The precipitate was filtered and dried to afford the title compound (0.297 g) as a white solid, m.p. 95–97° C.

$^1$H NMR (DMSO-$d_6$, 400 MHz): δ 7.45 (d, J 7.5, 1H), 7.30 (d, J=8.1, 2H), 7.19–7.12 (m, 3H), 7.07 (t, J=7.4, 1H), 6.91 (d, J=6.8, 1H), 6.82 (t, J=2.0, 1H), 5.95 (s, 1H), 5.91 (t, J=3.4, 1H), 5.40–4.80 (br, 4H), 2.52–2.49 (m, 2H), 2.38 (t, J=6.8, 2H), 1.95 (p, J=6.6, 2H), 1.47 (s, 3H).

Anal. Calcd. for $C_{26}H_{24}N_2O_2+0.30H_2O$: C, 77.70; H, 6.17; N, 6.97. Found: C, 77.67; H, 6.45; N, 6.76.

MS [(+)-ESI, m/z]: 397.0 [M+H]$^+$. Calcd. for $C_{26}H_{25}N_2O_2$: 397.1918.

EXAMPLE 27

(10,11-Dihydro-5H-pyrrolo[2,1-c][1,4]benzodiazepin-10-yl)-[4-(3-hydroxy-2-methyl-cyclohex-1-en-1-yl)-phenyl]-methanone 3-[4-(10,11-Dihydro-5H-pyrrolo[2,1-c][1,4]benzodiazepine-10-carbonyl)-phenyl]-2-methyl-cyclohex-2-enone of Example 26 (0.330 g, 0.83 mmol) was reacted in the manner of Example 25 to provide the title compound (0.320 g) as a white solid.

$^1$H NMR (DMSO-$d_6$, 400 MHz): δ 7.45 (dd, J=1.3, 7.5, 1H), 7.20 (d, J=8.4, 2H), 7.16 (dt, J=1.1, 7.5, 1H), 7.07 (t, J=7.0, 1H), 6.96 (d, J=8.1, 2H), 6.89 (d, J=7.7, 1H), 6.81 (dd, J=2.0, 2.6, 1H), 5.94 (s, 1H), 5.91 (dd, J=2.6, 3.5, 1H), 5.40–4.80 (br, 4H), 4.67 (br, 1H), 3.86 (s, 1H), 2.10–1.98 (m, 2H), 1.74–1.58 (m, 3H), 1.55–1.49 (m, 1H), 1.46 (s, 3H).

Anal. Calcd. for $C_{26}H_{26}N_2O_2+0.10C_4H_{10}O$: C, 76.93; H, 6.46; N, 6.90. Found: C, 76.57; H, 6.79; N, 6.66.

MS [(+)-ESI, m/z]: 399.1 [M+H]$^+$. Calcd. for $C_{26}H_{27}N_2O_2$: 399.2078.

EXAMPLE 28

(10,11-Dihydro-5H-pyrrolo[2,1-c][1,4]benzodiazepin-10-yl)-(4-cyclohex-1-en-1-yl-3-methyl-phenyl)-methanone Step A. 3-Methyl-4-(4,4,5,5-tetramethyl-[1,3,2]dioxaborolan-2-yl)-benzoic acid methyl ester 4-Bromo-3-methyl benzoic acid methyl ester (5.00 g, 21.8 mmol) and bis(pinacolato)diboron (6.09 g, 24.0 mmol) were reacted in the manner of Example 7, Step A. Recrystallization from pentane (−20° C.) afforded the title compound (5.59 g), m.p. 53–54° C.

$^1$H NMR (CDCl$_3$, 400 MHz): δ 7.83–7.81 (m, 1H), 7.80–7.79 (m, 2H), 3.91 (s, 3H), 2.57 (s, 3H), 1.36 (s, 12H).

Anal. Calcd. for $C_{15}H_{21}BO_4$: C, 65.24; H, 7.67. Found: C, 65.67; H, 7.54.

MS [(+)-ESI, m/z]: 294.0 [M+NH$_4$]$^+$. Calcd, for $C_{15}H_{25}BNO_4$: 294.191.

Step B. 4-Cyclohex-1-en-1-yl-3-methyl-benzoic acid methyl ester

3-Methyl-4-(4,4,5,5-tetramethyl-[1,3,2]dioxaborolan-2-yl)-benzoic acid methyl ester of Step A (5.00 g, 18.1 mmol) and cyclohex-1-en-1-yl trifluoromethanesulfonate (4.58 g, 19.9 mmol) were reacted in the manner of Example 1, Step F. Purification by flash column chromatography on silica gel, eluting with 10% ethyl acetate in hexane, afforded the title compound (3.97 g) as a clear oil.

Step C. 4-Cyclohex-1-en-1-yl-3-methyl-benzoic acid

4-Cyclohex-1-en-1-yl-3-methyl-benzoic acid methyl ester of Step B (0.834 g, 3.62 mmol) was saponified in the manner of Example 15, Step C. Recrystallization from petroleum ether afforded the title compound (0.550 g) as white crystals, m.p. 173–175° C.

$^1$H NMR (DMSO-$d_6$, 400 MHz): δ 12.72 (br, 1H), 7.74 (s, 1H), 7.68 (dd, J=1.8, 7.9, 1H), 7.13 (d, J=7.9, 1H), 5.54 (m, 1H), 2.27 (s, 3H), 2.14–2.11 (m, 4H), 1.72–1.61 (m, 4H).

Anal. Calcd. for $C_{14}H_{16}O_2$+0.10$H_2O$: C, 77.11; H, 7.49. Found: C, 77.06; H, 7.44.

MS [EI, m/z]: 216 [M]$^+$. Calcd. for $C_{14}H_{16}O_2$: 216.115.

Step D. (10,11-Dihydro-5H-pyrrolo[2,1-c][1,4]benzodiazepin-10-yl)-(4-cyclohex-1-en-1-yl-3-methyl-phenyl)-methanone 4-Cyclohex-1-en-1-yl-3-methyl-benzoic acid of Step C (0.360 g, 1.66 mmol) and 10,11-dihydro-5H-pyrrolo[2,1-c][1,4]benzodiazepine (0.337 g, 1.83 mmol) were reacted in the manner of Example 15, Step D. Purification by flash column chromatography on silica gel, eluting with 20% ethyl acetate in hexane, followed by recrystallization from 1:1 ethyl acetate/petroleum ether afforded the title compound (0.510 g) as white crystals, m.p. 182–183° C.

$^1$H NMR (DMSO-$d_6$, 400 MHz): δ 7.47 (dd, J=1.5, 7.5, 1H), 7.21–7.10 (m, 3H), 6.93 (d, J=8.3, 2H), 6.83 (d, J=7.7, 1H), 6.81 (t, J=2.3, 1H), 5.93–5.91 (m, 2H), 5.43 (m, 1H), 5.26 (bs, 2H), 5.20–4.80 (br, 2H), 2.11 (s, 3H), 2.09–2.05 (m, 4H), 1.67–1.56 (m, 4H).

Anal. Calcd. for $C_{26}H_{26}N_2O$+0.15$H_2O$: C, 81.07; H, 6.88; N, 7.27. Found: C, 81.03; H, 6.86; N, 7.24.

MS [(+)-ESI, m/z]: 383 [M+H]$^+$. Calcd. for $C_{26}H_{27}N_2O$: 383.2128.

EXAMPLE 29

(10,11-Dihydro-5H-pyrrolo[2,1-c][1,4]benzodiazepin-10-yl)-[3-methyl-4-(6-methyl-cyclohex-1-en-1-yl)-phenyl]-methanone (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2, Step B (0.428 g, 1.00 mmol) and 6-methyl-cyclohex-1-en-1-yl trifluoromethanesulfonate (0.269 g, 1.10 mmol) were reacted in the manner of Example 2, Step C. Purification by flash column chromatography on silica gel, eluting with 20% ethyl acetate in hexane, followed by recrystallization from petroleum ether afforded the title compound (0.350 g) as white crystals, m.p. 132–133° C.

$^1$H NMR (DMSO-$d_6$, 400 MHz): δ 7.45 (dd, J=1.3, 7.5, 1H), 7.19–7.14 (m, 2H), 7.08 (t, J=7.5, 1H), 6.91 (t, J=7.9, 2H), 6.81–6.78 (m, 2H), 5.93 (m, 1H), 5.91 (t, J=3.1, 1H), 5.36 (m, 1H), 5.35–4.80 (br, 4H), 2.40–2.37 (m, 1H), 2.09 (s, 3H), 2.07–2.03 (m, 2H), 1.82–1.77 (m, 1H), 1.68–1.62 (m, 1H), 1.55–1.51 (m, 1H), 1.40–1.35 (m, 1H), 0.63 (d, J=7.0, 3H).

Anal. Calcd. for $C_{27}H_{28}N_2O$+0.05$C_4H_8O_2$: C, 81.48; H, 7.14; N, 6.99. Found: C, 81.26; H, 7.16; N, 6.86.

MS [(+)-APCI, m/z]: 397.0 [M+H]$^+$. Calcd. for $C_{27}H_{29}N_2O$: 397.2281.

EXAMPLE 30

(10,11-Dihydro-5H-pyrrolo[2,1-c][1,4]benzodiazepin-10-yl)-[4-(6,6-dimethyl-cyclohex-1-en-1-yl)-3-methyl-phenyl]-methanone Step A. 4-(6,6-Dimethyl-cyclohex-1-en-1-yl)-3-methyl-benzoic acid methyl ester 3-Methyl-4-(4,4,5,5-tetramethyl-[1,3,2]dioxaborolan-2-yl)-benzoic acid methyl ester of Example 28, Step A (0.300 g, 1.09 mmol) and 6,6-dimethyl-cyclohex-1-en-1-yl trifluoromethanesulfonate (0.338 g, 1.31 mmol) were reacted in the manner of Example 1, Step F. Purification by flash column chromatography on silica gel, eluting with 5% ethyl acetate in hexane, afforded the title compound (0.157 g) as a clear oil.

Step B. 4-(6,6-dimethyl-cyclohex-1-en-1-yl)-3-methyl-benzoic acid 4-(6,6-Dimethyl-cyclohex-1-en-1-yl)-3-methyl-benzoic acid methyl ester of Step A (0.157 g, 0.608 mmol) was saponified in the manner of Example 15, Step C. Recrystallization from petroleum ether afforded the title compound (0.130 g) as white crystals.

$^1$H NMR (CDCl$_3$, 300 MHz): δ 11.60 (br, 1H), 7.94–7.80 (m, 2H), 7.17–7.12 (m, 1H), 5.33 (m, 1H), 2.30 (s, 3H), 2.18–2.05 (m, 2H), 1.80–1.59 (m, 4H), 0.94 (br, 6H).

Step C. (10,11-Dihydro-5H-pyrrolo[2,1-c][1,4]benzodiazepin-10-yl)-[4-(6,6-dimethyl-cyclohex-1-en-1-yl)-3-methyl-phenyl]-methanone 4-(6,6-Dimethyl-cyclohex-1-en-1-yl)-3-methyl-benzoic acid of Step B (0.078 g, 0.319 mmol) and 10,11-dihydro-5H-pyrrolo[2,1-c][1,4]benzodiazepine (0.065 g, 0.351 mmol) were reacted in the manner of Example 15, Step D. Purification by flash column chromatography on silica gel, eluting with 20% ethyl acetate in hexane, followed by recrystallization from petroleum ether afforded the title compound (0.0670 g) as white crystals, m.p. 131° C.

$^1$H NMR (DMSO-$d_6$, 400 MHz): δ 7.45 (dd, J=1.5, 7.5, 1H), 7.17–7.14 (m, 2H), 7.06 (t, J=7.4, 1H), 6.90–6.87 (m, 2H), 6.81 (t, J=2.4, 1H), 6.77 (d, J=7.9, 1H), 5.94 (s, 1H), 5.91 (t, J=3.1, 1H), 5.27 (br, 2H), 5.18 (t, J=3.7, 1H), 2.07 (s, 3H), 2.06–2.01 (m, 2H), 1.67–1.63 (m, 2H), 1.53–1.50 (m, 2H), 0.80 (br, 6H).

Anal. Calcd. for $C_{28}H_{30}N_2O$: C, 81.91; H, 7.37; N, 6.82. Found: C, 81.48; H, 7.32; N, 6.71.

MS [(+)-ESI, m/z]: 411.3 [M+H]$^+$. Calcd. for $C_{28}H_{31}N_2O$: 411.2438.

EXAMPLE 31

(10,11-Dihydro-5H-pyrrolo[2,1-c][1,4]benzodiazepin-10-yl)-[4-(3,4-dihydro-naphthalen-1-yl)-3-methyl-phenyl]-methanone Step A. 4-(3,4-Dihydro-naphthalen-1-yl)-3-methyl-benzoic acid methyl ester 3-Methyl-4-(4,4,5,5-tetramethyl-[1,3,2]dioxaborolan-2-yl)-benzoic acid methyl ester of Example 28, Step A (5.00 g, 18.1 mmol) and 3,4-dihydronaphthalen-1-yl trifluoromethanesulfonate (5.54 g, 19.9 mmol) were reacted in the manner of Example 1, Step F. Purification by flash column chromatography on silica gel, eluting with 10% ethyl acetate in hexane, afforded the title compound (4.90 g) as a light yellow oil.

Step B. 4-(3,4-Dihydro-naphthalen-1-yl)-3-methyl-benzoic acid 4-(3,4-Dihydro-naphthalen-1-yl)-3-methyl-benzoic acid methyl ester of Step A (2.50 g, 8.98 mmol) was saponified in the manner of Example 15, Step C to provide the title compound (2.33 g) as a light yellow solid, m.p. 173° C.

$^1$H NMR (DMSO-$d_6$, 400 MHz): δ 12.82 (br, 1H), 7.82–7.79 (m, 2H), 7.25–7.21 (m, 2H), 7.14 (dt, J=1.3, 7.5, 1H), 7.05 (dt, J=1.3, 7.5, 1H), 6.42 (d, J=6.8, 1H), 5.96 (t, J=4.5,1H), 2.83 (t, J=8.0, 2H), 2.41–2.35 (m, 2H), 2.07 (s, 3H).

Anal. Calcd. for $C_{18}H_{16}O_2$: C, 80.69; H, 6.17. Found: C, 80.66; H, 6.28.

MS [(−)-APCI, m/z]: 263.2 [M−H]$^-$. Calcd. for $C_{18}H_{15}O_2$: 263.1072.

Step C. (10,11-Dihydro-5H-pyrrolo[2,1-c][1,4]benzodiazepin-10-yl)-[4-(3,4-dihydro-naphthalen-1-yl)-3-methyl-phenyl]-methanone 4-(3,4-Dihydro-naphthalen-1-yl)-3-methyl-benzoic acid of Step B (0.220 g, 0.832 mmol) and 10,11-dihydro-5H-pyrrolo[2,1-c][1,4]benzodiazepine (0.169 g, 0.915 mmol) were reacted in the manner of Example 15, Step D. Purification by flash column chromatography on silica gel, eluting with 15% ethyl acetate in hexane, followed by recrystallization from petroleum ether afforded the title compound (0.307 g) as white crystals, m.p. 108° C.

$^1$H NMR (DMSO-$d_6$, 400 MHz): δ 7.46 (d, J=6.2, 1H), 7.22–6.91 (m, 9H), 6.93 (s, 1H), 6.22 (d, J=7.7, 1H), 5.95 (s, 1H), 5.92 (t, J=2.6, 1H), 5.84 (t, J=4.5, 1H), 5.30 (bs, 4H), 2.77 (t, J=7.7, 2H), 2.35–2.32 (m, 2H), 1.88 (s, 3H).

Anal. Calcd. for $C_{30}H_{26}N_2O+0.16C_6H_{14}+0.30H_2O$: C, 82.68; H, 6.46; N, 6.23. Found: C, 82.47; H, 6.63; N, 6.05.

MS [(+)-APCI, m/z]: 431 [M+H]$^+$. Calcd. for $C_{30}H_{27}N_2O$ 431.2128.

EXAMPLE 32

(10,11-Dihydro-5H-pyrrolo[2,1-c][1,4]benzodiazepin-10-yl)-[4-(3,4-dihydro-naphthalen-1-yl)-3-methyl-phenyl]-methanone (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2, Step B (0.760 g, 1.89 mmol), 3,4-dihydro-naphthalen-1-yl trifluoromethanesulfonate (0.579 g, 2.08 mmol) and dichloro[1,1'-bis(diphenylphosphino)ferrocene]palladium(II) dichloromethane adduct (0.046 g, 0.0567 mmol) were combined in N,N-dimethylformamide (9.5 mL). 2 M aqueous sodium carbonate (4.73 mL, 9.45 mmol) was added and the reaction heated to 60° C. for 3 hours. After cooling to room temperature, the reaction mixture was diluted with ethyl acetate (100 mL) and washed with water and brine. The organic phase was dried over anhydrous magnesium sulfate, filtered and concentrated and the residue purified by flash column chromatography (silica, 30% ethyl acetate in hexanes). Recrystallization from petroleum ether afforded the title compound (0.740 g) as white crystals identical to the material of Example 31.

EXAMPLE 33

(10,11-Dihydro-5H-pyrrolo[2,1-c][1,4]benzodiazepin-10-yl)-[4-(2,6-dimethyl-cyclohex-1-en-1-yl)-3-methyl-phenyl]-methanone (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2, Step B (0.500 g, 1.17 mmol) and 2,6-dimethyl-cyclohex-1-en-1-yl trifluoromethanesulfonate (0.401 g, 1.29 mmol) were reacted in the manner of Example 2, Step C. Purification by flash column chromatography on silica gel, eluting with 30% ethyl acetate in hexane, followed by recrystallization from petroleum ether (−20° C.) afforded the title compound as white crystals, m.p. 133–135° C.

$^1$H NMR (DMSO-$d_6$, 400 MHz): δ 7.44 (d, J=7.5, 2H), 7.17–7.13 (m, 3H), 7.09 (s, 1H), 7.03 (q, J=7.5, 2H), 6.97 (d, J=7.5, 1H), 6.91–6.85 (m, 3H), 6.81 (t, J=2.2, 2H), 6.78 (d, J=7.7, 1H), 6.63 (d, J=7.9, 1H), 5.94 (s, 2H), 5.91 (t, J=2.5, 2H), 5.35–4.80 (br, 8H), 2.30–2.27 (m, 1H), 2.13–2.09 (m, 1H), 2.03–1.89 (m, 10H), 1.78–1.54 (m, 6H), 1.42–1.36 (m, 2H), 1.19 (s, 3H), 1.15 (s, 3H), 0.69 (s, 3H), 0.60 (s, 3H) [the compound is a 1:1 mixture of diastereomers on the NMR time-scale].

Anal. Calcd. for $C_{28}H_{30}N_2O+0.10C_4H_{10}O$: C, 80.46; H, 7.24; N, 6.70. Found: C, 80.26; H, 7.24; N, 6.70.

MS [(+)-APCI, m/z]: 411.2 [M+H]$^+$. Calcd. for $C_{28}H_{31}N_2O$: 411.2438.

EXAMPLE 34

(10,11-Dihydro-5H-pyrrolo[2,1-c][1,4]benzodiazepin-10-yl)-[4-(6-tert-butyl-cyclohex-1-en-1-yl)-3-methyl-phenyl]-methanone Step A. 4-(6-tert-Butyl-cyclohex-1-en-1-yl)-3-methyl-benzoic acid methyl ester 3-Methyl-4-(4,4,5,5-tetramethyl-[1,3,2]dioxaborolan-2-yl)-benzoic acid methyl ester of Example 28, Step A (1.00 g, 3.62 mmol) and 6-tert-butyl-cyclohex-1-en-1-yl trifluoromethanesulfonate (1.24 g, 4.34 mmol) were reacted in the manner of Example 1, Step F. Purification by flash column chromatography on silica gel, eluting with a solvent gradient of from 0 to 5% ethyl acetate in hexane, afforded the title compound (0.880 g) as a light yellow oil.

Step B. 4-(6-tert-Butyl-cyclohex-1-en-1-yl)-3-methyl-benzoic acid 4-(6-tert-Butyl-cyclohex-1-en-1-yl)-3-methyl-benzoic acid methyl ester of Step A (0.880 g, 3.07 mmol) was saponified in the manner of Example 15, Step C to provide the title compound (0.580 g) as a white solid, m.p. 152° C.

$^1$H NMR (DMSO-$d_6$, 400 MHz): δ 12.72 (br, 1H), 7.70 (s, 1H), 7.67 (dd, J=1.7, 8.0, 1H), 7.19 (d, J=7.9, 1H), 5.69 (t, J=3.9, 1H), 2.53 (m, 1H), 2.33 (s, 3H), 2.11 (m, 2H), 1.79–1.73 (m, 3H), 1.54–1.48 (m, 1H), 0.71 (s, 9H).

Anal. Calcd. for $C_{18}H_{24}O_2+0.20H_2O$: C, 78.34; H, 8.91. Found: C, 78.13; H, 8.63.

MS [EI, m/z]: 272 [M]$^+$. Calcd. for $C_{18}H_{24}O_2$: 272.178.

Step C. (10,11-Dihydro-5H-pyrrolo[2,1-c][1,4]benzodiazepin-10-yl)-[4-(6-tert-butyl-cyclohex-1-en-1-yl)-3-methyl-phenyl]-methanone 4-(6-tert-Butyl-cyclohex-1-en-1-yl)-3-methyl-benzoic acid of Step B (0.104 g, 0.382 mmol) and 10,11-dihydro-5H-pyrrolo[2,1-c][1,4]benzodiazepine (0.077 g, 0.420 mmol) were reacted in the manner of Example 15, Step D: Purification by flash column chromatography on silica gel, eluting with 20% ethyl acetate in hexane, followed by recrystallization from pentane afforded the title compound (0.160 g) as white crystals, m.p. 127–129° C.

$^1$H NMR (DMSO-$d_6$, 400 MHz): δ 7.43 (dd, J=1.1, 7.5, 1H), 7.13 (t, J=7.3, 1H), 7.07 (s, 1H), 6.98 (t, J=7.5, 1H), 6.93–6.80 (m, 4H), 5.93 (s, 1H), 5.91 (t, J=3.1, 1H), 5.57 (t,

J=3.5, 1H), 5.34–4.70 (br, 4H), 2.38 (m, 1H), 2.14 (s, 3H), 2.06–2.04 (m, 2H), 1.74–1.66 (m, 3H), 1.49–1.43 (m, 1H), 0.60 (s, 9H).

Anal. Calcd. for $C_{30}H_{34}N_2O+0.15H_2O$: C, 81.65; H, 7.83; N, 6.35. Found: C, 81.61; H, 7.83; N, 6.32.

MS [(+)-ESI, m/z]: 439.2 [M+H]$^+$. Calcd. for $C_{30}H_{35}N_2O$: 439.2748.

EXAMPLE 35

(10,11-Dihydro-5H-pyrrolo[2,1-c][1,4]benzodiazepin-10-yl)-(4-bicyclo[3.2.1]oct-2-en-2-yl-3-methyl-phenyl)-methanone Step A. 4-(Bicyclo[3.2.1]oct-2-en-2-yl)-3-methyl-benzoic acid methyl ester 3-Methyl-4-(4,4,5,5-tetramethyl-[1,3,2]dioxaborolan-2-yl)-benzoic acid methyl ester of Example 28, Step A (0.300 g, 1.09 mmol) and bicyclo[3.2.1]oct-2-en-2-yl trifluoromethanesulfonate (0.336 g, 1.31 mmol) were reacted in the manner of Example 1, Step F. Purification by flash column chromatography on silica gel, eluting with 5% ethyl acetate in hexane, afforded the title compound (0.161 g) as a light yellow oil.

Step B. 4-(Bicyclo[3.2.1]oct-2-en-2-yl)-3-methyl-benzoic acid 4-(Bicyclo[3.2.1]oct-2-en-2-yl)-3-methyl-benzoic acid methyl ester of Step A (0.157 g, 0.608 mmol) was saponified in the manner of Example 15, Step C. Recrystallization from petroleum ether afforded the title compound (0.130 g) as a white solid.

$^1$H NMR (CDCl$_3$, 300 MHz): δ 11.78 (br, 1H), 7.92–7.84 (m, 2H), 7.20–7.14 (m, 1H), 5.30 (br, 1H), 2.60–2.28 (m, 6H), 2.03–1.50 (m, 7H).

Step C. (10,11-Dihydro-5H-pyrrolo[2,1-c][1,4]benzodiazepin-10-yl)-[4-(bicyclo[3.2.1]oct-2-en-2-yl)-3-methyl-phenyl]-methanone 4-(Bicyclo[3.2.1]oct-2-en-2-yl)-3-methyl-benzoic acid of Step B (0.132 g, 0.545 mmol) and 10,11-dihydro-5H-pyrrolo[2,1-c][1,4]benzodiazepine (0.111 g, 0.6 mmol) were reacted by in the manner of Example 15, Step D. Purification by flash column chromatography on silica gel, eluting with 20% ethyl acetate in hexane, followed by recrystallization from 1:1 ethyl acetate/petroleum ether afforded the title compound (0.152 g) as white crystals, m.p. 168–169° C.

$^1$H NMR (DMSO-d$_6$, 400 MHz): δ 7.47 (dd, J=1.5, 7.5, 1H), 7.21–7.11 (m, 3H), 6.95 (d, J=7.5, 2H), 6.83 (d, J=7.9, 1H), 6.80 (t, J=2.2, 1H), 5.94–5.91 (m, 2H), 5.27 (br, 2H), 5.14 (m, 1H), 2.45–2.32 (m, 3H), 2.12 (s, 3H), 1.92–1.44 (m, 7H) [2 of 4 benzodiazepine protons are too broad to be observed].

Anal. Calcd. for $C_{28}H_{28}N_2O+0.15H_2O$: C, 81.78; H, 6.94; N, 6.81. Found: C, 81.77; H, 6.82; N, 6.75.

MS [(+)-ESI, m/z]: 409.3 [M+H]$^+$, 817.4 [2M+H]$^+$. Calcd. for $C_{28}H_{29}N_2O$: 409.2278.

EXAMPLE 36

(10,11-Dihydro-5H-pyrrolo[2,1-c][1,4]benzodiazepin-10-yl)-[4-(6,6-dimethyl-bicyclo[3.1.1]hept-2-en-2-yl)-3-methyl-phenyl]-methanone Step A. 4-(6,6-Dimethyl-bicyclo[3.1.1]hept-2-en-2-yl)-3-methyl-benzoic acid methyl ester 3-Methyl-4-(4,4,5,5-tetramethyl-[1,3,2]dioxaborolan-2-yl)-benzoic acid methyl ester of Example 28, Step A (1.00 g, 3.62 mmol) and 6,6-dimethyl-bicyclo[3.1.1]hept-2-en-2-yl trifluoromethanesulfonate (1.17 g, 4.34 mmol) were reacted in the manner of Example 1, Step F. Purification by flash column chromatography on silica gel, eluting with a solvent gradient of from 0 to 5% ethyl acetate in hexane, afforded the title compound (0.680 g) as a light yellow oil.

Step B. 4-(6,6-Dimethyl-bicyclo[3.1.1]hept-2-en-2-yl)-3-methyl-benzoic acid 4-(6,6-Dimethyl-bicyclo[3.1.1]hept-2-en-2-yl)-3-methyl-benzoic acid methyl ester of Step A (0.680 g, 2.52 mmol) was saponified in the manner of Example 15, Step C. Recrystallization from petroleum ether afforded the title compound (0.440 g) as a white solid, m.p. 139–140° C.

$^1$H NMR (DMSO-d$_8$, 400 MHz): δ 12.76 (br, 1H), 7.72 (s, 1H), 7.70 (dd, J=1.5, 8.0, 1H), 7.09 (d, J=7.7, 1H), 5.58 (m, 1H), 2.58–2.46 (m, 2H), 2.42 (t, J=3.1, 1H), 2.37 (t, J=2.9, 1H), 2.31 (dt, J=1.5, 5.5, 1H), 2.26 (s, 3H), 2.17–2.14 (m, 1H), 1.30 (s, 3H), 0.96 (s, 3H).

Anal. Calcd. for $C_{17}H_{20}O_2+0.15H_2O$: C, 78.82; H, 7.90. Found: C, 78.69; H, 7.71.

MS [(−)-APCI, m/z]: 255.2 [M−H]$^−$. Calcd. for $C_{17}H_{19}O_2$: 255.1382.

Step C. (10,11-Dihydro-5H-pyrrolo[2,1-c][1,4]benzodiazepin-10-yl)-[4-(6,6-dimethyl-bicyclo[3.1.1]hept-2-en-2-yl)-3-methyl-phenyl]-methanone 4-(6,6-Dimethyl-bicyclo[3.1.1]hept-2-en-2-yl)-3-methyl-benzoic acid of Step B (0.360 g, 1.40 mmol) and 10,11-dihydro-5H-pyrrolo[2,1-c][1,4]benzodiazepine (0.284 g, 1.54 mmol) were reacted in the manner of Example 15, Step D. Purification by flash column chromatography on silica gel, eluting with 20% ethyl acetate in hexane, followed by recrystallization from ethyl acetate afforded the title compound (0.510 g) as white crystals, m.p. 187° C.

$^1$H NMR (DMSO-d$_6$, 400 MHz): δ 7.47 (dd, J=1.3, 7.5, 1H), 7.20 (t, J=7.5, 1H), 7.15–7.12 (m, 2H), 6.98–6.94 (m, 2H), 6.81–6.79 (m, 2H), 5.93–5.91 (m, 2H), 5.46 (s, 1H), 5.35–4.70 (br, 4H), 2.49–2.35 (m, 4H), 2.21 (t, J=5.5, 1H), 2.10 (s, 4H), 1.27 (s, 3H), 0.90 (s, 3H).

Anal. Calcd. for $C_{29}H_{30}N_2O+0.15H_2O$: C, 81.90; H, 7.18; N, 6.59. Found: C, 81.83; H, 7.22; N, 6.53.

MS [(+)-ESI, m/z]: 423.2 [M+H]$^+$. Calcd. for $C_{29}H_{31}N_2O$: 423.2438.

EXAMPLE 37

(10,11-Dihydro-5H-pyrrolo[2,1-c][1,4]benzodiazepin-10-yl)-[3-methyl-4-(3,3,5,5-tetramethyl-cyclohex-1-en-1-yl)-phenyl]-methanone Step A. 3-Methyl-4-(3,3,5,5-tetramethyl-cyclohex-1-en-1-yl)-benzoic acid methyl ester 3-Methyl-4-(4,4,5,5-tetramethyl-[1,3,2]dioxaborolan-2-yl)-benzoic acid methyl ester of Example 28, Step A (0.500 g, 1.81 mmol) and 3,3,5,5-tetramethyl-cyclohex-1-en-1-yl trifluoromethanesulfonate (0.621 g, 2.17 mmol) were reacted by the procedure described in Example 1, Step F. Purification by flash column chromatography on silica gel, eluting with a solvent gradient of from 0 to 5% ethyl acetate in hexane, afforded the title compound (0.390 g) as a light yellow oil.

Step B. 3-Methyl-4-(3,3,5,5-tetramethyl-cyclohex-1-en-1-yl)-benzoic acid

3-Methyl-4-(3,3,5,5-tetramethyl-cyclohex-1-en-1-yl)-benzoic acid methyl ester of Step A (0.390 g, 1.36 mmol) was saponified in the manner of Example 15, Step C.

Recrystallization from petroleum ether afforded the title compound (0.310 g) as a white solid, m.p. 118–120° C.

$^1$H NMR (DMSO-d$_6$, 400 MHz): δ 12.75 (br, 1H), 7.74 (s, 1H), 7.69 (dd, J=1.5, 7.9, 1H), 7.10 (d, J=7.9, 1H), 5.31 (s, 1H), 2.28 (s, 3H), 1.93 (d, J=1.1, 2H), 1.39 (s, 2H), 1.06 (s, 6H), 1.02 (s, 6H).

Anal. Calcd. for C$_{18}$H$_{24}$O$_2$+0.15H$_2$O: C, 78.59; H, 8.90. Found: C, 78.66; H, 8.96.

MS [(−)-ESI, m/z]: 271.1 [M−H]$^−$. Calcd. for C$_{18}$H$_{23}$O$_2$: 271.1702.

Step C. (10,11-Dihydro-5H-pyrrolo[2,1-c][1,4]benzodiazepin-10-yl)-[3-methyl-4-(3,3,5,5-tetramethyl-cyclohex-1-en-1-yl)-phenyl]-methanone 3-Methyl-4-(3,3,5,5-tetramethyl-cyclohex-1-en-1-yl)-benzoic acid of Step B (0.100 g, 0.349 mmol) and 10,11-dihydro-5H-pyrrolo[2,1-c][1,4]benzodiazepine (0.071 g, 0.384 mmol) were reacted in the manner of Example 15, Step D. Purification by flash column chromatography on silica gel, eluting with 20% ethyl acetate in hexane, followed by recrystallization from petroleum ether afforded the title compound (0.123 g) as white crystals, m.p. 158° C.

$^1$H NMR (DMSO-d$_6$, 400 MHz): δ 7.47 (dd, J=1.5, 7.5, 1H), 7.21–7.11 (m, 3H), 6.96–6.93 (m, 2H), 6.81–6.79 (m, 2H), 5.93–5.90 (m, 2H), 5.27 (br, 2H), 5.19 (s, 1H), 2.12 (s, 3H), 1.83 (s, 2H), 1.34 (s, 2H), 1.01 (s, 6H), 0.97 (s, 6H) [2 of 4 benzodiazepine protons are too broad to be observed].

Anal. Calcd. for C$_{30}$H$_{34}$N$_2$O+0.20H$_2$O: C, 81.48; H, 7.84; N, 6.33. Found: C, 81.60; H, 7.86; N, 6.22.

MS [(+)-APCI, m/z]: 429.3 [M+H]$^+$. Calcd. for C$_{30}$H$_{35}$N$_2$O: 429.2748.

EXAMPLE 38

(10,11-Dihydro-5H-pyrrolo[2,1-c][1,4]benzodiazepin-10-yl)-{4-[2-(3-methoxy-phenyl)-cyclohex-1-en-1-yl]-3-methyl-phenyl}-methanone Step A. 4-[2-(3-Methoxy-phenyl)-cyclohex-1-en-1-yl]-3-methyl-benzoic acid methyl ester 3-Methyl-4-(4,4,5,5-tetramethyl-[1,3,2]dioxaborolan-2-yl)-benzoic acid methyl ester of Example 28, Step A (0.300 g, 1.09 mmol) and 2-(3-methoxy-phenyl)-cyclohex-1-en-1-yl trifluoromethanesulfonate (0.441 g, 1.31 mmol) were reacted in the manner of Example 1, Step F. Purification by flash column chromatography on silica gel, eluting with a solvent gradient of from 0 to 5% ethyl acetate in hexane, afforded the title compound (0.196 g) as a light yellow oil.

Step B. 4-[2-(3-Methoxy-phenyl)-cyclohex-1-en-1-yl]-3-methyl-benzoic acid

4-[2-(3-Methoxy-phenyl)-cyclohex-1-en-1-yl]-3-methyl-benzoic acid methyl ester of Step A (0.196 g, 0.58 mmol) was saponified in the manner of Example 15, Step C. Recrystallization from petroleum ether afforded the title compound (0.066 g) as a white solid.

$^1$H NMR (CDCl$_3$, 300 MHz): δ 11.80 (br, 1H), 7.79–7.72 (m, 2H), 7.15–7.00 (m, 3H), 6.62–6.55 (m, 2H), 3.55 (s, 3H), 2.42–2.25 (m, 4H), 2.13 (s, 3H), 1.90–1.75 (m, 4H).

Step C. (10,11-Dihydro-5H-pyrrolo[2,1-c][1,4]benzodiazepin-10-yl)-{4-[2-(3-methoxy-phenyl)-cyclohex-1-en-1-yl]-3-methyl-phenyl}-methanone 4-[2-(3-Methoxy-phenyl)-cyclohex-1-en-1-yl]-3-methyl-benzoic acid of Step B (0.066 g, 0.205 mmol) and 10,11-dihydro-5H-pyrrolo[2,1-c][1,4]benzodiazepine (0.041 g, 0.223 mmol) were reacted in the manner of Example 15, Step D. Purification by flash column chromatography on silica gel, eluting with 20% ethyl acetate in hexane, followed by recrystallization from petroleum ether/diethyl ether afforded the title compound (0.063 g) as white crystals, m.p. 91–94° C.

$^1$H NMR (DMSO-d$_6$, 400 MHz): δ 7.42 (d, J=7.7, 1H), 7.16–7.12 (m, 1H), 7.05–6.92 (m, 2H), 6.81–6.72 (m, 4H), 6.64–6.56 (m, 2H), 6.45 (d, J=7.9, 1H), 6.38 (d, J=1.0, 1H), 5.89 (d, J=1.2, 2H), 5.30–4.60 (br, 4H), 3.51 (s, 3H), 2.31–2.08 (m, 4H), 1.91 (s, 3H), 1.77–1.51 (m, 4H).

Anal. Calcd. for C$_{33}$H$_{32}$N$_2$O$_2$: C, 81.12; H, 6.60; N, 5.73. Found: C, 80.79; H, 6.99; N, 5.34.

MS [(+)-ESI, m/z]: 489.3 [M+H]$^+$. Calcd. for C$_{33}$H$_{33}$N$_2$O$_2$: 489.2538.

EXAMPLE 39

3-[4-(10,11-Dihydro-5H-pyrrolo[2,1-c][1,4]benzodiazepine-10-carbonyl)-2-methyl-phenyl]-cyclohex-2-en-1-one (10,11-Dihydro-5H-pyrrolo[2,1-c][1,4]benzodiazepin-10-yl)-[3-methyl-4-(4,4,5,5-tetramethyl-[1,3,2]dioxaborolan-2-yl)-phenyl]-methanone of Example 2, Step B (0.500 g, 1.17 mmol) and 3-oxo-cylcohex-1-en-1-yl trifluoromethanesulfonate (0.315 g, 1.29 mmol) were reacted in the manner of Example 1, Step F. Purification by flash column chromatography on silica gel, eluting with 50% ethyl acetate in hexane, followed by recrystallization from a mixture of diethyl ether and petroleum ether afforded the title compound (0.310 g) as light yellow crystals, m.p. 176–177° C.

$^1$H NMR (DMSO-d$_6$, 400 MHz): δ 7.47 (dd, J=1.5, 7.5, 1H), 7.25 (s, 1H), 7.19 (dt, J=1.1, 7.5, 1H), 7.12 (t, J=7.5, 1H), 7.04–6.95 (m, 3H), 6.81 (t, J=2.3, 1H), 5.94 (s, 1H), 5.91 (dd, J=2.6, 3.5, 1H), 5.72 (s, 1H), 5.35–4.75 (br, 4H), 2.47 (t, J=6.0, 2H), 2.36 (t, J=6.7, 2H), 2.03–1.97 (m, 2H), 2.16 (s, 3H).

Anal. Calcd. for C$_{26}$H$_{24}$N$_2$O$_2$+0.05C$_4$H$_{10}$O: C, 78.03; H, 6.04; N, 7.00. Found: C, 77.82; H, 5.89; N, 6.94.

MS [(+)-APCI, m/z]: 397.1 [M+H]$^+$. Calcd. for C$_{26}$H$_{25}$N$_2$O$_2$: 397.1917.

EXAMPLE 40

(10,11-Dihydro-5H-pyrrolo[2,1-c][1,4]benzodiazepin-10-yl)-[4-(3-hydroxy-cyclohex-1-en-1-yl)-3-methyl-phenyl]-methanone 3-[4-(10,11-Dihydro-5H-pyrrolo[2,1-c][1,4]benzodiazepine-10-carbonyl)-2-methyl-phenyl]-cyclohex-2-enone of Example 39 (0.100 g, 0.252 mmol) was reacted in the manner of Example 25. The crude product was dissolved in boiling diethyl ether, filtered and the product precipitated from the filtrate by addition of pentane to provide the title compound (0.100 g) as a white solid.

$^1$H NMR (DMSO-d$_6$+D$_2$O, 400 MHz): δ 7.44 (dd, J=1.1, 7.5, 1H), 7.17 (t, J=7.5, 1H), 7.12–7.08 (m, 2H), 6.94–6.92 (m, 2H), 6.84 (d, J=7.7, 1H), 6.78 (t, J=2.3, 1H), 5.91–5.89 (m, 2H), 5.35 (m, 1H), 5.30–4.65 (br, 4H), 4.09 (m, 1H), 2.09 (s, 3H), 2.06–1.91 (m, 2H), 1.75–1.72 (m, 2H), 1.54–1.42 (m, 2H).

Anal. Calcd. for C$_{26}$H$_{26}$N$_2$O$_2$+0.20H$_2$O: C, 77.66; H, 6.62; N, 6.97. Found: C, 77.67; H, 6.59; N, 6.63.

MS [(+)-APCI, m/z]: 399.1 [M+H]$^+$. Calcd. for C$_{26}$H$_{27}$N$_2$O$_2$: 399.2074.

EXAMPLE 41

(10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone Racemic (10,11-dihydro-5H-pyrrolo[2,1-c][1,4]benzodiazepin-10-yl)-[4-(3-hydroxy-2-methyl-cyclohex-1-en-1-yl)-3-methyl-phenyl]-methanone of Example 5 was subjected to chiral HPLC (Chiralpak AD, 21.1×250 mm, 50% ethanol in hexane). The first peak which eluted displayed a positive optical rotation and was arbitrarily assigned the (R)-configuration. The title compound was isolated as a white solid, $[\alpha]_D$=+34.30 (c=1.0, chloroform).

$^1$H NMR (DMSO-$d_6$, 400 MHz): δ 7.45 (dd, J=1.3, 7.5, 1H), 7.18–7.14 (m, 2H), 7.07 (t, J=7.3, 1H), 6.95 (t, J=8.3, 1H), 6.88 (d, J=7.7, 1H), 6.81 (t, J=2.3, 1H), 6.73 (t, J=8.1, 1H), 5.93 (s, 1H), 5.91 (t, J=3.6, 1H), 5.27 (bs, 2H), 5.25–4.80 (br, 2H), 3.90–3.84 (m, 1H), 1.99 (d, J=13.2, 3H), 1.90 (bs, 2H), 1.75–1.59 (m, 3H), 1.54–1.49 (m, 1H), 1.24 (s, 3H) [OH proton not observed].

Anal. Calcd. for $C_{27}H_{28}N_2O_2$+0.50$H_2O$+0.10$C_4H_{10}O$: C, 75.60; H, 6.81; N, 6.53. Found: C, 75.52; H, 6.92; N, 6.54.

MS [(+)-APCI, m/z]: 413.2 $[M+H]^+$. Calcd. for $C_{27}H_{29}N_2O_2$: 413.2230.

EXAMPLE 42

(10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone (S)-(−)-CBS-oxazaborolidine (1.0 M in tetrahydrofuran, 1.06 mL, 1.06 mmol) was dissolved in anhydrous tetrahydrofuran (53.1 mL, distilled from sodium/benzophenone ketyl). To this solution was simultaneously added a solution of (10,11-dihydro-5H-pyrrolo[2,1-c][1,4]benzodiazepin-10-yl)-[4-(2-methyl-3-oxo-cyclohex-1-en-1-yl)-3-methyl-phenyl]-methanone of Example 4 (2.18 g, 5.31 mmol) in anhydrous tetrahydrofuran (20 mL) via syringe pump (1.6 mL/min.) and borane-tetrahydrofuran (1.0 M in tetrahydrofuran, 3.19 mL, 3.19 mmol) at a rate such that enone addition was complete upon addition of approximately 2/3 of borane-tetrahydrofuran. Upon completion of borane-tetrahydrofuran addition, the reaction mixture was diluted with water (250 mL) and extracted with ethyl acetate. The combined extracts were washed with 1 N sodium hydroxide, 1N hydrochloric acid, and brine, dried over anhydrous magnesium sulfate, filtered and concentrated. The residue was purified by flash column chromatography (silica, 50% ethyl acetate in hexane) to afford the title compound (2.02 g) as a white solid. Analytical HPLC (Chiralpak AD, 4.6×250 mm, 50% ethanol in hexane, 0.5 mL/min.) indicated an enantiomeric excess of 96.4%.

EXAMPLE 43

(10,11-Dihydro-5H-pyrrolo-[2,1-c][1,4]benzodiazepin-10-yl)-[4-((3S)-3-hydroxy-2-methyl-cyclohex-1-en-1-yl)-3-methyl-phenyl]-methanone Racemic (10,11-Dihydro-5H-pyrrolo[2,1-c][1,4]benzodiazepin-10-yl)-[4-(3-hydroxy-2-methyl-cyclohex-1-en-1-yl)-3-methyl-phenyl]-methanone of Example 5 was subjected to chiral HPLC (Chiralpak AD, 21.1×250 mm, 50% ethanol in hexane). The second peak which eluted displayed a negative optical rotation and was arbitrarily assigned the (S)-configuration. The title compound was isolated as a white solid, $[\alpha]_D$=−36.69 (c=1.0, chloroform).

$^1$H NMR (DMSO-$d_6$, 400 MHz): δ 7.45 (d, J=7.5, 1H), 7.18 (d, J=7.3, 1H), 7.15 (s, 1H), 7.07 (t, J=7.5, 1H), 6.95 (t, J=8.3, 1H), 6.89 (d, J=7.7, 1H), 6.81 (s, 1H), 6.73 (t, J=7.9, 1H), 5.94 (s, 1H), 5.91 (t, J=3.0, 1H), 5.40–4.80 (br, 4H), 4.63 (br, 1H), 3.89–3.84 (m, 1H), 1.99 (d, J=13.2, 3H), 1.90 (br, 2H), 1.74–1.59 (m, 3H), 1.53–1.50 (m, 1H), 1.24 (s, 3H).

Anal. Calcd. for $C_{27}H_{28}N_2O_2$+0.50$H_2O$+0.10$C_4H_{10}O$: C, 75.60; H, 6.81; N, 6.53. Found: C, 75.57; H, 7.00; N, 6.27.

LRMS [(+)-APCI, m/z]: 413.2 $[M+H]^+$. Calcd. for $C_{27}H_{29}N_2O_2$: 413.2230.

EXAMPLE 44

10-{4-[(3R)-3-Methoxy-2-methylcyclohex-1-en-1-yl]-3-methylbenzoyl}-10,11-dihydro-5H-pyrrolo[2,1-c][1,4]benzodiazepine (10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone of Example 41 (0.125 g, 0.303 mmol) was dissolved in anhydrous tetrahydrofuran (3.0 mL) followed by addition of sodium hydride (0.008 g, 0.333 mmol). After hydrogen gas evolution ceased (5 minutes), methyl iodide (0.038 mL, 0.606 mmol) was added and the reaction stirred for 30 minutes. Additional sodium hydride (0.008 g, 0.333 mmol) was added and stirring continued overnight. The reaction was quenched with saturated ammonium chloride (50 mL) and extracted with ethyl acetate. The combined extracts were dried over anhydrous magnesium sulfate, filtered and concentrated. Purification of the residue by flash column chromatography, eluting with 30% ethyl acetate in hexane, followed by recrystallization from petroleum ether afforded the title compound (0.120 g) as white crystals, m.p. 127–128° C.; $[\alpha]_D$=+45.65 (c=1.0, chloroform). Single crystal X-ray crystallography established the absolute configuration as the (R)-isomer.

$^1$H NMR (DMSO-$d_6$, 400 MHz): δ 7.45 (dd, J=1.3, 7.5, 1H), 7.19–7.15 (m, 2H), 7.07 (t, J=7.5, 1H), 6.96 (t, J=6.6, 1H), 6.89 (d, J=7.7, 1H), 6.81 (t, J=2.2, 1H), 6.73 (dd, J=3.3, 7.7, 1H), 5.93 (m, 1H), 5.91 (dd, J=2.6, 3.5, 1H), 5.27 (br, 2H), 5.25–4.80 (br, 2H), 3.59–3.54 (m, 1H), 3.26 (s, 3H), 1.98 (s, 3H), 1.95–1.90 (m, 2H), 1.87–1.80 (m, 1H), 1.66–1.51 (m, 3H), 1.23 (s, 3H).

Anal. Calcd. for $C_{28}H_{30}N_2O_2$: C, 78.84; H, 7.09; N, 6.57. Found: C, 78.61; H, 7.18; N, 6.52.

MS [(+)-ESI, m/z]: 427.1 $[M+H]^+$. Calcd. for $C_{28}H_{31}N_2O_2$: 427.2387.

EXAMPLE 45

[4-(3-Amino-2-methyl-cyclohex-1-en-1-yl)-3-methyl-phenyl]-(10,11-dihydro-5H-pyrrolo[2,1-c][1,4]benzodiazepin-10-yl)-methanone Step A. [4-(3-Azido-2-methyl-cyclohex-1-en-1-yl)-3-methyl-phenyl]-(10,11-dihydro-5H-pyrrolo[2,1-c][1,4]benzodiazepin-10-yl)-methanone (10,11-Dihydro-5H-pyrrolo[2,1-c][1,4]benzodiazepin-10-yl)-[4-(3-hydroxy-2-methyl-cyclohex-1-en-1-yl)-3-methyl-phenyl]-methanone of Example 5 (0.310 g, 0.750 mmol) and 1,8-diazabicyclo[5.4.0]undec-7-ene (0.123 mL, 0.825 mmol) were dissolved in anhydrous dichloromethane (7.5 mL) followed by dropwise addition of diphenylphosphoryl azide (0.178 mL, 0.825 mmol). After stirring at room temperature for 24 hours, additional (0.224 mL, 1.50 mmol) and diphenylphosphoryl azide (0.356 mL, 1.65 mmol) was added and the reaction heated to reflux for one hour. The reaction mixture was cooled, diluted with ethyl acetate (75 mL) and washed with water, 1 N hydrochloric acid, saturated sodium bicarbonate and brine. The organic phase was dried over anhydrous magnesium sulfate, filtered and concentrated. The residue was purified by flash column chromatography on silica gel, eluting with 25% ethyl acetate in hexane to afford the title compound (0.310 g) as a clear oil.

$^1$H NMR (DMSO-$d_6$, 400 MHz): δ 7.48–7.42 (m, 1H), 7.20–7.15 (m, 2H), 7.07 (t, J=7.3, 1H), 6.99 (t, J=8.3, 1H), 6.89 (d, J=7.5, 1H), 6.81 (t, J=2.3, 1H), 6.77–6.74 (m, 1H), 5.94 (s, 1H), 5.91 (t, J=2.3, 1H), 5.35–4.85 (br, 4H), 3.97–3.87 (m, 1H), 2.04–1.97 (m, 5H), 1.90–1.83 (m, 2H), 1.70–1.62 (m, 2H), 1.32–1.28 (m, 3H).

MS [(+)-APCI, m/z]: 438.2 [M+H]$^+$. Calcd. for $C_{27}H_{28}N_5O$: 438.2278.

Step B. [4-(3-Amino-2-methyl-cyclohex-1-en-1-yl)-3-methyl-phenyl]-(10,11-dihydro-5H-pyrrolo[2,1-c][1,4]benzodiazepin-10-yl)-methanone

[4-(3-Azido-2-methyl-cyclohex-1-en-1-yl)-3-methyl-phenyl]-(10,11-dihydro-5H-pyrrolo[2,1-c][1,4]benzodiazepin-10-yl)-methanone of Step A (0.290 g, 0.663 mmol) was dissolved in 7 mL of a 10:1 mixture of tetrahydrofuran and water. Polymer-supported triphenylphosphine (0.287 g, approximately 0.862 mmol) was added and the reaction stirred at room temperature overnight. The mixture was filtered and concentrated, and the residue purified by flash column chromatography on silica gel, eluting with 3% ammonium hydroxide and 20% methanol in chloroform. A yellow oil was isolated which was triturated with 1:1 diethyl ether/petroleum ether to afford the title compound (0.100 g) as a white solid.

$^1$H NMR (DMSO-$d_6$+$D_2O$, 400 MHz): δ 7.42 (d, J=7.3, 1H), 7.17–6.84 (m, 5H), 6.79 (s, 1H), 6.75 (t, J=7.5, 1H), 5.92 (s, 1H), 5.90 (t, J=3.0, 1H), 5.30–4.80 (br, 4H), 3.51–3.43 (m, 1H), 2.06–1.90 (m, 6H), 1.87–1.55 (m, 3H), 1.23 (s, 3H).

MS [(+)-APCI, m/z]: 412.1 [M+H]$^+$. Calcd. for $C_{27}H_{30}N_3O$: 412.2390.

What is claimed:

1. A compound of the formula:

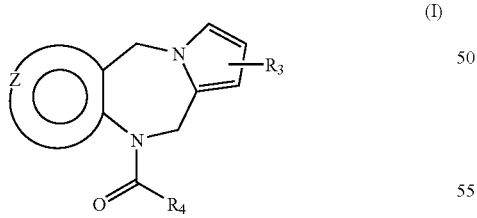
(I)

wherein:

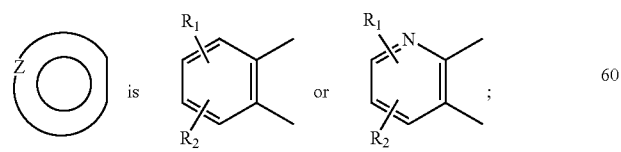

$R_1$ and $R_2$ are, independently, selected from hydrogen, ($C_1$–$C_6$)lower alkyl, halogen, cyano, trifluoromethyl, hydroxy, amino, ($C_1$–$C_6$) lower alkylamino, ($C_1$–$C_6$) lower alkoxy, —OCF$_3$, ($C_1$–$C_6$) lower alkoxycarbonyl, —NHCO[lower alkyl], carboxy, —CONH$_2$, —CONH($C_1$–$C_6$) lower alkyl, or —CON[($C_1$–$C_6$) lower alkyl]$_2$;

$R_3$ is a substituent selected from hydrogen, ($C_1$–$C_6$) lower alkyl, ($C_1$–$C_6$) lower alkoxy, hydroxy, amino, ($C_1$–$C_6$) lower alkylamino, —CO lower alkyl ($C_1$–$C_6$), or halogen; $R_4$ consists of the moiety B-C;

wherein B is selected from the group of

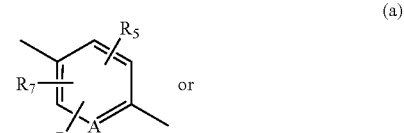
(a)

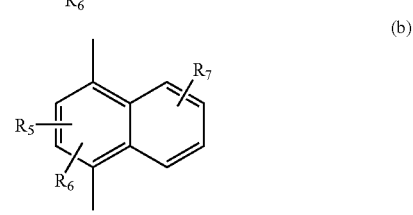
(b)

and C is defined as:

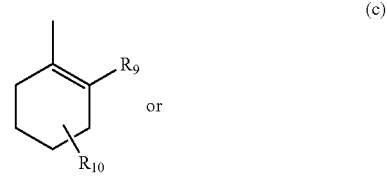
(c)

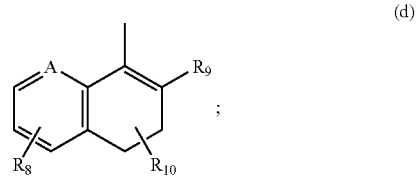
(d)

wherein:

A is CH or N;

$R_5$, $R_6$, $R_7$ and $R_8$ are independently, selected from hydrogen, ($C_1$–$C_6$) lower alkyl, ($C_1$–$C_6$) lower alkoxy, hydroxy ($C_1$–$C_6$) lower alkyl, alkoxy ($C_1$–$C_6$) lower alkyl, acyloxy ($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, aryl alkyloxycarbonyl, carbamoyl, —O—CH$_2$—CH=CH$_2$, halogen, halo lower alkyl, trifluoromethyl, —OCF$_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, lower alkylaminosulfonyl, naphthyl, phenyl, or

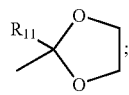

$R_9$ is chosen from the group of hydrogen, ($C_1$–$C_6$) lower alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, cyano; or aryl, optionally substituted by halogen, or lower alkoxy;

$R_{10}$ represents one to two substituents chosen independently, from the group of hydrogen, ($C_1$–$C_6$) lower alkyl, hydroxy ($C_1$–$C_6$) lower alkyl, alkoxy ($C_1$–$C_6$) lower alkyl, acyloxy ($C_1$–$C_6$) lower alkyl, [($C_1$–$C_6$) lower alkyl]$_2$, carbonyl,

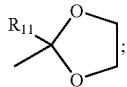

azido, amino, —NH[lower alkyl], —N[lower alkyl]$_2$, amino carbonyl lower alkyl, phthalimido, cyano, halogen, thio lower alkyl, aryloxy, arylthio, aryl optionally substituted with one to three substituents chosen from ($C_1$–$C_6$) lower alkyl, alkoxy or halogen; hydroxy, lower alkoxy, —OSO$_2$$R_{12}$, or OP' wherein P' is tert-butyl dimethylsilyl, tert-butyl diphenylsilyl, carbonyl loweralkyl, carbonyl trifluoro lower alkyl, aryl lower alkyl, arylcarbonyl, methoxymethyl, or methylthiomethyl; with the proviso that when $R_{10}$ represents two substituents, the two substituents may be joined together to form with the cyclohexene ring to which they are attached a bicyclic system selected from the group consisting of bicyclo[3.2.1]oct-2-ene and (6,6-dimethyl)-bicyclo[3.1.1]hept-2-ene;

$R_{11}$ is selected from the group of hydrogen, or ($C_1$–$C_6$) lower alkyl;

$R_{12}$ is selected from the group of ($C_1$–$C_6$) lower alkyl, trifluoro lower alkyl, or aryl optionally substituted by halogen or lower alkyl;

or a pharmaceutically acceptable salts form thereof.

2. A compound of claim 1 wherein:

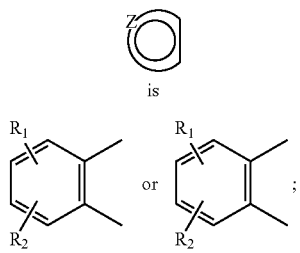

$R_1$ and $R_2$ are, independently, selected from hydrogen, $C_1$–$C_6$ alkyl, halogen, cyano, trifluoromethyl, hydroxy, amino, $C_1$–$C_6$ alkylamino, $C_1$–$C_6$ alkoxy, —OCF$_3$, ($C_1$–$C_6$) alkoxycarbonyl, —NHCO[$C_1$–$C_6$ alkyl], carboxy, —CONH$_2$, —CONH—($C_1$–$C_6$ alkyl), or —CON[$C_1$–$C_6$ alkyl]$_2$;

$R_3$ is a substituent selected from hydrogen, $C_1$–$C_6$ alkyl, $C_1$–$C_6$ alkoxy, hydroxy, amino, $C_1$–$C_6$ alkylamino, —CO-alkyl ($C_1$–$C_6$), or halogen;

$R_4$ consists of the moiety B-C;

wherein B is selected from the group of

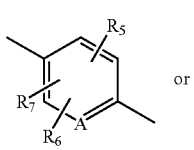

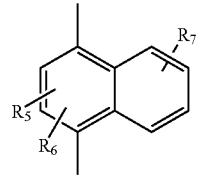

and C is defined as:

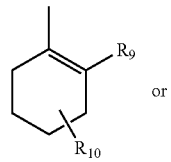

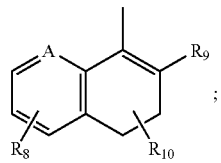

wherein:

A is CH;

$R_5$, $R_6$, $R_7$ and $R_8$ are independently selected from hydrogen, ($C_1$–$C_6$) lower alkyl, ($C_1$–$C_6$) lower alkoxy, hydroxy ($C_1$–$C_6$) lower alkyl, alkoxy ($C_1$–$C_6$) lower alkyl, acyloxy ($C_1$–$C_6$) lower alkyl, $C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, carbamoyl, —O—CH$_2$—CH=CH$_2$, halogen, halo lower alkyl, trifluoromethyl, —OCF$_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, or lower alkylaminosulfonyl;

$R_9$ is chosen from the group of hydrogen, $C_1$–$C_6$ alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, cyano; or phenyl optionally substituted by halogen, or $C_1$–$C_6$ alkoxy;

$R_{10}$ represents one to two substituents chosen independently, from the group of hydrogen, ($C_1$–$C_6$) lower alkyl, hydroxy ($C_1$–$C_6$) lower alkyl, alkoxy ($C_1$–$C_6$) lower alkyl, acyloxy ($C_1$–$C_6$) lower alkyl, [($C_1$–$C_6$) lower alkyl]$_2$, carbonyl, azido, amino, —NH[lower alkyl], —N[lower alkyl]$_2$, amino carbonyl lower alkyl, phthalimido, cyano, halogen, thio lower alkyl; hydroxy, lower alkoxy, —OSO$_2$$R_{12}$, or OP' wherein P' is tert-butyl dimethylsilyl, tert-butyl diphenylsilyl, carbonyl loweralkyl, carbonyl trifluoro $C_1$–$C_6$ alkyl, methoxymethyl, or methyithiomethyl; with the proviso that when $R_{10}$ represents two substituents, the two substituents may be joined together to form with the cyclohexene ring to which they are attached a bicyclic system selected from the group consisting of bicyclo[3.2.1]oct-2-ene and (6,6-dimethyl)-bicyclo[3.1.1]hept-2-ene;

$R_{12}$ is selected from the group of $C_1$–$C_6$ alkyl, or trifluoro $C_1$–$C_6$ alkyl;

or a pharmaceutically acceptable salt form thereof.

3. A compound of claim 1 selected from the group of:
   a) 10-(5-Chloro-4-cyclohex-1-en-1-yl-2-methoxybenzoyl)-10,11-dihydro-5H-pyrrolo[2,1-c][1,4]benzodiazepine;
   b) (10,11-Dihydro-5H-pyrrolo[2,1-c][1,4]benzodiazepin-10-yl)-(4-cyclohex-1-en-1-yl-3-methyl-phenyl)-methanone;
   c) (10,11-Dihydro-5H-pyrrolo[2,1-c][1,4]benzodiazepin-10-yl)-[4-(3,4-dihydro-naphthalen-1-yl)-3-methyl-phenyl]-methanone;
   d) (10,11-Dihydro-5H-pyrrolo[2,1-c][1,4]benzodiazepin-10-yl)-[4-(3-hydroxy-2-methyl-cyclohex-1-en-1-yl)-3-methyl-phenyl]-methanone;
   e) (10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone;
   f) (10,11-Dihydro-5H-pyrrolo[2,1-c][1,4]benzodiazepin-10-yl)-[4-(2-methyl-cyclohex-1-en-1-yl)-phenyl]-methanone;
   g) 10-[5-Chloro-4-(3,4-dihydro-naphthalen-1-yl)-2-methoxybenzoyl]-10,11-dihydro-5H-pyrrolo[2,1-c][1,4]benzodiazepine;
   h) (10,11-dihydro-5H-pyrrolo[2,1-c][1,4]benzodiazepin-10-yl)-[2-chloro-4-(cyclohex-1-en1-yl)-phenyl]-methanone;
or a pharmaceutically acceptable salt form thereof.

4. A compound of claim 1 selected from the group of:
   a) (10,11-Dihydro-5H-pyrrolo[2,1-c][1,4]benzodiazepin-10-yl)-[2-chloro-4-(3,4-dihydro-naphthalen-1-yl)-phenyl]-methanone;
   b) (10,11-Dihydro-5H-pyrrolo[2,1-c][1,4]benzodiazepin-10-yl)-[2-chloro-4-(6,6-dimethyl-cyclohex-1-en-1-yl)-phenyl]-methanone;
   c) (10,11-Dihydro-5H-pyrrolo[2,1-c][1,4]benzodiazepin-10-yl)-[2-chloro-4-(3-hydroxy-2-methyl-cyclohex-1-en-1-yl)-phenyl]-methanone;
   d) (10,11-Dihydro-5H-pyrrolo[2,1-c][1,4]benzodiazepin-10-yl)-(4-cyclohex-1-en-1-yl-phenyl)-methanone;
   e) (10,11-Dihydro-5H-pyrrolo[2,1-c][1,4]benzodiazepin-10-yl)-[4-(6-methyl-cyclohex-1-en-1-yl)-phenyl]-methanone;
   f) (10,11-Dihydro-5H-pyrrolo[2,1-c][1,4]benzodiazepin-10-yl)-[4-(6,6-dimethyl-cyclohex-1-en-1-yl)-phenyl]-methanone;
   g) (10,11-Dihydro-5H-pyrrolo[2,1-c][1,4]benzodiazepin-10-yl)-[4-(3,4-dihydro-naphthalen-1-yl)-phenyl]-methanone;
   h) (10,11-Dihydro-5H-pyrrolo[2,1-c][1,4]benzodiazepin-10-yl)-[4-(2,6-dimethyl-cyclohex-1-en-1-yl)-phenyl]-methanone; or
   i) (10,11-5H-Dihydro-pyrrolo[2,1-c][1,4]benzodiazepin-10-yl)-[4-(6-tert-butyl-cyclohex-1-en-1-yl)-phenyl]-methanone;
or a pharmaceutically acceptable salt form thereof.

5. A compound of claim 1 selected from the group of:
   a) (10,11-Dihydro-5H-pyrrolo[2,1-c][1,4]benzodiazepin-10-yl)-(4-bicyclo[3.2.1]oct-2-en-2-yl-phenyl)-methanone;
   b) (10,11-Dihydro-5H-pyrrolo[2,1-c][1,4]benzodiazepin-10-yl)-[4-(6,6-dimethyl-bicyclo[3.1.1]hept-2-en-2-yl)-phenyl]-methanone;
   c) (10,11-Dihydro-5H-pyrrolo[2,1-c][1,4]benzodiazepin-10-yl)-[4-(3,3,5,5-tetramethyl-cyclohex-1-en-1-yl)-phenyl]-methanone;
   d) (10,11-Dihydro-5H-pyrrolo[2,1-c][1,4]benzodiazepin-10-yl)-[4-(3-hydroxy-cyclohex-1-en-1-yl)-phenyl]-methanone;
   e) (10,11-Dihydro-5H-pyrrolo[2,1-c][1,4]benzodiazepin-10-yl)-[4-(3-hydroxy-2-methyl-cyclohex-1-en-1-yl)-phenyl]-methanone;
   f) (10,11-Dihydro-5H-pyrrolo[2,1-c][1,4]benzodiazepin-10-yl)-[3-methyl-4-(6-methyl-cyclohex-1-en-1-yl)-phenyl]-methanone;
   g) (10,11-Dihydro-5H-pyrrolo[2,1-c][1,4]benzodiazepin-10-yl)-[4-(6,6-dimethyl-cyclohex-1-en-1-yl)-3-methyl-phenyl]-methanone; or
   h) (10,11-Dihydro-5H-pyrrolo[2,1-c][1,4]benzodiazepin-10-yl)-[4-(3,4-dihydro-naphthalen-1-yl)-3-methyl-phenyl]-methanone;
or a pharmaceutically acceptable salt form thereof.

6. A compound of claim 1 selected from the group of:
   a) (10,11-Dihydro-5H-pyrrolo[2,1-c][1,4]benzodiazepin-10-yl)-[4-(2,6-dimethyl-cyclohex-1-en-1-yl)-3-methyl-phenyl]-methanone;
   b) (10,11-Dihydro-5H-pyrrolo[2,1-c][1,4]benzodiazepin-10-yl)-[4-(6-tert-butyl-cyclohex-1-en-1-yl)-3-methyl-phenyl]-methanone;
   c) (10,11-Dihydro-5H-pyrrolo[2,1-c][1,4]benzodiazepin-10-yl)-(4-bicyclo[3.2.1]oct-2-en-2-yl-3-methyl-phenyl)-methanone;
   d) (10,11-Dihydro-5H-pyrrolo[2,1-c][1,4]benzodiazepin-10-yl)-[4-(6,6-dimethyl-bicyclo[3.1.1]hept-2-en-2-yl)-3-methyl-phenyl]-methanone;
   e) (10,11-Dihydro-5H-pyrrolo[2,1-c][1,4]benzodiazepin-10-yl)-[3-methyl-4-(3,3,5,5-tetramethyl-cyclohex-1-en-1-yl)-phenyl]-methanone;
   f) (10,11-Dihydro-5H-pyrrolo[2,1-c][1,4]benzodiazepin-10-yl)-{4-[2-(3-methoxy-phenyl)-cyclohex-1-en-1-yl]-3-methyl-phenyl}-methanone;
   g) (10,11-Dihydro-5H-pyrrolo[2,1-c][1,4]benzodiazepin-10-yl)-[4-(3-hydroxy-cyclohex-1-en-1-yl)-3-methyl-phenyl]-methanone;
   h) (10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone;
   i) (10,11-Dihydro-5H-pyrrolo-[2,1-c][1,4]benzodiazepin-10-yl)-[4-((3S)-3-hydroxy-2-methyl-cyclohex-1-en-1-yl)-3-methyl-phenyl]-methanone;
   j) 10-{4-[(3R)-3-Methoxy-2-methylcyclohex-1-en-1-yl]-3-methylbenzoyl}-10,11-dihydro-5H-pyrrolo[2,1-c][1,4]benzodiazepine;
   k) [4-(3-Azido-2-methyl-cyclohex-1-en-1-yl)-3-methyl-phenyl]-(10,11-dihydro-5H-pyrrolo[2,1-c][1,4]benzodiazepin-10-yl)-methanone; or
   l) [4-(3-Amino-2-methyl-cyclohex-1-en-1-yl)-3-methyl-phenyl]-(10,11-dihydro-5H-pyrrolo[2,1-c][1,4]benzodiazepin-10-yl)-methanone;
or a pharmaceutically acceptable salt form thereof.

7. A pharmaceutical composition comprising a pharmaceutically effective amount of a compound of claim 1 and a pharmaceutically acceptable carrier or excipient.

8. A method for inhibiting preterm labor dysmenorrhea, endometritis, or for suppressing labor prior to caesarean delivery in a mammal, the method comprising administering to a mammal in need thereof a pharmaceutically effective amount of a compound of claim 1, or a pharmaceutically acceptable salt form thereof.

9. A method for treatment or inhibition of disorders in a mammal which are remedied or alleviated by vasopressin agonist activity selected from the group of diabetes insipidus, nocturnal enuresis, nocturia, urinary incontinence, or bleeding and coagulation disorders, the method comprising administering to a mammal in need thereof a pharmaceutically effective amount of a compound of claim 1, or a pharmaceutically acceptable salt form thereof.

10. A method for inducing temporary delay of urination in a mammal, the method comprising administering to a mammal in need thereof a pharmaceutically effective amount of a compound of claim 1, or a pharmaceutically acceptable salt form thereof.

11. A compound of the formula:

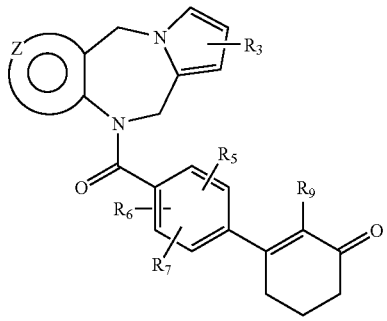

Wherein:

 is

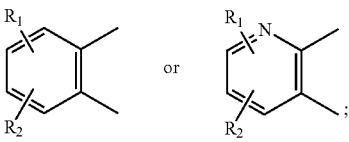 ;

$R_1$ and $R_2$ are, independently, selected from hydrogen, ($C_1$–$C_6$)lower alkyl, halogen, cyano, trifluoromethyl, hydroxy, amino, ($C_1$–$C_6$) lower alkylamino, ($C_1$–$C_6$) lower alkoxy, —$OCF_3$, ($C_1$–$C_6$) lower alkoxycarbonyl, —NHCO[lower alkyl], carboxy, —$CONH_2$, —CONH ($C_1$–$C_6$) lower alkyl, or —CON[($C_1$–$C_6$) lower alkyl]$_2$;

$R_3$ is a substituent selected from hydrogen, ($C_1$–$C_6$) lower alkyl, ($C_1$–$C_6$) lower alkoxy, hydroxy, amino, ($C_1$–$C_6$) lower alkylamino, —CO lower alkyl ($C_1$–$C_6$), or halogen;

$R_5$, $R_6$, and $R_7$ are independently, selected from hydrogen, ($C_1$–$C_6$) lower alkyl, ($C_1$–$C_6$) lower alkoxy, hydroxy ($C_1$–$C_6$) lower alkyl, alkoxy ($C_1$–$C_6$) lower alkyl, acyloxy ($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, aryl alkyloxycarbonyl, carbamoyl, —O—$CH_2$—CH=$CH_2$, halogen, halo lower alkyl, trifluoromethyl, —$OCF_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, lower alkylaminosulfonyl, naphthyl, phenyl, or

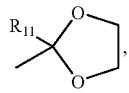

and $R_9$ is chosen from the group of hydrogen, ($C_1$–$C_6$) lower alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, cyano; or aryl, optionally substituted by halogen, or lower alkoxy; and $R_{11}$ is selected from the group of hydrogen, or ($C_1$–$C_6$) lower alkyl.

12. A compound that is
a) 3-[2-Methyl-4-(5H-pyrrolo[2,1-c][1,4]benzodiazepin-10(11H)-yl-carbonyl)phenyl]-2-methyl-cyclohex-2-en-1-one;
b) 3-[2-Chloro-5-methoxy-4-(5H-pyrrolo[2,1-c][1,4]benzodiazepin-10(11H)-yl-carbonyl)phenyl]-2-methyl-cyclohex-2-en-1-one;
c) (10,11-Dihydro-5H-pyrrolo[2,1-c][1,4]benzodiazepin-10-yl)-[2-chloro-4-(2-methyl-3-oxo-cyclohex-1-en-1-yl)-phenyl]-methanone;
d) 3-[4-(10,11-Dihydro-5H-pyrrolo[2,1-c][1,4]benzodiazepine-10-carbonyl)-phenyl]-cyclohex-2-en-1-one;
e) 3-[4-(10,11-Dihydro-5H-pyrrolo[2,1-c][1,4]benzodiazepine-10-carbonyl)-phenyl]-2-methyl-cyclohex-2-en-1-one;
f) 3-[4-(10,11-Dihydro-5H-pyrrolo[2,1-c][1,4]benzodiazepine-10-carbonyl)-2-methyl-phenyl]-cyclohex-2-en-1-one;

or a pharmaceutically acceptable salt form thereof.

13. A method for inhibiting preterm labor dysmenorrhea, endometritis, or for suppressing labor prior to caesarean delivery in a mammal, the method comprising administering to a mammal in need thereof a pharmaceutically effective amount of a compound of claim 12, or a pharmaceutically acceptable salt form thereof.

14. A method for treatment or inhibition of disorders in a mammal which are remedied or alleviated by vasopressin agonist activity selected from the group of diabetes insipidus, nocturnal enuresis, nocturia, urinary incontinence, or bleeding and coagulation disorders, the method comprising administering to a mammal in need thereof a pharmaceutically effective amount of a compound of claim 12, or a pharmaceutically acceptable salt form thereof.

15. A method for inducing temporary delay of urination in a mammal, the method comprising administering to a mammal in need thereof a pharmaceutically effective amount of a compound of claim 12, or a pharmaceutically acceptable salt form thereof.

* * * * *